(12) United States Patent
Gong et al.

(10) Patent No.: US 6,339,087 B1
(45) Date of Patent: Jan. 15, 2002

(54) CYCLIC AMINE DERIVATIVES-CCR-3 RECEPTOR ANTAGONISTS

(75) Inventors: Leyi Gong, San Mateo; Denis John Kertesz, Mountain View; David Bernard Smith, San Mateo; Francisco Xavier Talamas, Mountain View; Robert Stephen Wilhelm, Los Altos, all of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/197,282

(22) Filed: Nov. 20, 1998

Related U.S. Application Data

(63) Continuation-in-part of application No. 09/134,013, filed on Aug. 14, 1998.
(60) Provisional application No. 60/056,001, filed on Aug. 18, 1997.

(51) Int. Cl.[7] ...................... A61K 31/495; C07D 241/04
(52) U.S. Cl. ................... 514/252.12; 544/398; 544/400
(58) Field of Search ................................ 544/398, 400; 514/255, 252.12

(56) References Cited

U.S. PATENT DOCUMENTS

| | | | |
|---|---|---|---|
| 3,810,897 A | * 5/1974 | Philippe et al. | 260/268 |
| 4,559,349 A | 12/1985 | Storni | 514/318 |
| 4,579,947 A | 4/1986 | Devlin et al. | 544/400 |
| 4,857,330 A | * 8/1989 | Stephens et al. | 424/424 |
| 4,880,808 A | 11/1989 | Van Daele et al. | 544/360 |
| 4,882,432 A | 11/1989 | Abou-Gharbia et al. | 544/295 |
| 5,081,246 A | 1/1992 | Hidaka et al. | 544/363 |
| 5,434,158 A | 7/1995 | Shah | 514/278 |
| 5,508,997 A | 4/1996 | Katou | 370/16 |
| 5,784,547 A | 7/1998 | Dittmar et al. | 395/182.02 |
| 5,837,713 A | 11/1998 | Gleich | 514/312 |
| 5,849,732 A | * 12/1998 | Suzuki et al. | 514/212 |
| 6,072,053 A | 6/2000 | Vince et al. | 544/264 |

FOREIGN PATENT DOCUMENTS

| | | |
|---|---|---|
| CH | 615160 | 1/1980 |
| DE | 2614189 | 10/1977 |
| EP | 0 330 065 B1 | 8/1989 |
| EP | 0 343 961 B1 | 11/1989 |
| EP | 0 614 893 A1 | 9/1994 |
| EP | 0 669 322 A1 | 8/1995 |
| EP | 0 673 927 A1 | 9/1995 |
| EP | 0854610 | 7/1998 |
| JP | 09020759 | 1/1997 |
| WO | WO 92/12128 | 7/1992 |
| WO | WO 95/00507 | 1/1995 |
| WO | WO 95/13069 | 5/1995 |
| WO | WO 95/19345 | 7/1995 |
| WO | WO 96/06095 | 2/1996 |
| WO | WO 96/28424 | 9/1996 |
| WO | 97/19060 | 5/1997 |
| WO | 98/18247 | 4/1998 |

OTHER PUBLICATIONS

Harrison, I.T., et al., "Compendium of Organic Synthetic Methods", xi (index), (1971).
Hase, T.A., et al., "A Compilation of References on R–Functional Acyl Anion Synthons, RCO–", *Aldrichimica Acta, vol. 15, No. 2, 1982*, 35–41, (1982).
Huang, J., et al., "An Open Solution to Fault–Tolerant Ethernet: Design, Prototyping, and Evaluation", *IEEE Internation Performance, Computing and Communications Conference*, Phoenix / Scottsdale, Arizona, U.S.A., 459–468, (Feb., 1999).
Townsend, L.B., "Chemistry of the Heterocyclic Moiety of Purine Nucleosides and Some Closely Related Analogs", In: *Nucleoside Analogues—Chemistry, Biology, and Medical Applications*, Editor: Walker, R.T., et al., (eds.), Plenum Press, New York, 193–223, (1979).
Saxena et al. *J. Med. Chem.* 33, p. 2970–2976 (1990).*
Heath et al. *J. Clin. Invest.* 99, p. 178–184 (1997).*
Abstract for JP 62153280 (Jul. 18, 1987).
Abstract for JP 06107546 (Apr. 9, 1994).

* cited by examiner

*Primary Examiner*—Richard L. Raymond
(74) *Attorney, Agent, or Firm*—Rohan Peries; Rekha Bansal; Warren D. Woessner

(57) ABSTRACT

This invention relates to certain cyclic amine derivatives of Formula (I)

$$Ar-(F)-(E)-CR^3R^4-(CHR)_m-T\underset{R^2}{\overset{R^1}{\underset{|}{\underset{|}{\bigcirc}}}}U-Q-Ar^1 \quad (I)$$

that are CCR-3 receptor antagonist, pharmaceutical compositions containing them, methods for their use and methods for preparing these compounds.

23 Claims, No Drawings

CYCLIC AMINE DERIVATIVES-CCR-3 RECEPTOR ANTAGONISTS

CROSS-REFERENCE TO RELATED APPLICATIONS

This application is a continuation-in-part of U.S. patent application Ser. No. 09/134,013, filed on Aug. 14, 1998, which in turn claims the benefit under 35 U.S.C. 119(e) of U.S. Provisional Application Ser. No. 60/056,001, filed on Aug. 18, 1997, the disclosures of which are incorporated by reference.

FIELD OF THE INVENTION

This invention relates to certain cyclic amine derivatives that are CCR-3 receptor antagonists, pharmaceutical compositions containing them, methods for their use and methods for preparing these compounds.

BACKGROUND INFORMATION

Tissue eosinophilia is a feature of a number of pathological conditions such as asthma, rhinitis, eczema, inflammatory bowel diseases and parasitic infections ((see Bousquet, J. et al. *N. Eng. J. Med.* 323: 1033–1039 (1990) and Kay, A. B. and Corrigan. C. J. *Br. Med. Bull.* 48:51–64 (1992)). In asthma, eosinophil accumulation and activation are associated with damage to bronchial epithelium and hyper responsiveness to constrictor mediators. It is established that chemokines such as RANTES, eotaxin, MCP-2, MCP-3 and MCP-4 activate eosinophils ((see Baggiolini, M. and Dahinden, C. A. *Immunol. Today.* 15:127–133 (1994), Rot, A. M. et al. *J. Exp. Med.* 176, 1489–1495 (1992) and Ponath. P. D. et al. *J. Clin. Invest.*, Vol. 97, #3, 604–612 (1996)). However, unlike RANTES and MCP-3 which also induce the migration of other leukocyte cell types, eotaxin is selectively chemotactic for eosinophils ((see Griffith-Johnson, D. A et al. *Biochem. Biophy. Res. Commun.* 197:1167 (1993) and Jose, P. J. et al. *Biochem. Biophy. Res. Commun.* 207, 788 (1994)). Specific eosinophil accumulation was observed at the site of administration of eotaxin whether by intradermal or intraperitoneal injection or aerosol inhalation ((see Griffith-Johnson, D. A et al. *Biochem. Biophy. Res. Commun.* 197:1167 (1993); Jose, P. J. et al. *J. Exp. Med.* 179, 881–887 (1994); Rothenberg, M. E. et al. *J. Exp. Med.* 181, 1211 (1995) and Ponath. P. D. *J. Clin. Invest.*, Vol. 97, #3, 604–612 (1996)).

The CCR-3 receptor has been identified as a major chemokine receptor which eosinophils use for their response to eotaxin, RANTES and MCP-3. It is expressed predominantly on the surface of eosinophils and is highly selective for eotaxin. When transfected into a murine pre-β lymphoma line, the CCR-3 receptor bound eotaxin, RANTES and MCP-3 and conferred chemotactic responses on these cells to these chemokines ((see Ponath. P. D. et al. *J. Exp. Med.* 183, 2437–2448 (1996)).

Recently, studies have shown that pretreatment of eosinophils with an anti-CCR-3 mAb completely inhibits eosinophil chemotaxis to eotaxin, RANTES and MCP-3 ((see Heath H. et al. *J. Clin. Invest.*, Vol. 99, #2, 178–184 (1997)) indicating that CCR-3 antagonists are useful for the treatment of eosinophil-mediated inflammatory diseases. PCT Application WO 98/04554 discloses piperidine analogs that are CCR-3 receptor antagonists.

Glucocorticoids such as dexamethasone, methprednisolone and hydrocortisone have been used for treating many eosinophil-related disorders, including bronchial asthma ((R. P. Schleimer et. al., *Am. Rev. Respir. Dis.*, 141, 559 (1990)). The glucocorticoids are believed to inhibit IL-5, IL-3 mediated eosinophil survival in these diseases. However, prolonged use of glucocorticoids can lead to side effects such as glaucoma, osteoporosis and growth retardation in the patients ((see Hanania N. A et al., *J. Allergy and Clin. Immunol.*, Vol. 96, 571–579 (1995) and Saha M. T. et al, *Acta Paediatrica*, Vol. 86, #2, 138–142 (1997)). It is therefore desirable to have an alternative means of treating eosinophil related diseases without incurring these undesirable side effects.

The present invention provides a means of combating eosinophil induced diseases, such as asthma.

SUMMARY OF THE INVENTION

In a first aspect, this invention provides compounds selected from the group of compounds represented by Formula (I):

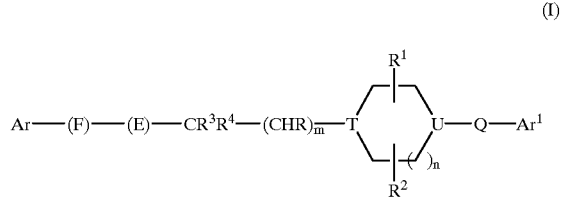

(I)

wherein:

T and U are both nitrogen; or one of T and U is —N— and the other is carbon; or one of T and U is —(N$^+$R$^{10}$)-X$^-$ and the other is carbon where R$^{10}$ is alkyl, haloalkyl, cyanoalkyl, hydroxyalkyl, alkoxyalkyl, carboxyalkyl, alkoxycarbonylalkyl, amidoalkyl, sulfonylaminoalkyl, or aralkyl and X$^-$ is a pharmaceutically acceptable counterion provided that n is 1;

R$^1$ and R$^2$ are, independently of each other, hydrogen or alkyl;

n is an integer from 0 to 2, provided that when n is 0, either T or U is carbon;

m is an integer from 0 to 3;

Ar and Ar$^1$ are, independently of each other, aryl or heteroaryl;

F is alkylene, alkenylene or a bond, provided that when T and U are nitrogen and F is alkylene, then R$^4$ is not aryl.

Each R is independently hydrogen or alkyl, or R together with either R$^3$ or R$^4$ and the atoms to which they are attached form a carbocycle or a heterocycle;

R$^3$ and R$^4$ are, independently of each other, selected from:
 (i) hydrogen, alkyl, alkenyl, haloalkyl, cycloalkyl, cycloalkylalkyl, heteroaryl, heteroaralkyl, heterocyclyl, heterocyclylalkyl, heteroalkyl, cyano or -(alkylene)-C(O)-Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy or heteroaralkyloxy, provided that when T and U are both nitrogen or one of T and U is —N— and the other is carbon, then both R$^3$ and R$^4$ are not hydrogen; or
 (ii) R$^3$ and R$^4$ together with the carbon atom to which they are attached form a carbocycle or a heterocycle;

E is —C(O)N(R$^5$)—, —SO$_2$N(R$^5$)—, —N(R$^6$)C(O)N (R$^5$)—, —N(R$^6$)SO$_2$N(R$^5$)—, —N(R$^6$)C(S)N(R$^5$)—,

—N($R^6$)C(O)—, —N($R^6$)C(O)O—, —OC(O)N($R^6$)— or —N($R^6$)$SO_2$— wherein:

$R^5$ is:
- (i) hydrogen, alkyl, acyl, haloalkyl, cycloalkyl, cycloalkylalkyl, aryl, aralkyl, aralkenyl, heteroaryl, heteroaralkyl, heterocyclylalkyl, heteroalkyl, or -(alkylene)-C(O)-Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy or heteroaralkyloxy; or
- (ii) $R^5$ together with either $R^3$ or $R^4$ and the atoms to which they are attached forms a heterocycloamino group; and $R^6$ is hydrogen, alkyl, acyl, haloalkyl, cycloalkyl, cycloalkylalkyl, aryl, aralkyl, aralkenyl, heteroaryl, heteroaralkyl, heterocyclylalkyl, heteroalkyl, or -(alkylene)-C(O)-Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy or heteroaralkyloxy, provided that when T is nitrogen and E is —C(O)N($R^5$)—, —$SO_2$N($R^5$)—, —N($R^6$)C(O)N($R^5$)—, —N($R^6$)$SO_2$N($R^5$)— or —N($R^6$)C(S)N($R^5$)—, then m>0; Q is —$R^7$—W—$R^8$— wherein:

$R^7$ is an alkylene chain of between 1–6 carbon atoms inclusive;

$R^8$ is a bond or an alkylene chain of between 1–4 carbon atoms inclusive;

W is a bond or a group selected from —C(O)—, —$NR^9$—, —O—, —S(O)$_{0-2}$—, —C(O)N($R^9$)—, —N($R^9$)C(O)—, —N($R^9$)$SO_2$—, —$SO_2$N($R^9$)—, —N($R^9$)C(O)N($R^9$)—, —N($R^9$)$SO_2$N($R^9$)— or —N($R^9$)C(S)N($R^9$)— wherein:

$R^9$ is hydrogen, alkyl, acyl, haloalkyl, cycloalkyl, cycloalkylalkyl, aryl, aralkyl, aralkenyl, heteroaryl, heteroaralkyl, heterocycloalkyl, heteroalkyl, or -(alkylene)-C(O)-Z where Z is alkyl, haloalkyl, alkoxy, haloalkyloxy, hydroxy, amino, mono- or disubstituted amino, aryl, aralkyl, aryloxy, aralkyloxy, heteroaryl, heteroaryloxy or heteroaralkyloxy, provided that when T is nitrogen and U is carbon then W is not —C(O)N($R^9$)—, and prodrugs, individual isomers, mixtures of isomers and pharmaceutically acceptable salts thereof.

In a second aspect, this invention provides pharmaceutical compositions containing a therapeutically effective amount of a compound of Formula (I) or its pharmaceutically acceptable salt and a pharmaceutically acceptable excipient.

In a third aspect, this invention provides a method of treatment of a disease in a mammal treatable by administration of a CCR-3 receptor antagonist, comprising administration of a therapeutically effective amount of a compound of Formula (I) or its pharmaceutically acceptable salt. The disease states include respiratory diseases such as asthma.

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, pentyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenylene" means a linear divalent hydrocarbon radical of two to six carbon atoms or a branched divalent hydrocarbon radical of three to six carbon atoms, containing at least one double bond, e.g., ethenylene, 2,4-pentadienylene, and the like.

"Acyl" means a radical —C(O)R where R is hydrogen, alkyl, alkenyl, cycloalkyl, heteroalkyl, haloalkyl, aryl, aralkyl, heteroaralkyl or heteroaryl, e.g., acetyl, benzoyl, thenoyl, and the like.

"Acyloxy" means a radical —OC(O)R where R is hydrogen, alkyl, alkenyl, cycloalkyl, heteroalkyl, haloalkyl or optionally substituted phenyl, e.g., acetoxy, benzoyloxy, and the like.

"Acylamino" means a radical —NRC(O)R' where R is hydrogen or alkyl and R' is hydrogen, alkyl, alkenyl, cycloalkyl, heteroalkyl, haloalkyl or optionally substituted phenyl, e.g., acetylamino, trifluoroacetylamino, benzoylamino, methylacetylamino, and the like.

"Halo" means fluoro, chloro, bromo or iodo, preferably fluoro and chloro.

"Haloalkyl" means alkyl substituted with one or more same or different halo atoms, e.g., —$CH_2Cl$, —$CF_3$, —$CH_2CF_3$, —$CH_2CCl_3$, and the like.

"Cycloalkyl" means a saturated monovalent cyclic hydrocarbon radical of three to six ring carbons, e.g., cyclopropyl, cyclohexyl, and the like.

"Carbocycle" means a saturated, cyclic group of 3 to 6 ring atoms in which all the ring atoms are carbon, e.g., cyclopentyl, cyclohexyl, and the like.

"Monosubstituted-amino" means a radical —NHR where R is alkyl, heteroalkyl, haloalkyl, cycloalkyl, cycloalkylalkyl or optionally substituted phenyl, e.g., methylamino, (1-methylethyl)amino, phenylamino, and the like.

"Disubstituted-amino" means a radical —NRR' where R and R' are independently alkyl, alkenyl, heteroalkyl, haloalkyl, cycloalkyl, cycloalkylalkyl or optionally substituted phenyl. Representative examples include, but are not limited to, dimethylamino, methylethylamino, di(1-methylethyl)amino, methylbenzylamino, and the like.

"Aryl" means a monovalent monocyclic or bicyclic aromatic hydrocarbon radical of 6 to 10 ring atoms, and optionally substituted independently with one or more substituents, preferably one, two or three substituents selected from alkyl, haloalkyl, heteroalkyl, cycloalkyl, cycloalkylalkyl, halo, cyano, nitro, acyloxy, alkoxy, optionally substituted phenyl, heteroaryl, heteroaralkyl, amino, monosubstituted amino, disubstituted amino, acylamino, hydroxylamino, amidino, guanidino, cyanoguanidinyl, hydrazino, hydrazido, —OR [where R is hydrogen, alkyl, haloalkyl, alkenyl, cycloalkyl, cycloalkylalkyl, optionally substituted phenyl, heteroaryl or heteroaralkyl], —S(O)$_n$R [where n is an integer from 0 to 2 and R is hydrogen, alkyl, haloalkyl, alkenyl, cycloalkyl, cycloalkylalkyl, optionally substituted phenyl, heteroaryl, heteroaralkyl, amino, mono or disubstituted amino], —NRSO$_2$R' (where R is hydrogen or alkyl and R' is alkyl, amino, monosubstituted or disubstituted amino) —C(O)R (where R is hydrogen, alkyl, alkenyl, cycloalkyl, heteroalkyl, haloalkyl or optionally substituted phenyl), —COOR (where R is hydrogen, alkyl, optionally substituted phenyl, heteroaryl or heteroaralkyl), -(alkylene)-COOR (where R is hydrogen, alkyl, optionally substituted phenyl, heteroaryl or heteroaralkyl), methylenedioxy, 1,2-ethylenedioxy, —CONR'R" or -(alkylene)CONR'R" (where R' and R" are independently selected from hydrogen, alkyl, cycloalkyl, haloalkyl, cycloalkylalkyl, optionally substituted phenyl, heteroaryl and heteroaralkyl). More specifically the term aryl includes, but is not limited to, phenyl, 1-naphthyl, 2-naphthyl, and derivatives thereof.

"Optionally substituted phenyl" means a phenyl group which is optionally substituted independently with one, two or three substituents selected from alkyl, haloalkyl, halo, nitro, cyano, —OR (where R is hydrogen or alkyl), —NRR' (where R and R' are independently of each other hydrogen or alkyl), —COOR (where R is hydrogen or alkyl) or —CONR'R" (where R' and R" are independently selected from hydrogen or alkyl).

"Heteroaryl" means a monovalent monocyclic or bicyclic aromatic radical of 5 to 10 ring atoms containing one, two, or three ring heteroatoms selected from N, O, or S, the remaining ring atoms being C. The aromatic radical is optionally substituted independently with one or more substituents, preferably one or two substituents selected from alkyl, haloalkyl, heteroalkyl, cycloalkyl, cycloalkylalkyl, halo, cyano, nitro, acyloxy, optionally substituted phenyl, amino, monosubstituted amino, disubstituted amino, acylamino, hydroxyamino, amidino, guanidino, cyanoguanidinyl, hydrazino, hydrazido, —OR [where R is hydrogen, alkyl, haloalkyl, alkenyl, cycloalkyl, cycloalkylalkyl or optionally substituted phenyl], —S(O)$_n$R [where n is an integer from 0 to 2 and R is hydrogen, alkyl, haloalkyl, alkenyl, cycloalkyl, cycloalkylalkyl, optionally substituted phenyl, amino, mono or disubstituted amino], —C(O)R (where R is hydrogen, alkyl, alkenyl, cycloalkyl, heteroalkyl, haloalkyl or optionally substituted phenyl), —COOR (where R is hydrogen, alkyl, or optionally substituted phenyl), -(alkylene)-COOR (where R is hydrogen, alkyl or optionally substituted phenyl), methylenedioxy, 1,2-ethylenedioxy, —CONR'R" or -(alkylene)-CONR'R" (where R' and R" are independently selected from hydrogen, alkyl, cycloalkyl, haloalkyl, cycloalkylalkyl or optionally substituted phenyl). More specifically the term heteroaryl includes, but is not limited to pyridyl, pyrrolyl, thiophene, pyrazolyl, thiazolyl, imidazolyl, pyrimidinyl, thiadiazolyl, indolyl, carbazolyl, azaindolyl, benzofuranyl, benzotriazolyl, benzisoxazolyl, purinyl, quinolinyl, benzopyranyl, and derivatives thereof.

"Heterocycloamino" means a saturated or unsaturated monovalent cyclic group of 5 to 8 ring atoms, wherein at least one ring atom is N and optionally contains a second ring heteroatom selected from the group consisting of N, O, or S(O)$_n$ (where n is an integer from 0 to 2), the remaining ring atoms being C. The heterocycloamino ring may be fused to a heteroaryl ring, or it may be optionally substituted independently with one or more substituents, preferably one or two substituents, selected from alkyl, haloalkyl, cycloalkyl, cycloalkylalkyl, aryl, aralkyl, heteroaryl, heteroaralkyl, halo, cyano, acyl, amino, monosubstituted amino, disubstituted amino, —COOR (where R is hydrogen or alkyl), —XR (where X is O or S(O)$_n$, n is an integer from 0 to 2, and R is hydrogen, alkyl, haloalkyl, cycloalkyl, cycloalkylalkyl, aryl, aralkyl, heteroaryl or heteroaralkyl) or —CONR'R" (where R' and R" are independently selected from hydrogen or alkyl). Representative examples include but are not limited to pyrrolidino, piperidino, 4-benzoylpiperidino, morpholino, piperazino, 4-(4-benzyloxyphenyl)piperazino, indolino, and the like.

"Heterocycle" or "Heterocyclyl" means a saturated or unsaturated cyclic radical of 3 to 8 ring atoms in which one or two ring atoms are heteroatoms selected from N, O, or S(O)$_n$ (where n is an integer from 0 to 2). The heterocyclo ring may be optionally substituted independently with one, two or three substituents selected from alkyl, haloalkyl, cycloalkyl, cycloalkylalkyl, aryl, aralkyl, heteroaryl, heteroaralkyl, halo, cyano, acyl, acylamino, amino, monosubstituted amino, disubstituted amino, —COOR (where R is hydrogen or alkyl), —XR (where X is O or S(O)$_n$, where n is an integer from 0 to 2 and R is hydrogen, alkyl, haloalkyl, cycloalkyl, aralkyl, aryl, heteroaryl or heteroaralkyl) or —CONR'R" (where R' and R" are independently selected from hydrogen or alkyl). Representative examples include, but are not limited to tetrahydropyranyl, piperidino, 1-(4-chlorophenyl)piperidino, and the like.

"Heteroalkyl" means an alkyl, cycloalkyl, or cycloalkylalkyl radical as defined above, carrying a substituent containing a heteroatom selected from N, O, S(O)$_n$ where n is an integer from 0 to 2. Representative substituents include —NR"R$^b$, —OR$^a$ or —S(O)$_{nR}{}^c$, wherein n is an integer from 0 to 2, R$^a$ is hydrogen, alkyl, haloalkyl, cycloalkyl, cycloalkylalkyl, optionally substituted phenyl, pyridyl, or —COR (where R is alkyl), R$^b$ is hydrogen, alkyl, —SO$_2$R (where R is alkyl or hydroxyalkyl), —SO$_2$NRR' (where R and R' are independently of each other hydrogen or alkyl), —CONR'R", (where R' and R" are independently selected from hydrogen or alkyl) and R$^c$ is hydrogen, alkyl, cycloalkyl, cycloalkylalkyl, optionally substituted phenyl, amino, monosubstituted amino, or disubstituted amino. Representative examples include, but are not limited to 2-methoxyethyl, benzyloxymethyl, thiophen-2-ylthiomethyl, and the like.

"Hydroxyalkyl" means a linear monovalent hydrocarbon radical of two to six carbon atoms or a branched monovalent hydrocarbon radical of three or six carbons substituted with one or two hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Aminoalkyl" means an alkyl radical as defined above, carrying one or two amino groups, e,g., 2-aminoethyl, 2-aminopropyl, 3-aminopropyl, 1-(aminomethyl)-2-methylpropyl, and the like. "Amidoalkyl" means an alkyl radical as defined above, carrying a —NRCOR$^3$ group where R is hydrogen or alkyl and R$^3$ is alkyl as defined above, e,g., —(CH$_2$)$_2$NHCOCH$_3$, —(CH$_2$)$_3$NHCOCH$_3$, and the like.

"Sulfonylaminoalkyl" means an alkyl radical as defined above, a —NRSO$_2$R$^a$ group, e,g., —(CH$_2$)$_2$NHSO$_2$CH$_3$, —(CH$_2$)$_3$NHSO$_2$CH$_3$, —(CH$_2$)$_2$NHSO$_2$C$_2$H$_5$, and the like.

"Carboxyalkyl" means an alkyl radical as defined above, carrying a carboxy group, e,g., carboxymethyl, 2-carboxyethyl, 2-carboxypropyl, 3-carboxypropyl, 1-(carboxymethyl)-2-methylpropyl, and the like.

"Alkoxycarbonylalkyl" means an alkyl radical as defined above, carrying a —COOR group where R is an alkyl group as defined above, e,g., 2-methoxycarbonylethyl, ethoxycarbonylmethyl, 2-ethoxycarbonylethyl, 3-ethoxycarbonylpropyl, 3-methoxycarbonylpropyl, and the like.

"Alkoxyalkyl" means an alkyl radical as defined above, carrying an alkoxy group, e,g., methoxymethyl, 2-methoxyethyl, 2-methoxypropyl, 3-methoxypropyl, 1-(methoxymethyl)-2-methylpropyl, and the like.

"Cyanoalkyl" means an alkyl radical as defined above, carrying a cyano group, e,g., 2-cyanoethyl, 2-cyanopropyl, 3-cyanopropyl, 1-(cyanomethyl)-2-methylpropyl, and the like.

"Cycloalkylalkyr" means a radical —$R^aR^b$ where $R^a$ is an alkylene group and $R^b$ is a cycloalkyl group as defined above e.g., cyclopropylmethyl, cyclohexylpropyl, 3-cyclohexyl-2-methylpropyl, and the like.

"Aralkyl" means a radical —$R^aR^b$ where $R^a$ is an alkylene group and $R^b$ is an aryl group as defined above e.g., benzyl, phenylethyl, 3-(3-chlorophenyl)-2-methylpentyl, and the like.

"Heteroaralkyl" means a radical —$R^aR^b$ where $R^a$ is an alkylene group and $R^b$ is a heteroaryl group as defined above e.g., pyridin-3-ylmethyl, 3-(benzofuran-2-yl)propyl, and the like.

"Heterocyclylalkyl" means a radical —$R^aR^b$ where $R^a$ is an alkylene group and $R^b$ is a heterocyclyl group as defined above e.g., tetrahydropyran-2-ylmethyl, 4-methylpiperazin-1-ylethyl, and the like.

"Alkoxy", "haloalkyloxy", "aryloxy", "heteroaryloxy", "aralkyloxy", or "heteroaralkyloxy" means a radical —OR where R is an alkyl, haloalkyl, aryl, heteroaryl, aralkyl, or heteroaralkyl respectively as defined above e.g., methoxy, phenoxy, pyridin-2-yloxy, benzyloxy, and the like.

"Optional" or "optionally" means that the subsequently described event or circumstance may but need not occur, and that the description includes instances where the event or circumstance occurs and instances in which it does not. For example, "heterocyclo group optionally mono- or di- substituted with an alkyl group" means that the alkyl may but need not be present, and the description includes situations where the heterocyclo group is mono- or disubstituted with an alkyl group and situations where the heterocyclo group is not substituted with the alkyl group.

"Amino-protecting group" refers to those organic groups intended to protect nitrogen atoms against undesirable reactions during synthetic procedures e.g., benzyl, benzyloxycarbonyl (CBZ), t-butoxycarbonyl (BOC), trifluoroacetyl, and the like.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the $R^3$ and $R^4$ substituents in a compound of Formula (I) are different, then the carbon to which they are attached is an asymmetric center and the compound of Formula (1) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

A "pharmaceutically acceptable counterion" means an ion having a charge opposite to that of the substance with which it is associated and that is pharmaceutically acceptable. Representative examples include, but are not limited to, chloride, bromide, iodide, methanesulfonate, p-tolylsulfonate, trifluoroacetate, acetate, and the like.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Leaving group" has the meaning conventionally associated with it in synthetic organic chemistry i.e., an atom or group capable of being displaced by a nucleophile and includes halogen, alkanesulfonyloxy, arenesulfonyloxy, ester, or amino such as chloro, bromo, iodo, mesyloxy, tosyloxy, trifluorosulfonyloxy, methoxy, N,O-dimethylhydroxylamino, and the like.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, sulfhydryl or amino group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Nomenclature

The nomenclature used in this application is generally based on the IUPAC recommendations, e.g., a compound of Formula (I) where T and U are nitrogen, n and m are 1, R, $R^1$, $R^2$ and $R^3$ are hydrogen, $R^4$ is 1-methylethyl, E is —C(O)NH—, F is a bond, Q is —$CH_2$—, Ar is phenyl, $Ar^1$ is 3,4-chlorophenyl and the stereochemistry at the carbon to which $R^3$ and $R^4$ are attached is RS is named, N-{1(RS)-[4-(3,4-dichlorobenzyl)piperazin-1-ylmethyl]-2-methylpropyl}benzamide.

a compound of Formula (I) where T and U are nitrogen, n and m are 1, R, $R^1$, $R^2$ and $R^3$ are hydrogen, $R^4$ is 1,1-dimethylethyl, E is —NHC(O)NH—, F is a bond, Q is —$CH_2$—, Ar is phenyl, $Ar^1$ is 3,4-chlorophenyl and the stereochemistry at the carbon to which $R^3$ and $R^4$ are attached is RS is named, 1-{1(RS)-[4-(3,4-dichlorobenzyl)piperazin-1-yl-methyl]-2,2-dimethylpropyl}-3-phenylurea.

a compound of Formula (I) where T and U are nitrogen, n and m are 1, R, $R^1$, $R^2$ and $R^3$ are hydrogen, E is —C(O)$NR^5$—, $R^4$ and $R^5$ together form a 3-pyrrolino ring, F is a bond, Q is —$CH_2$—, Ar is 4-methylphenyl, $Ar^1$ is 3,4-chlorophenyl and the stereochemistry at the carbon to which $R^3$ and $R^4$ are attached is RS is named, {2-(RS)-[4-(3,4-dichloro-benzyl)piperazin-1-ylmethyl]-1-(4-methylbenzoyl)-3-pyrroline.

a compound of Formula (I) where T is nitrogen, U is carbon, n and m are 1, R, $R^1$, $R^2$ and $R^3$ are hydrogen, $R^4$ is 1-methylethyl, E is —C(O)NH—, F is a bond, Q is —$CH_2$—, Ar is 4-methylphenyl, $Ar^1$ is 3,4-chlorophenyl and the stereochemistry at the carbon to which $R^3$ and $R^4$ are attached is S is named, N-{1(S)-[4-(3,4-dichlorobenzyl)piperidin-1-yl-methyl]-2-methylpropyl}-4-methylbenzamide.

a compound of Formula (I) where T is —$N^+R^{10}$—, U is carbon, m is 1, R, $R^1$, $R^2$ and $R^3$ are hydrogen, $R^4$ is 1-methylethyl, $R^{10}$ is ethyl, X is iodide, E is —NHC(O)NH—, F is a bond, Q is —$CH_2$—, Ar is 3,4,5-trimethoxyphenyl, $Ar^1$ is 3,4-chlorophenyl and the stereochemistry at the carbon to which $R^3$ and $R^4$ are attached is R is named, 4-(3,4-dichlorobenzyl)-1-ethyl-1-{3-methyl-2(R)-[3-(3,4,5-trimethoxyphenyl)ureido]butyl}-piperidinium iodide.

a compound of Formula (I) where T is —$N^+R^{10}$—, U is carbon, m is 1, R, $R^1$, $R^2$ and $R^3$ are hydrogen, $R^4$ is 1-methylethyl, $R^{10}$ is methyl, X is chloride, E is —C(O)NH—, F is a bond, Q is —$CH_2$—, Ar is 4-(2-aminoethyl)phenyl, $Ar^1$ is 3,4-chlorophenyl and the stereochemistry at the carbon to which $R^3$ and $R^4$ are attached is R is named, 1-{2-(R)-[4-(2-aminoethyl)-benzoylamino]-3-methylbutyl}-4-(3,4-dichlorobenzyl)-1-methyl-piperidinium chloride.

Representative compounds of this invention are as follows: I. Representative compounds of Formula (I) where T and U = nitrogen; m and n = 1; R = $R^1$ = $R^2$ = $R^3$ = hydrogen; Q = —$CH_2$—; E = —C(O)NH— and other groups are as defined below are:

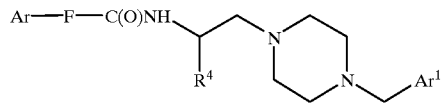

| CPD # | Stereo-chem. | Ar | F | $R^4$ | $Ar^1$ | M.Pt. °C | Mass. Spec m/e |
|---|---|---|---|---|---|---|---|
| 1 | (R) | 4-methylphenyl | bond | 1-methylethyl | 3,4-dichlorophenyl .2HCl | 232–232.4 | |
| 2 | (S) | 4-methylphenyl | bond | 1,1-dimethylethyl | 3,4-dichlorophenyl .2HCl | 238–242 | |
| 3 | (S) | 4-methoxyphenyl | bond | 1-methylethyl | 3,4-dichlorophenyl .2HCl | 222.5–223 | |
| 4 | (RS) | 3,4-methylene- | bond | 1-methylethyl | 3,4-dichlorophenyl | | 477 |

-continued

Representative compounds of this invention are as follows: I. Representative compounds of Formula (I) where T and U = nitrogen; m and n = 1; R = $R^1$ = $R^2$ = $R^3$ = hydrogen; Q = —$CH_2$—; E = —C(O)NH— and other groups are as defined below are:

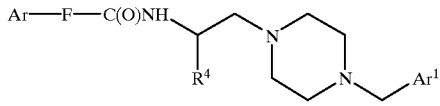

| CPD # | Stereo-chem. | Ar | F | $R^4$ | $Ar^1$ | M.Pt. °C | Mass. Spec m/e |
|---|---|---|---|---|---|---|---|
|   |   | dioxyphenyl |   |   |   |   |   |
| 5 | (RS) | 3,4-difluorophenyl | bond | 1-methylethyl | 3,4-dichlorophenyl |   | 469 |
| 6 | (RS) | thiophen-2-yl | bond | 1-methylethyl | 3,4-dichlorophenyl |   | 439 |
| 7 | (RS) | 2-pyridyl | bond | 1-methylethyl | 3,4-dichlorophenyl .2HCl | 226.2–229.9 |   |
| 8 | (S) | 4-methylphenyl | bond | 1-methylethyl | 3,4-dichlorophenyl .2HCl | 229–229.6 |   |
| 9 | (RS) | 4-methylphenyl | bond | 1-methylethyl | 4-nitrophenyl |   | 424 |
| 10 | (R) | 3-cyanophenyl | bond | 1-methylethyl | 3,4-dichlorophenyl |   | 458 |
| 11 | (RS) | 4-methylthiophenyl | bond | 1-methylethyl | 3,4-dichlorophenyl |   |   |
| 12 | (RS) | 4-acetylphenyl | bond | 1-methylethyl | 3,4-dichlorophenyl |   | 475 |
| 13 | (RS) | 2-benzofuranyl | bond | 1-methylethyl | 3,4-dichlorophenyl |   | 473 |
| 14 | (RS) | 4-N,N-dimethyl aminophenyl | bond | 1-methylethyl | 3,4-dichlorophenyl |   | 476 |
| 15 | (RS) | 2-indolyl | bond | 1-methylethyl | 3,4-dichlorophenyl |   | 472 |
| 16 | (RS) | 4-biphenyl | bond | 1-methylethyl | 3,4-dichlorophenyl |   | 509 |
| 17 | (RS) | 4-methylsulfonyl phenyl | bond | 1-methylethyl | 3,4-dichlorophenyl |   | 511 |
| 18 | (RS) | 4-aminophenyl | bond | 1-methylethyl | 3,4-dichlorophenyl |   | 448 |
| 19 | (S) | 2-naphthyl | bond | 1-methylethyl | 3,4-dichlorophenyl |   | 483 |
| 20 | (RS) | 4-pyridyl | bond | 1-methylethyl | 3,4-dichlorophenyl .2HCl | 150–153 |   |
| 21 | (RS) | 4-ethylenephenyl | bond | 1-methylethyl | 3,4-dichlorophenyl |   | 459 |
| 22 | (S) | 4-methylphenyl | bond | cyclohexyl | 3,4-dichlorophenyl .2HCl | 145.9–148.2 |   |
| 23 | (RS) | 4-methylphenyl | bond | n-propyl | 3,4-dichlorophenyl .2HCl | 199.5–203.5 |   |
| 24 | (RS) | 2-quinolinyl | bond | 1-methylethyl | 3,4-dichlorophenyl |   | 484 |
| 25 | (RS) | thiophen-2-yl | —$CH_2$— | 1-methylethyl | 3,4-dichlorophenyl |   | 453 |
| 26 | (RS) | 4-cyanophenyl | bond | 1-methylethyl | 4-chlorophenyl |   | 424 |
| 27 | (S) | 4-amino-5-chloro-2-methoxyphenyl | bond | 1,1-dimethylethyl | 3,4-dichlorophenyl .2HCl | 194.8–196.1 |   |
| 28 | (RS) | 4-(pyrrol-1-yl)-phenyl | bond | 1-methylethyl | 3,4-dichlorophenyl |   | 498 |
| 29 | (RS) | 5-nitrofuran-2-yl | bond | 1-methylethyl | 3,4-dichlorophenyl |   | 468 |
| 30 | (RS) | 5-methoxyindol-2-yl | bond | 1-methylethyl | 3,4-dichlorophenyl |   | 502 |
| 31 | (RS) | 3,4-methylene-dioxyphenyl | bond | 1-methylethyl | 4-chlorophenyl |   | 443 |
| 32 | (RS) | phenyl | —$(CH_2)_2$— | 1-methylethyl | 3,4-dichlorophenyl |   | 461 |
| 33 | (S) | 4-chlorophenyl | bond | methyl | 3,4-dichlorophenyl .2HCl | 244–246.5 |   |
| 34 | (RS) | 4-chlorophenyl | bond | phenyl | 3,4-dichlorophenyl .2HCl | 117–183 |   |
| 35 | (R) | 4-chlorophenyl | bond | cyclohexyl | 3,4-dichlorophenyl | 149–155 |   |
| 36 | (RS) | 5-chloroindol-2-yl | bond | 1-methylethyl | 3,4-dichlorophenyl |   | 506 |
| 37 | (RS) | 4-biphenyl | bond | 2-methylpropyl | 3,4-dichlorophenyl |   | 523 |
| 38 | (RS) | 3-chloro-2-nitro-phenyl | bond | 1-methylethyl | 3,4-dichlorophenyl |   | 512 |
| 39 | (RS) | 2,4,6-trimethylphenyl | bond | 1-methylethyl | 3,4-dichlorophenyl |   | 475 |
| 40 | (RS) | 4-chlorophenyl | bond | benzyl | 3,4-dichlorophenyl .2HCl | 137–142 |   |
| 41 | (RS) | anthraquinon-2-yl | bond | 1-methylethyl | 3,4-dichlorophenyl |   | 563 |
| 42 | (RS) | benzothiophen-2-yl | bond | 1-methylethyl | 4-chlorophenyl |   | 455 |
| 43 | (RS) | 2-phenoxyphenyl | bond | 1-methylethyl | 3,4-dichlorophenyl |   | 525 |
| 44 | (RS) | 4-methylphenyl | ethenylene | 1-methylethyl | 3,4-dichlorophenyl |   | 473 |
| 45 | (RS) | 4-methylphenyl | bond | 1-methylethyl | 4-chlorophenyl |   |   |
| 46 | (RS) | 4-methylphenyl | bond | 1-methylethyl | 4-nitrophenyl |   |   |
| 47 | (RS) | 4-methylphenyl | bond | 1-methylethyl | 3,4-difluorophenyl |   |   |
| 48 | (RS) | 4-methylphenyl | bond | 1,1-dimethylethyl | 3,4-dichlorophenyl |   |   |
| 49 | (RS) | 4-methylphenyl | bond | 1-methylethyl | 2,3-dichlorophenyl |   |   |
| 50 | (RS) | 4-methylphenyl | bond | 1-methylethyl | 3-methyl-4-nitrophenyl |   |   |
| 51 | (RS) | 4-methylphenyl | bond | 1-methylethyl | 3-chloro-4-fluorophenyl |   |   |
| 52 | (R) | 4-methylphenyl | bond | 1,1-dimethylethyl | 3-chloro-4-fluorophenyl |   |   |
| 53 | (R) | 4-methylphenyl | bond | 1,1-dimethylethyl | 3-methylbenzothiophen-2-yl |   |   |
| 54 | (R) | 4-methylphenyl | bond | 1,1-dimethylethyl | 1-acetylindol-3-yl |   |   |
| 55 | (R) | 4-methylphenyl | bond | 1,1-dimethylethyl | 5-nitrothiophen-3-yl |   |   |

-continued

Representative compounds of this invention are as follows: I. Representative compounds of Formula
(I) where T and U = nitrogen; m and n = 1; R = R¹ = R² = R³ = hydrogen;
Q = —CH₂—; E = —C(O)NH— and other groups are as defined below are:

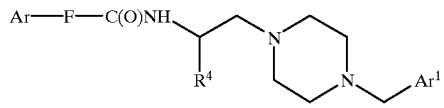

| CPD # | Stereo-chem. | Ar | F | R⁴ | Ar¹ | M.Pt. °C | Mass. Spec m/e |
|---|---|---|---|---|---|---|---|
| 56 | (R) | quinolin-3-yl | bond | 1,1-dimethylethyl | 3,4-dichlorophenyl | | | and are named as:
2. N-{1(S)-[4-(3,4-Dichlorobenzyl)piperazin-1-ylmethyl]-2,2-dimethylpropyl}-4-methylbenzamide dihydrochloride salt.
3. N-{1(S)-[4-(3,4-Dichlorobenzyl)piperazin-1-ylmethyl]-2-methylpropyl}-4-methoxybenzamide dihydrochloride salt.
4. N-{1(RS)-[4-(3,4-Dichlorobenzyl)piperazin-1-ylmethyl]-2-methylpropyl}-3,4-methylenedioxybenzamide.
7. N-{1(RS)-[4-(3,4-Dichlorobenzyl)piperazin-1-ylmethyl]-2-methylpropyl}picolinamide dihydrochloride salt.
18. N-{1(S)-[4-(3,4-Dichlorobenzyl)piperazin-1-ylmethyl]-2-methylpropyl}-4-methylbenzamide dihydrochloride salt.
19. N-{1(S)-[4-(3,4-Dichlorobenzyl)piperazin-1-ylmethyl]-2-methylpropyl}-2-naphthaleneamide.
25. N-{1(RS)-[4-(3,4-Dichlorobenzyl)piperazin-1-ylmethyl]-2-methylpropyl}-2-(thiophen-2-yl)acetamide.
35. N-{1(R)-cyclohexyl-2-[4-(3,4-dichlorobenzyl)piperazin-1-yl]ethyl}4-chloro-benzamide.
37. N-{1(RS)-[4-(3,4-Dichlorobenzyl)piperazin-1-ylmethyl]-3-methylbutyl}-4-phenylbenzamide.
44. N-{1(RS)-[4-(3,4-Dichlorobenzyl)piperazin-1-ylmethyl]-2-methylpropyl}-3-(4-methylphenyl)acrylamide.

II. Representative compounds of Formula (I) where T = nitrogen, U = carbon; m and n = 1;
R = R¹ = R² = R³ = hydrogen; F = bond;
E = —C(O)NH— and other groups are as defined below are:

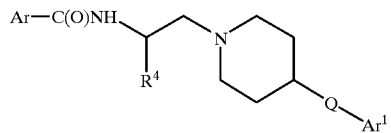

| CPD # | Stereo-chem | Ar | R⁴ | Q | Ar¹ | M.Pt. °C. | Mass. Spec. m/e |
|---|---|---|---|---|---|---|---|
| 57 | (S) | 4-methylphenyl | 1-methylethyl | —CH₂— | 3,4-dichlorophenyl.HCl | 87–90 | |
| 58 | (S) | 4-methylphenyl | 1,1-dimethylethyl | —CH₂— | 3,4-dichlorophenyl.HCl | 153.1–154.2 | |
| 59 | (RS) | 4-methylphenyl | 1-methylethyl | —CH₂NHC(O)— | 4-amino-5-chloro-2-methoxyphenyl | | 515.6 |
| 60 | (RS) | 4-chlorophenyl | 1-methylethyl | —CH₂— | 3,4-dichlorophenyl | | 467.86 |
| 61 | (S) | 4-chlorophenyl | 1,1-dimethylethyl | —CH₂— | 3,4-dichlorophenyl | 63–68 | |
| 62 | (RS) | 4-methylphenyl | 1-methylethyl | —CH₂— | 4-chlorophenyl.HCl | 123–128 | |
| 63 | (R) | 4-(2-acetylamino-ethyl)phenyl | 1-methylethyl | —CH₂— | 3,4-dichlorophenyl.HCl | 113.3–113.9 | |
| 64 | (R) | 4-[(2-(R)-amino-3-methylbutyryl-amino)ethyl)]phenyl | 1-methylethyl | —CH₂— | 3,4-dichlorophenyl.2HCl | 191–199 | |
| 65 | (R) | 4-(2-aminoethyl)-phenyl | 1,1-dimethylethyl | —CH₂— | 3,4-dichlorophenyl.2HCl | 192–198 | |
| 66 | (R) | 4-aminomethyl-phenyl | 1,1-dimethylethyl | —CH₂— | 3,4-dichlorophenyl.2HCl | | 476 |
| 67 | (R) | quinolin-3-yl | 1,1-dimethylethyl | —CH₂— | 3,4-dichlorophenyl.HCl | | 534 |
| 68 | (R) | 4-methylphenyl | 1,1-dimethylethyl | —CH₂— | 4-nitrophenyl | | |
| 69 | (R) | pyridin-2-yl | 1,1-dimethylethyl | —CH₂— | 4-nitrophenyl.HCl | | 425 |
| 70 | (R) | pyridin-2-yl | 1,1-dimethylethyl | —CH₂— | 4-nitrophenyl | | |
| 71 | (R) | 5-methylthiophen-2-yl | 1-methylethyl | —CH₂— | 3,4-dichlorophenyl.HCl | 45–47.5 | |
| 72 | (R) | 4-(2-aminoethyl)-phenyl | 1-methylethyl | —CH₂— | 3,4-dichlorophenyl.2HCl | | 476 |
| 73 | (R) | 4-methylphenyl | 1,1-dimethylethyl | —CH₂— | 3,4-dichlorophenyl.2HCl | 153.1–154.2 | |
| 74 | (R) | 4-methylsulfonyl-phenyl | 1,1-dimethylethyl | —CH₂— | 3,4-dichlorophenyl | 205–214 | |
| 75 | (R) | 5-methylthiophen-2-yl | 1,1-dimethylethyl | —CH₂— | 3,4-dichlorophenyl.HCl | 161–162.5 | |
| 76 | (R) | 4-hydroxymethyl-phenyl | 1-methylethyl | —CH₂— | 3,4-dichlorophenyl | | 463 |

II. Representative compounds of Formula (I) where T = nitrogen, U = carbon; m and n = 1; R = R¹ = R² = R³ = hydrogen; F = bond; E = —C(O)NH— and other groups are as defined below are:

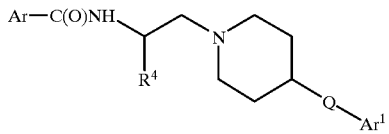

| CPD # | Stereo-chem | Ar | R⁴ | Q | Ar¹ | M.Pt. ° C. | Mass. Spec. m/e |
|---|---|---|---|---|---|---|---| and are named as:
57. N-{1(S)-[4-(3,4-Dichlorobenzyl)piperidin-1-ylmethyl]-2-methylpropyl}-4-methylbenzamide hydrochloride salt.
59. N-{1(RS)-[4-(4-Amino-5-chloro-2-methoxyphenylcarbonylaminomethyl)piperidin-1-ylmethyl]-2-methylpropyl}-4- methylbenzamide.

III. Representative compounds of Formula (I) where T and U = nitrogen; m and n = 1; R = R¹ = R² = R³ = hydrogen; Q = —CH₂— and F = bond; E = —C(O)NR⁵—; R⁵ together with R⁴ and the atoms to which they are attached = heterocycloamino group and other groups are as defined below are:

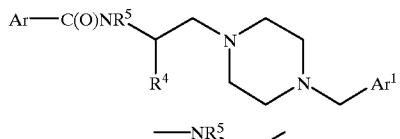

| CPD # | Stereo-chem | Ar | R⁴ | Ar¹ | M.Pt. ° C. |
|---|---|---|---|---|---|
| 77 | (RS) | 4-methylphenyl | piperidino | 3,4-dichlorophenyl.2HCl | 259.6–260 |
| 78 | (R) | 4-methylphenyl | pyrrolidino | 3,4-dichlorophenyl.2HCl | 249.6–250.1 |
| 79 | (RS) | 4-chlorophenyl | piperidino | 3,4-dichlorophenyl.2HCl | 239.6–240.5 |
| 80 | (RS) | 4-methylphenyl | 3-pyrrolino | 3,4-dichlorophenyl.2HCl | 242–243 | and are named as:
77. {1-(4-Methylbenzoyl)-2(RS)[4-(3,4-dichlorobenzyl)piperazin-1-ylmethyl)}piperidine dihydrochloride salt.

IV. Representative compounds of Formula (I) where T and U = nitrogen; m and n = 1;
$R^1 = R^2 = R^3$ = hydrogen; Q = —CH$_2$—;
E = —NHC(O)NH— and other groups are as defined below are:

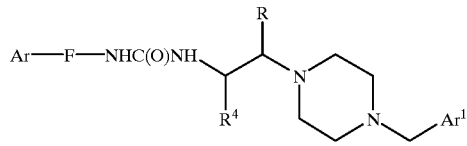

| CPD # | Stereo-chem | Ar | F | R + R$^4$ | R | R$^4$ | Ar$^1$ | M.Pt. | Mass Spec. m/e |
|---|---|---|---|---|---|---|---|---|---|
| 81 | (R) | 3-methoxyphenyl | bond | | H | 1-methylethyl | 3,4-dichlorophenyl | | 478 |
| 82 | (RS) | 2,5-dimethoxyphenyl | bond | | H | 1-methylethyl | 3,4-dichlorophenyl | | 508 |
| 83 | (RS) | 2-ethylphenyl | bond | | HM | 1-methylethyl | 3,4-dichlorophenyl | | 477 |
| 84 | (RS) | 3-methoxyphenyl | bond | cyclohexyl | | | 3,4-dichlorophenyl | | 491.46 |
| 85 | (RS) | 3-ethylphenyl | bond | | H | 1-methylethyl | 3,4-dichlorophenyl | | 476 |
| 86 | (RS) | 2-ethoxyphenyl | bond | | H | 1-methylethyl | 3,4-dichlorophenyl | | 492 |
| 87 | (RS) | 2,3-dichlorophenyl | bond | | H | 1-methylethyl | 3,4-dichlorophenyl | | 516 |
| 88 | (RS) | 3-bromophenyl | bond | | H | 1-methylethyl | 3,4-dichlorophenyl | | 526 |
| 89 | (RS) | phenyl | bond | | H | 1-methylethyl | 4-chlorophenyl | | 414 |
| 90 | (RS) | 3-chloro-2-methyl-phenyl | bond | | H | 1-methylethyl | 3,4-dichlorophenyl | | 496 |
| 91 | (RS) | 3-acetylphenyl | bond | | H | 1-methylethyl | 3,4-dichlorophenyl | | 490 |
| 92 | (RS) | phenyl | —CH$_2$— | | H | 1-methylethyl | 3,4-dichlorophenyl | | 462 |
| 93 | (R) | 2,4,6-trimethylphenyl | bond | | H | 1-methylethyl | 3,4-dichlorophenyl | 271.1–275.5 | |
| 94 | (RS) | 4-methylthiophenyl | bond | | H | 2-methylpropyl | 3,4-dichlorophenyl | | 508 |
| 95 | (RS) | 4-(2,2,2-trifluoro-ethyl) phenyl | bond | | H | 1-methylethyl | 3,4-dichlorophenyl | | 532 |
| 96 | (RS) | 3-cyanophenyl | bond | | H | 2-methylpropyl | 3,4-dichlorophenyl | | 487 |
| 97 | (RS) | 3-aminocarbonyl phenyl | bond | | H | 1-methylethyl | 3,4-dichlorophenyl .2HCl | | 492 | and are named as:
82. 1-{1(R)-[4-(3,4-Dichlorobenzyl)piperazin-1-ylmethyl]-2-methylpropyl}-3-(3-methoxyphenyl)urea.
84. 1-{2(RS)-[4-(3,4-Dichlorobenzyl)piperazin-1-yl]cyclohexyl}-3-(3-methoxyphenyl)urea.
92. 1-{1(RS)-[4-(3,4-Dichlorobenzyl)piperazin-1-ylmethyl]-2-methylpropyl}-3-benzylurea.

V. Representative compounds of Formula (I) where T = nitrogen; U = carbon; m and n = 1;
R = R$^1$ = R$^2$ = R$^3$ = hydrogen; F = bond;
and E = —NHC(O)NH— and other groups are as defined below are:

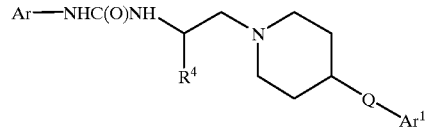

| CPD # | Stereo-chem | Ar | R$^4$ | Q | Ar | M.Pt. | Mass Spec. |
|---|---|---|---|---|---|---|---|
| 98 | (S) | 3-methoxyphenyl | 1-methylethyl | —CH$_2$— | 3,4-dichlorophenyl.HCl | 97.5–99.5 | |
| 99 | (S) | 3-methoxyphenyl | 1,1-dimethylethyl | —CH$_2$— | 3,4-dichlorophenyl | 75.1–80.3 | |
| 100 | (S) | 4-methylphenyl | 1,1-dimethylethyl | —CH$_2$— | 3,4-dichlorophenyl.HCl | 109.5–111 | |
| 101 | (S) | 3-carboxyphenyl | 1,1-dimethylethyl | —CH$_2$— | 3,4-dichlorophenyl | | 506 |
| 102 | (S) | 3-aminocarbonyl phenyl | 1,1-dimethylethyl | —CH$_2$— | 3,4-dichlorophenyl | | 505 |
| 103 | (S) | 3,5-dimethoxy-phenyl | 1-methylethyl | —CH$_2$— | 3,4-dichlorophenyl.HCl | | 508 |
| 104 | (RS) | 3,4-dimethoxy phenyl | 1-methylethyl | —CH$_2$— | 3,4-dichlorophenyl | | 508 |
| 105 | (R) | 3-methoxyphenyl | 1-methylethyl | —CH$_2$— | 3,4-dichlorophenyl | | 478 |
| 106A | (S) | 3-methoxyphenyl | 1,1-dimethylethyl | —CH$_2$— | 3,4-dichlorophenyl.TFA | | 492 |
| 106B | (R) | 3,4,5-trimethoxy-phenyl | 1-methylethyl | —CH$_2$— | 3,4-dichlorophenyl | | |
| 106C | (R) | 3,4,5-trimethoxy-phenyl | 1,1-dimethylethyl | —CH$_2$— | 3,4-dichlorophenyl | | |
| 106D | (R) | 3-methylsulfonyl-aminophenyl | 1-methylethyl | —CH$_2$— | 3,4-dichlorophenyl | | |

V. Representative compounds of Formula (I) where T = nitrogen; U = carbon; m and n = 1;
R = R¹ = R² = R³ = hydrogen; F = bond;
and E = —NHC(O)NH— and other groups are as defined below are:

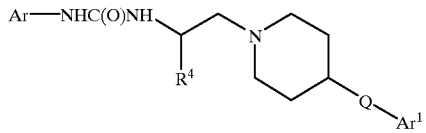

| CPD # | Stereo-chem | Ar | R⁴ | Q | Ar | M.Pt. | Mass Spec. |
|---|---|---|---|---|---|---|---| and are named as:
98. 1-{1(S)-[4-(3,4-Dichlorobenzyl)piperidin-1-ylmethyl]-2-methylpropyl}-3-(3-methoxyphenyl)urea.

VI. Representative compounds of Formula (I) where T and U = nitrogen; m and n = 1;
R = R¹ = R² = R³ = hydrogen;
Q = —CH₂—; E = —NHC(S)NH— and other groups are as defined below are:

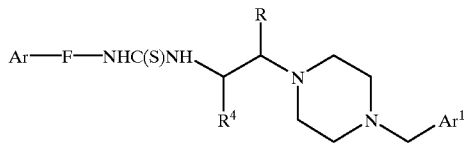

| CPD # | Stereo-chem | Ar | F | R⁴ | Ar¹ | Mass Spec. m/e |
|---|---|---|---|---|---|---|
| 107 | (RS) | 3-methylphenyl | bond | 1-methylethyl | 4-chlorophenyl | 444 |
| 108 | (RS) | 2-fluorophenyl | bond | 1-methylethyl | 3,4-dichlorophenyl | 482 |
| 109 | (RS) | 1-naphthyl | bond | 1-methylethyl | 4-chlorophenyl | 480 |
| 110 | (RS) | 2-methoxyphenyl | bond | 1-methylethyl | 3,4-dichlorophenyl | 494 |
| 111 | (RS) | 3-methylthiophenyl | bond | 1-methylethyl | 3,4-dichlorophenyl | 510 |
| 112 | (RS) | 2,4-difluorophenyl | bond | 2-methylpropyl | 3,4-dichlorophenyl | 514 |
| 113 | (RS) | 4-N,N-dimethylamino-phenyl | bond | 1-methylethyl | 4-chlorophenyl | 473 |
| 114 | (RS) | 4-methoxyphenyl | —CH₂— | 1-methylethyl | 3,4-dichlorophenyl | 508 |
| 115 | (RS) | 4-trifluoromethylphenyl | bond | 1-methylethyl | 4-chlorophenyl | 498 |
| 116 | (RS) | 3-chlorophenyl | bond | 2-methylpropyl | 3,4-dichlorophenyl | 512 | and are named as:
107. 1 - {1 (RS)-[4-(4-Chlorobenzyl)piperazin-1-yl]-2-methylpropyl}-3-(3-methylphenyl)-2-thiourea.
111. 1 - {1 (RS)-[4-(3,4-Dichlorobenzyl)piperazin-1-yl]-3-methylbutyl}-3-(2,4-difluorophenyl)-2-thiourea.

VII. Representative compounds of Formula (I) where T and U = nitrogen; m and n = 1; R = R¹ = R² = R³ = hydrogen; F = bond, Q = —CH₂—; E = —SO₂NH— and other groups are as defined below are:

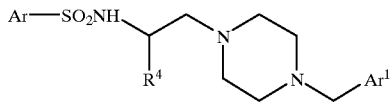

| CPD # | Stereo-chem | Ar | R⁴ | Ar¹ | Mass Spec. m/e |
|---|---|---|---|---|---|
| 117 | (R) | 4-fluorophenyl | 1-methylethyl | 4-dichlorophenyl | 487 |
| 118 | (RS) | 4-chlorophenyl | 1-methylethyl | 4-chlorophenyl | 469 |
| 119 | (R) | 4-nitrophenyl | 1-methylethyl | 3,4-dichlorophenyl | 514 |
| 120 | (R) | thiophen-2-yl | 1-methylethyl | 4-chlorophenyl | 441 |
| 121 | (RS) | 4-trifluorophenyl | 1-methylethyl | 4-chlorophenyl | 503 |
| 122 | (RS) | 2,4-dichlorophenyl | 2-methylpropyl | 3,4-dichlorophenyl | 511 |
| 123 | (RS) | 3-bromophenyl | 2-methylpropyl | 3,4-dichlorophenyl | 561 |
| 124 | (R) | 4-methylphenyl | 1-methylethyl | 4-chlorophenyl | 449 |
| 125 | (R) | 2-chloro-4-fluoro-phenyl | 1-methylethyl | 4-chlorophenyl | 487 |
| 126 | (R) | 2-nitro-4-trifluoro-methylphenyl | 1-methylethyl (M + —CF₃) | 4-chlorophenyl | 480 |
| 127 | (RS) | 3,4-dimethoxyphenyl | 1-methylethyl | 4-chlorophenyl | 495 | and are named as:
117. N-{1(R)-[4-(3,4-Dichlorobenzyl)piperazin-1-yl-methyl]-2-methylpropyl}-4-fluorobenzenesulfonamide.
120. N-{1(RS)-[4-(3,4-Dichlorobenzyl)piperazin-1-yl-methyl]-3-methylbutyl}-2,4-dichlorobenzenesulfonamide.

VIII. Representative compounds of Formula (1) where T and U = nitrogen; m and n = 1; R¹ = R² = R³ = hydrogen; F = bond; Q = —CH₂—; E = —NHC(O)— and other groups are as defined below are:

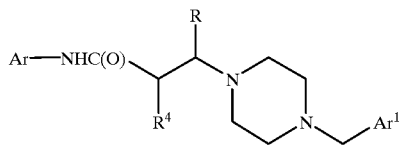

| CPD # | Stereo-chem | Ar | R + R⁴ | R⁴ | R | Ar¹ | M.Pt. | Mass Spec. m/e |
|---|---|---|---|---|---|---|---|---|
| 128 | (RS) | 4-methylphenyl | | methyl | H | 3,4-dichlorophenyl.2HCl | 256.2–256.7 | |
| 129 | (RS) | phenyl | | methyl | H | 3,4-dichlorophenyl.2HCl | 262.5–262.9 | |
| 130 | 1(R),2(R) | 4-methylphenyl | cyclopentyl | | | 3,4-dichlorophenyl.2HCl | 446 | |
| 131 | 1(R),2(S) | 4-methylphenyl | cyclopentyl | | | 3,4-dichlorophenyl | | | and are named as:
128. 2-(RS)-[4-(3,4-Dichlorobenzyl)piperazin-1-ylmethyl]-N-(4-methylphenyl)propionamide dihydrochloride salt.
130. 2-(R)-[4-(3,4-Dichlorobenzyl)piperazin-1-ylmethyl]-N-(4-methylphenyl)cyclopentane 1-(R)-carboxamide dihydrochloride salt.

IX. Representative compounds of Formula (I) where T = carbon, U = nitrogen; n = 1; R= R¹ = R² = R³ = hydrogen; F = bond; and Q = —CH₂—; E = —C(O)NH— and other groups are as defined below are

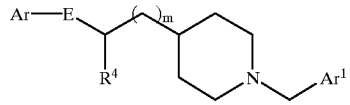

| CPD # | Stereo-chem | Ar | E | R⁴ | m | R | Ar¹ | M.Pt. |
|---|---|---|---|---|---|---|---|---|
| 132 | (RS) | 4-methoxyphenyl | —NHC(O)NH— | 1-methylethyl | 0 | H | 3,4-dichlorophenyl | 161.4–161.8 |
| 133 | (RS) | 4-methylphenyl | —C(O)NH— | 1-methylethyl | 1 | H | 3,4-dichlorophenyl | 233.9–235.5 | and are named as:
133. NL {1-[1(RS)-[1-(3,4-Dichlorobenzyl)piperidin-4-ylmethyl]-2-methylpropyl}-4-methylbenzamide.

X. Representative compounds of Formula (I) where T = —N⁺R¹⁰ —, U = carbon, m = 1, R = R¹ = R² = R³ = hydrogen; F = bond; Q = —CH₂—; E = —C(O)NH— and other groups are as defined below are:

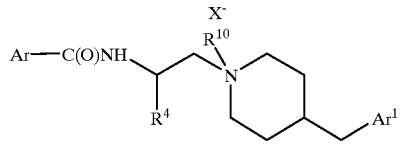

| CPD # | Stereo-chem | Ar | R⁴ | R¹⁰ | X | Ar¹ | Mass Spec. m/e |
|---|---|---|---|---|---|---|---|
| 134 | (R) | 4-methylphenyl | 1-methylethyl | methyl | Cl | 3,4-dichlorophenyl | 461 |
| 135 | (R) | 4-methylphenyl | 1-methylethyl | methyl | TFA | 3,4-dichlorophenyl | 461 |
| 136 | (R) | 4-[2-(t-butoxy-carbonylamino)-ethyl)]phenyl | 1-methylethyl | ethyl | I | 3,4-dichlorophenyl | 604 |
| 137 | (R) | 4-(2-aminoethyl)-phenyl | 1-methylethyl | methyl | Cl | 3,4-dichlorophenyl .HCl | 490 |
| 138 | (S) | 4-methylphenyl | 1-methylethyl | methyl | Cl | 3,4-dichlorophenyl | 461 |
| 139 | (R) | 4-(2-aminoethyl)-phenyl | 1-methylethyl | ethyl | Cl | 3,4-dichlorophenyl .HCl | 504 |
| 140 | (S) | 4-[2-(t-butoxy-carbonylamino)-ethyl)]phenyl | 1-methylethyl | ethyl | I | 3,4-dichlorophenyl | 604 |
| 141 | (S) | 4-(2-aminoethyl)-phenyl | 1-methylethyl | ethyl | Cl | 3,4-dichlorophenyl .HCl | 504 |
| 142 | (S) | 4-(2-aminoethyl)-phenyl | 1-methylethyl | methyl | Cl | 3,4-dichlorophenyl . HCl | 490 |

XI. Representative compounds of Formula (I) where T = carbon; U = —N⁺R¹⁰ —; m = 0; R = R¹ = R² = R³ = R⁴ = hydrogen; F = bond, Q = —CH₂—; E = —C(O)NH— and other groups are as defined below are:

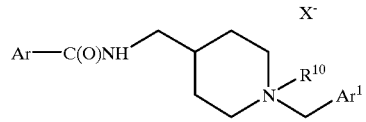

| CPD # | Stereo-chem | Ar | R¹⁰ | X | Ar¹ | Mass Spec. m/e |
|---|---|---|---|---|---|---|
| 143 | (RS) | 4-amino-5-chloro-2- | methyl | I | 3,4-dichlorophenyl | 470 |

-continued

XI. Representative compounds of Formula (I) where T = carbon; U = —N⁺R¹⁰—; m = 0; R = R¹ = R² = R³ = R⁴ = hydrogen; F = bond, Q = —CH₂—; E = —C(O)NH— and other groups are as defined below are:

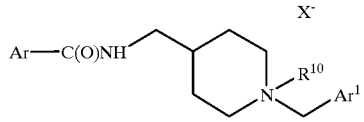

| CPD # | Stereo-chem | Ar | R¹⁰ | X | Ar¹ | Mass Spec. m/e |
|---|---|---|---|---|---|---|
| | | methoxyphenyl | | | | |

XII. Representative compounds of Formula (I) where T = —N⁺R¹⁰—; U = carbon; m = 1; R = R¹ = R² = R³ = hydrogen; F = bond; Q= —CH₂—; E = —NHC(O)NH— and other groups are as defined below are:

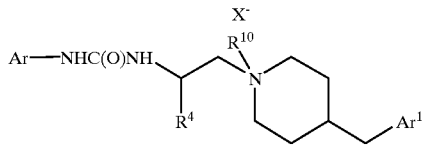

| CPD # | Stereo-chem | Ar | R⁴ | R¹⁰ | X | Ar¹ | Mass Spec. m/e |
|---|---|---|---|---|---|---|---|
| 144 | (R) | 3,4,5-trimethoxyphenyl | 1-methylethyl | ethyl | I | 3,4-dichlorophenyl | 566 |
| 145 | (R) | 3-methoxyphenyl | 1-methylethyl | ethyl | I | 3,4-dichlorophenyl | 506 |
| 146 | (R) | 3,5-dimethoxyphenyl | 1-methylethyl | ethyl | I | 3,4-dichlorophenyl | 536 |
| 147 | (R) | 3-acetylphenyl | 1,1-dimethylethyl | ethyl | I | 3,4-dichlorophenyl | |
| 148 | (R) | 3,5-dimethoxyphenyl | 1,1-dimethylethyl | ethyl | I | 3,4-dichlorophenyl | |
| 149 | (R) | 3-acetylphenyl | 1-methylethyl | ethyl | I. | 3,4-dichlorophenyl | 520 |
| 150 | (R) | 3-methoxyphenyl | 1,1-dimethylethyl | ethyl | I | 3,4-dichlorophenyl | |
| 151 | (R) | 3-methoxycarbonyl phenyl | 1-methylethyl | ethyl | I | 3,4-dichlorophenyl | 534 |
| 152 | (R) | 2,5-dimethoxyphenyl | 1,1-dimethylethyl | ethyl | I | 3,4-dichlorophenyl | |
| 153 | (R) | 2,3,4-trimethoxyphenyl | 1-methylethyl | ethyl | I | 3,4-dichlorophenyl | 566 |
| 154 | (R) | 3-carboxyphenyl | 1-methylethyl | ethyl | I | 3,4-dichlorophenyl | 520 |
| 155 | (R) | 2-ethylphenyl | 1,1-dimethylethyl | ethyl | I | 3,4-dichlorophenyl | |
| 156 | (S) | 3-methoxyphenyl | 1-methylethyl | ethyl | I | 3,4-dichlorophenyl | 506 |
| 157 | (R) | 3,4,5-trimethoxyphenyl | 1-methylethyl | methyl | I | 3,4-dichlorophenyl | |
| 158 | (R) | 3-methoxyphenyl | 1-methylethyl | methyl | I | 3,4-dichlorophenyl | |
| 159 | (R) | 3,4,5-trimethoxyphenyl | 1-methylethyl | 2-hydroxyethyl | Cl | 3,4-dichlorophenyl | |
| 160 | (R) | 3,4,5-trimethoxyphenyl | 1-methylethyl | ethoxycarbonyl methyl | I | 3,4-dichlorophenyl | |

PREFERRED EMBODIMENTS

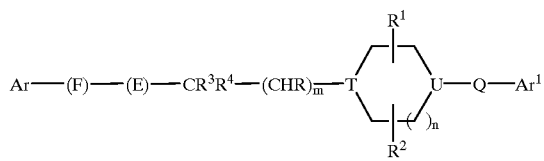

(I)

While the broadest definition of this invention is set forth in the Summary of the Invention, certain compounds of Formula (I) are preferred.

(I) A preferred group of compounds is that wherein:
T and U are nitrogen or one of T or U is nitrogen and the other is carbon;
n is 1;

m is 0 or 1;

F is a bond;

Q is an alkylene chain of between 1 to 6 carbon atoms inclusive, more preferably methylene; and E is —C(O)N($R^5$)—, —$SO_2$N($R^5$)—, —N($R^6$)C(O)N ($R^5$)— or —N($R^6$)C(O)—.

Within the above preferred group (I) a more preferred group of compounds is that wherein:

R, $R^1$, $R^2$ and $R^3$ are hydrogen; and

E is —C(O)N($R^5$)—, preferably —C(O)NH—.

Another more preferred group of compounds is wherein:

R, $R^1$, $R^2$ and $R^3$ are hydrogen; and

E is —N($R^6$)C(O)N($R^5$)—, preferably —NHC(O)NH—.

Within these preferred and more preferred groups of compounds a particularly preferred group of compounds is that wherein T and U are nitrogen;

Another particularly preferred group of compounds is that wherein T is nitrogen and U is carbon;

Yet another particularly preferred group of compounds is that wherein T is carbon and U is nitrogen;

Within the above preferred, more preferred and particularly preferred groups where T and U are both nitrogen or where T is nitrogen and U is carbon, most preferred compounds are those wherein:

$R^4$ is alkyl or heteroalkyl, preferably 1-methylethyl, 1,1-dimethylethyl, 2-methylpropyl, 3-hydroxypropyl, 1-hydroxyethyl or 2-hydroxyethyl, more preferably 1-methylethyl or 1,1-dimethylethyl;

Ar is a heteroaryl or aryl ring, preferably a pyridin-2-yl, pyridin-3-yl, quinolin-3-yl or 5-methylthiophen-2-yl ring or a phenyl ring optionally substituted with one, two or three substituents selected from alkyl, heteroalkyl, alkoxy, —COR (where R is alkyl), —$SO_2$R (where R is alkyl, amino or mono or disubstituted amino), methylenedioxy, hydroxy, halo, acylamino, amino, mono- or disubstituted amino, —CONR'R", -(alkylene)-CONR'R" (where R' and R" are hydrogen or alkyl), —COOR, -(alkylene)-COOR (where R is hydrogen or alkyl) or —NR$SO_2$R' (where R is hydrogen or alkyl and R' is alkyl, amino, mono or disubstituted amino), more preferably a phenyl ring optionally substituted with one, two or three substituents selected from methyl, methoxy, fluoro, chloro, dimethylamino, acetyl, hydroxy, amino, methylenedioxy, —$SO_2$Me, 2-acetylaminoethyl, 2-[(R)-amino-3-methylbutyrylamino]ethyl, 2-aminoethyl, aminomethyl, hydroxymethyl, aminocarbonyl, —COOH, carboxymethyl, methoxycarbonylmethyl, aminocarbonylmethyl, dimethylaminocarbonylmethyl, acetylaminomethyl, methylsulfonylamino, methylsulfonylaminomethyl, dimethylaminosulfonylaminomethyl, or dimethylamino, most preferably phenyl, 4-chlorophenyl, 3,4-difluorophenyl, 4-methylphenyl, 3-methoxyphenyl, 4-methoxyphenyl, 4-hydroxyphenyl, 3,4-methylenedioxyphenyl, 4-methylsulfonylphenyl, 4-[(2-acetylamino)ethyl]phenyl, 4-{2-[(R)-amino-3-methylbutyrylamino]ethyl}phenyl, 4-(2-aminoethyl)phenyl, 4-(aminomethyl)phenyl, 4-(hydroxymethyl)phenyl, 3-aminocarbonylphenyl, 3-carboxyphenyl, 2,5-dimethoxyphenyl, 3,5-dimethoxyphenyl, 3,4-dimethoxyphenyl, 3,4,5-trimethoxyphenyl, 3-aminocarbonylmethyl-phenyl, 3-acetylaminomethyphenyl, 3-carboxymethylphenyl, 3-methylsulfonylaminophenyl, 3-methylsulfonylaminomethylphenyl or 4-aminophenyl; and $Ar^1$ is a heteroaryl or aryl ring, preferably 1-acetylindol-3-yl, 3-methylbenzo-thiophen-2-yl or 5-nitrothiophen-3-yl, or a phenyl ring optionally substituted with one, two or three substituent selected from alkyl, heteroalkyl, alkoxy, halo, trifluoromethyl, nitro, or mono- or disubstituted amino, more preferably a phenyl ring substituted with one, or two substituents selected from methyl, methoxy, chloro, fluoro, trifluoromethyl or nitro, most preferably 4-nitrophenyl, 4-trifluoromethylphenyl, 4-chlorophenyl, 3,4-difluorophenyl, 2,3-dichlorophenyl, 3-methyl-4-nitrophenyl, 3-chloro-4-fluorophenyl or 3,4-dichlorophenyl.

Within the above preferred, more preferred and particularly preferred groups where T is carbon and U is nitrogen, most preferred compounds are those wherein:

$R^4$ is alkyl or heteroalkyl, preferably methyl, 1-methylethyl, 1,1-dimethylethyl, 2-methylpropyl, 3-hydroxypropyl, 1-hydroxyethyl or 2-hydroxyethyl.

Ar is a heteroaryl or aryl ring, preferably a pyridin-2-yl, pyridin-3-yl, quinolin-3yl or 5-methylthiophen-2-yl ring or a phenyl ring optionally substituted with one, two or three substituents selected from alkyl, heteroalkyl, alkoxy, —COR (where R is alkyl), —$SO_2$R (where R is alkyl, amino or mono or disubstituted amino), methylenedioxy, hydroxy, halo, acylamino, amino, mono- or disubstituted amino, —CONR'R", -(alkylene)-CONR'R" (where R' and R" are hydrogen or alkyl), —COOR, -(alkylene)-COOR (where R is hydrogen or alkyl) or —NR$SO_2$R' (where R is hydrogen or alkyl and R' is alkyl, amino, mono or disubstituted amino), more preferably a phenyl ring optionally substituted with one, two or three substituents selected from methyl, methoxy, fluoro, chloro, dimethylamino, acetyl, hydroxy, amino, methylenedioxy, —$SO_2$Me, 2-acetylaminoethyl, 2-[(R)-amino-3-methylbutyrylamino]ethyl, 2-aminoethyl, aminomethyl, hydroxymethyl, aminocarbonyl, —COOH, carboxymethyl, methoxycarbonylmethyl, aminocarbonylmethyl, dimethylaminocarbonylmethyl, acetylaminomethyl, methylsulfonylamino, methylsulfonylaminomethyl, dimethylaminosulfonylaminomethyl, or dimethylamino, most preferably phenyl, 4-chlorophenyl, 3,4-difluorophenyl, 4-methylphenyl, 3-methoxyphenyl, 4-methoxyphenyl, 4-hydroxyphenyl, 3,4-methylenedioxy-phenyl, 4-methylsulfonylphenyl, 4-[(2-acetylamino)ethyl]phenyl, 4-{2-[(R)-amino-3-methylbutyrylamino]ethyl}phenyl, 4-(2-aminoethyl)phenyl, 4-(aminomethyl)phenyl, 4-(hydroxymethyl)phenyl, 3-aminocarbonylphenyl, 3-carboxyphenyl, 2,5-dimethoxyphenyl, 3,5-dimethoxyphenyl, 3,4-dimethoxyphenyl, 3,4,5-trimethoxyphenyl, 3-aminocarbonyl-methylphenyl, 3-acetylaminomethyphenyl, 3-carboxymethylphenyl, 3-methylsulfonyl-aminophenyl, 3-methylsulfonylaminomethylphenyl or 4-aminophenyl; and $Ar^1$ is a heteroaryl or aryl ring, preferably 1-acetylindol-3-yl, 3-methylbenzo-thiophen-2-yl, 5-nitrothiophen-3-yl or a phenyl ring optionally substituted with one, two or three substituent selected from alkyl, heteroalkyl, alkoxy, halo, trifluoromethyl, nitro, or mono- or disubstituted amino, more preferably a phenyl ring substituted with one, or two substituents selected from methyl, methoxy, chloro, fluoro, trifluoromethyl or nitro, most preferably 4-nitrophenyl, 4-trifluoromethylphenyl, 4-chlorophenyl, 3,4- difluorophenyl, 2,3-dichlorophenyl, 3-methyl-4-nitrophenyl, 3-chloro-4-fluorophenyl or 3,4-dichlorophenyl.

(II) Another preferred group of compounds is that wherein:

T is —N$^+$R$^{10}$— wherein R$^{10}$ is alkyl, hydroxyalkyl, alkoxycarbonylalkyl, preferably methyl, ethyl, 2-hydroxyethyl, 3-hydroxypropyl, methoxycarbonylmethyl, ethoxycarbonylmethyl, most preferably methyl, ethyl, or 2-hydroxyethyl;

m is 1;

R, R$^1$, R$^2$ and R$^3$ are hydrogen;

F is a bond;

Q is an alkylene chain, more preferably methylene or ethylene, most preferably methylene.

Within this group (II) a more preferred group of compounds is that wherein: (A) E is —C(O)NH—; and R$^4$ is alkyl or heteroalkyl, preferably 1-methylethyl, 1,1-dimethylethyl, 2-methylpropyl, 3-hydroxypropyl, 1-hydroxyethyl or 2-hydroxyethyl, more preferably 1-methylethyl or 1,1-dimethylethyl.

Within the preferred and more preferred groups, an even more preferred group of compounds is that wherein:

The stereochemistry at the carbon atom to which the R$^3$ and R$^4$ groups are attached is (R);

Ar is a heteroaryl or aryl ring, preferably a pyridin-2-yl, pyridin-3-yl, quinolin-3-yl or 5-methylthiophen-2-yl ring or a phenyl ring optionally substituted with one, two or three substituents selected from alkyl, heteroalkyl, alkoxy, —COR (where R is alkyl), —SO$_2$R (where R is alkyl, amino or mono or disubstituted amino), methylenedioxy, hydroxy, halo, acylamino, amino, mono- or disubstituted amino, —CONR'R", -(alkylene)-CONR'R" (where R' and R" are hydrogen or alkyl), —COOR, -(alkylene)-COOR (where R is hydrogen or alkyl) or —NRSO$_2$R' (where R is hydrogen or alkyl and R' is alkyl, amino, mono or disubstituted amino), more preferably a phenyl ring optionally substituted with one, two or three substituents selected from methyl, methoxy, fluoro, chloro, dimethylamino, acetyl, hydroxy, amino, methylenedioxy, —SO$_2$Me, 2-acetylaminoethyl, 2-[(R)-amino-3-methylbutyrylamino]ethyl, 2-aminoethyl, aminomethyl, hydroxymethyl, aminocarbonyl, dimethylaminocarbonyl, —COOH, carboxymethyl, methoxycarbonylmethyl, aminocarbonylmethyl, dimethylaminocarbonylmethyl, acetylaminomethyl, methylsulfonylamino, methylsulfonylaminomethyl, dimethylaminosulfonylaminomethyl, or dimethylamino, most preferably phenyl, 4-chlorophenyl, 3,4-difluorophenyl, 4-methylphenyl, 4-methoxyphenyl, 4-hydroxyphenyl, 4-dimethylamino-phenyl, 4-aminocarbonylphenyl, 4-acetylphenyl, 4-acetylaminophenyl, 3,4-methylenedioxyphenyl, 4-methylsulfonylphenyl, 4-[(2-acetylamino)ethyl]phenyl, 4-{2-[(R)-amino-3-methylbutyrylamino]ethyl}phenyl, 4-(2-aminoethyl) phenyl, 4-(aminomethyl)phenyl, 4-(hydroxymethyl) phenyl, 2,5-dimethoxyphenyl, 3,5-dimethoxyphenyl, 3,4-dimethoxyphenyl, 3,4,5-trimethoxyphenyl, 4-aminocarbonylmethylphenyl, 4-acetylaminomethyphenyl, 4-methylsulfonylaminophenyl, 4-methylsulfonylaminomethylphenyl or 4-aminophenyl; and Ar$^1$ is a heteroaryl or aryl ring, preferably 1-acetylindol-3-yl, 3-methylbenzo-thiophen-2-yl, 5-nitrothiophen-3-yl or a phenyl ring optionally substituted with one, two or three substituent selected from alkyl, heteroalkyl, alkoxy, halo, trifluoromethyl, nitro, or mono- or disubstituted amino, more preferably a phenyl ring substituted with one, or two substituents selected from methyl, methoxy, chloro, fluoro, trifluoromethyl or nitro, most preferably 4-nitrophenyl, 4-trifluoromethylphenyl, 4-chlorophenyl, 3,4-difluorophenyl, 2,3-dichlorophenyl, 3-methyl-4-nitrophenyl, 3-chloro-4-fluorophenyl or 3,4-dichlorophenyl.

(B) Another more preferred group of compounds within group (II) is that wherein:

E is —NHC(O)NH—; and

R$^4$ is alkyl or heteroalkyl, preferably 1-methylethyl, 1,1-dimethylethyl, 2-methylpropyl, 3-hydroxypropyl, 1-hydroxyethyl or 2-hydroxyethyl, more preferably 1-methylethyl or 1,1-dimethylethyl.

Within the preferred and more preferred groups in group (II), an even more preferred group of compounds is that wherein:

The stereochemistry at the carbon atom to which the R$^3$ and R$^4$ groups are attached is (R);

Ar is a heteroaryl or aryl ring, preferably a pyridin-2-yl, pyridin-3-yl, quinolin-3-yl or 5-methylthiophen-2-yl ring or a phenyl ring optionally substituted with one, two or three substituents selected from alkyl, heteroalkyl, alkoxy, —COR (where R is alkyl), —SO$_2$R (where R is alkyl, amino or mono or disubstituted amino), methylenedioxy, hydroxy, halo, acylamino, amino, mono- or disubstituted amino, —CONR'R", -(alkylene)-CONR'R" (where R' and R" are hydrogen or alkyl), —COOR, -(alkylene)-COOR (where R is hydrogen or alkyl) or —NRSO$_2$R' (where R is hydrogen or alkyl and R' is alkyl, amino, mono or disubstituted amino), more preferably a phenyl ring optionally substituted with one, two or three substituents selected from methyl, methoxy, fluoro, chloro, dimethylamino, acetyl, acetylamino, hydroxy, amino, methylenedioxy, —SO$_2$Me, 2-acetylaminoethyl, 2-[(R)-amino-3-methylbutyrylamino]ethyl, 2-aminoethyl, aminomethyl, hydroxymethyl, aminocarbonyl, dimethylaminocarbonyl, —COOH, carboxymethyl, methoxycarbonylmethyl, aminocarbonylmethyl, dimethylaminocarbonylmethyl, acetylaminomethyl, methylsulfonylamino, methylsulfonylaminomethyl, dimethylaminosulfonylaminomethyl, or dimethylamino, most preferably phenyl, 3-methoxyphenyl, 3-methylsulfonylphenyl, 3-dimethylaminophenyl, 3-acetylaminophenyl, 3-acetylphenyl, 3-[(2-acetylamino)ethyl]phenyl, 3-aminocarbonylphenyl, 3-carboxyphenyl, 2,5-dimethoxyphenyl, 3,5-dimethoxy-phenyl, 3,4-dimethoxyphenyl, 3,4,5-trimethoxyphenyl, 3-aminocarbonylmethylphenyl, 3-acetylaminomethyphenyl, 3-carboxymethylphenyl, 3-methylsulfonylaminophenyl, 3-methylsulfonylamino-methylphenyl or 3-aminophenyl; and Ar$^1$ is a heteroaryl or aryl ring, preferably 1-acetylindol-3-yl, 3-methylbenzo-thiophen-2-yl, 5-nitrothiophen-3-yl or a phenyl ring optionally substituted with one, two or three substituent selected from alkyl, heteroalkyl, alkoxy, halo, trifluoromethyl, nitro, or mono- or disubstituted amino, more preferably a phenyl ring substituted with one, or two substituents selected from methyl, methoxy, chloro, fluoro, trifluoromethyl or nitro, most preferably 4-nitrophenyl, 4-trifluoromethylphenyl, 4-chlorophenyl, 3,4-difluorophenyl, 2,3-dichlorophenyl, 3-methyl-4-nitrophenyl, 3-chloro-4-fluorophenyl or 3,4-dichlorophenyl.

(III) A third preferred group of compounds is that wherein:
$R^4$ is alkyl or heteroalkyl, preferably 1-methylethyl, 1,1-dimethylethyl, 2-methylpropyl, 3-hydroxypropyl, 1-hydroxyethyl or 2-hydroxyethyl, more preferably 1-methylethyl or 1,1-dimethylethyl.

(IV) A fourth preferred group of compounds is that wherein:
E is —C(O)N($R^6$)— or —N($R^7$)C(O)N($R^6$)—, preferably —C(O)NH— or —NHC(O)NH—.

Exemplary Particularly Preferred Compounds of the Invention at Present are

N-{1-(S)-[4-(3,4-Dichlorobenzyl)piperazin-1-ylmethyl]-2-methylpropyl}-4-methylbenzamide dihydrochloride salt.

N-{1-(S)-[4-(3,4-Dichlorobenzyl)piperazin-1-ylmethyl]-2,2-dimethylpropyl}-4-methylbenzamide dihydrochloride salt.

1-{1-(R)-[4-(3,4-Dichlorobenzyl)piperazin-1-ylmethyl]-2-methylpropyl}-3-(3-methoxyphenyl)urea.

N-{1-(RS)-[4-(3,4-Dichlorobenzyl)piperazin-1-ylmethyl]-2-methylpropyl}-3,4-methylenedioxybenzamide.

N-{1-(S)-[4-(3,4-Dichlorobenzyl)piperazin-1-ylmethyl]-2,2-dimethylpropyl}-4-methylsulfonylbenzamide dihydrochloride salt.

N-{1-(S)-[4-(3,4-Dichlorobenzyl)piperazin-1-ylmethyl]-2,2-dimethylpropyl}-4-acetylbenzamide dihydrochloride salt.

N-{1-(S)-[4-(3,4-Dichlorobenzyl)piperazin-1-ylmethyl]-2,2-dimethylpropyl}-4-dimethylaminobenzamide dihydrochloride salt.

N-{1-(S)-[4-(4-Nitrobenzyl)piperidin-1-ylmethyl]-2,2-dimethylpropyl}-4-methylsulfonylbenzamide hydrochloride salt.

N-{1-(S)-[4-(3,4-Dichlorobenzyl)piperazin-1-ylmethyl]-2,2-dimethylpropyl}-5-methylthiophene-2-carboxamide dihydrochloride salt.

N-{1-(RS)-[4-(3,4-Dichlorobenzyl)piperazin-1-ylmethyl]-2,2-dimethylpropyl}-4-methoxybenzamide.

N-{1-(RS)-[4-(3,4-Dichlorobenzyl)piperazin-1-ylmethyl]-2,2-dimethylpropyl}-3-cyanobenzamide.

N-{1-(RS)-[4-(3,4-Dichlorobenzyl)piperazin-1-ylmethyl]-2-methylpropyl}-3,4-difluorobenzamide.

N-{1(-RS)-[3-Methyl-4-(3,4-dichlorobenzyl)piperazin-1-ylmethyl]-2-methyl-propyl}-4-methylbenzamide dihydrochloride salt.

N-{4-(R)-[4-(3,4-Dichlorobenzyl)piperidin-1-ylmethyl]-2-methylpropyl}-1-[4-(2-acetylaminoethyl)]benzamide dihydrochloride salt.

4-[2-(2-(R)-Amino-3-methylbutyrylamino)ethyl]-N-{1-[4-(3,4-dichlorobenzyl)piperidin-1-ylmethyl]-2-methylpropyl}benzamide dihydrochloride salt.

N-{4-(R)-[4-(3,4-Dichlorobenzyl)piperidin-1-ylmethyl]-2,2-dimethylpropyl}-1-[4-(2-aminoethyl)]benzamide dihydrochloride salt.

N-{4-(R)-[4-(3,4-Dichlorobenzyl)piperidin-1-ylmethyl]-2,2-dimethylpropyl}-1-(4-aminomethyl)benzamide dihydrochloride salt.

N-{4-(S)-[4-(3,4-Dichlorobenzyl)piperidin-1-ylmethyl]-2,2-dimethylpropyl}-1-(3,4-methylenedioxy)benzamide dihydrochloride salt.

1-{1-(RS)-[4-(3,4-Dichlorobenzyl)piperazin-1-ylmethyl]-2-methylpropyl}-3-(3-aminocarbonylphenyl)urea.

N-{4-(R)-[4-(3,4-Dichlorobenzyl)piperidin-1-ylmethyl]-2,2-dimethylpropyl}-1-quinoline-3-carboxamide hydrochloride salt.

1-{1-(S)-[4-(3,4-Dichlorobenzyl)piperidin-1-ylmethyl]-2,2-dimethylpropyl}-3-(3-carboxyphenyl)urea.

1-{1-(S)-[4-(3,4-Dichlorobenzyl)piperidin-1-ylmethyl]-2,2-dimethylpropyl}-3-(3-aminocarbonylphenyl)urea.

1-{1-(S)-[4-(3,4-Dichlorobenzyl)piperidin-1-ylmethyl]-2-methylpropyl}-3-(3-methylsulfonylphenyl)urea.

1-{1-(R)-[4-(3,4-Dichlorobenzyl)piperidin-1-ylmethyl]-2-methylpropyl}-3-(3,5-dimethoxyphenyl)urea hydrochloride salt.

1-{1-(R)-[4-(3,4-Dichlorobenzyl)piperidin-1-ylmethyl]-2-methylpropyl}-3-(3,4-dimethoxyphenyl)urea.

N-{1-(S)-[4-(4-Chlorobenzyl)piperazin-1-ylmethyl]-2-methylpropyl}-4-methylbenzamide.

N-{1-(S)-[4-(3,4-Dichlorobenzyl)piperazin-1-ylmethyl]-2-methylpropyl}-4-guanidinomethylbenzamide.

N-{1-(RS)-[4-(4-Nitrobenzyl)piperazin-1-ylmethyl]-2-methylpropyl}-4-methylbenzamide.

N-{1-(RS)-[4-(3,4-Difluorobenzyl)piperazin-1-ylmethyl]-2-methylpropyl}-4-methylbenzamide.

N-{1-(RS)-[4-(3,4-Dichlorobenzyl)piperazin-1-ylmethyl]-2,2-dimethylpropyl}-4-methylbenzamide.

N-{1-(RS)-[4-(2,3-Dichlorobenzyl)piperazin-1-ylmethyl]-2-methylpropyl}-4-methylbenzamide.

N-{1-(RS)-[4-(3-Methyl-4-nitrobenzyl)piperazin-1-ylmethyl]-2-methylpropyl}-4-methylbenzamide.

N-{1-(RS)-[4-(3-Chloro-4-fluorobenzyl)piperazin-1-ylmethyl]-2-methylpropyl}-4-methylbenzamide.

N-{1-(R)-[4-(3-Chloro-4-fluorobenzyl)piperazin-1-ylmethyl]-2,2-dimethyl-propyl}-4-methylbenzamide.

N-{1-(R)-[4-(3-Methylbenzothiophen-2-ylmethyl)piperazin-1-ylmethyl]-2,2-dimethylpropyl}-4-methylbenzamide.

N-{1-(R)-[4-(1-Acetylindol-3-ylmethyl)piperazin-1-ylmethyl]-2,2-dimethyl-propyl}-4-methylbenzamide.

N-{1-(R)-[4-(5-Nitrothiophen-3-ylmethyl)piperazin-1-ylmethyl]-2,2-dimethyl-propyl}-4-methylbenzamide.

N-{1-(R)-[4-(4-Nitrobenzyl)piperazin-1-ylmethyl]-2-methylpropyl}-4-methylbenzamide.

N-{4-(R)-[4-(4-Nitrobenzyl)piperidin-1-ylmethyl]-2,2-dimethylpropyl}-1-pyridine-2-carboxamide hydrochloride salt.

N-{4-(R)-[4-(4-Nitrobenzyl)piperidin-1-ylmethyl]-2,2-dimethylpropyl}-1-pyridine-2-carboxamide.

N-{4-(R)-[4-(3,4-Dichlorobenzyl)piperazin-1-ylmethyl]-2,2-dimethylpropyl}-1-quinoline-3-carboxamide.

1-{1-(R)-[4-(3,4-Dichlorobenzyl)piperazin-1-ylmethyl]-2-methylpropyl}-3-(3-methoxyphenyl)urea.

N-{4-(R)-[4-(3,4-Dichlorobenzyl)piperidin-1-ylmethyl]-2-methylpropyl}-1-(3-methyl)thiophene-2-carboxamide hydrochloride salt.

N-{4-(R)-[4-(3,4-Dichlorobenzyl)piperidin-1-ylmethyl]-2-methylpropyl}-1-[4-(2-aminoethyl)]benzamide dihydrochloride salt.

N-{4-(RS)-[4-(3,4-Dichlorobenzyl)piperidin-1-ylmethyl]-2-methylpropyl}-1-(4-methyl)benzamide.

N-{4-(R)-[4-(3,4-Dichlorobenzyl)piperidin-1-ylmethyl]-2,2-dimethylpropyl}-1-(4-methyl)benzamide hydrochloride salt.

N-{4-(R)-[4-(3,4-Dichlorobenzyl)piperidin-1-ylmethyl]-2,2-dimethylpropyl}-1-(4-methylsulfonyl)benzamide.

N-{4-(S)-[4-(3,4-Dichlorobenzyl)piperidin-1-ylmethyl]-2,2-dimethylpropyl}-1-(5-methylthiophene-2-carboxamide hydrochloride salt.

N-{4-(R)-[4-(3,4-Dichlorobenzyl)piperidin-1-ylmethyl]-2,2-dimethylpropyl}-1-(4-hydroxymethyl)benzamide.

1-{1-(R)-[4-(3,4-Dichlorobenzyl)piperidin-1-ylmethyl]-2,2-dimethylpropyl}-3-(3-methoxyphenyl)urea trifluoroacetate salt.

1-{1-(R)-[4-(3,4-Dichlorobenzyl)piperidin-1-ylmethyl]-2-methylpropyl}-3-(3,4,5-trimethoxyphenyl)urea.

1-{1-(R)-[4-(3,4-Dichlorobenzyl)piperidin-1-ylmethyl]-2,2-dimethylpropyl}-3-(3,4,5-trimethoxyphenyl)urea.

1-{1-(R)-[4-(3,4-Dichlorobenzyl)piperidin-1-ylmethyl]-2-methylpropyl}-3-(3-methylsulfonylaminophenyl)urea.

1-{1-(R)-[4-(3,4-Dichlorobenzyl)piperidin-1-ylmethyl]-2-methylpropyl}-3-(3-methylsulfonylaminomethylphenyl)urea.

1-{1-(R)-[4-(3,4-Dichlorobenzyl)piperidin-1-ylmethyl]-2-methylpropyl}-3-(3-acetylaminophenyl)urea.

1-{1-(R)-[4-(3,4-Dichlorobenzyl)piperidin-1-ylmethyl]-2-methylpropyl}-3-(3-acetylaminomethylphenyl)urea.

1-{1-(R)-[4-(3,4-Dichlorobenzyl)piperidin-1-ylmethyl]-2-methylpropyl}-3-(3-N-methylsulfonyl-N-methylaminophenyl)urea.

1-{1-(R)-[4-(3,4-Dichlorobenzyl)piperidin-1-ylmethyl]-2-methylpropyl}-3-(3-dimethylaminosulfonylaminophenyl)urea.

1-{1-(R)-[4-(3,4-Dichlorobenzyl)piperidin-1-ylmethyl]-2-methylpropyl}-3-(3-dimethylaminosulfonylaminomethylphenyl)urea.

1-{1-(R)-[4-(3,4-Dichlorobenzyl)piperidin-1-ylmethyl]-2-methylpropyl}-(3-methoxyphenyl)-3-methylurea.

1-{1-(R)-[4-(3,4-Dichlorobenzyl)piperidin-1-ylmethyl]-2-methylpropyl}-3-(3-acetylphenyl)urea.

1-{1-(R)-[4-(3,4-Dichlorobenzyl)piperidin-1-ylmethyl]-2-methylpropyl}-3-(3-aminomethylphenyl)urea.

1-{1-(R)-[4-(3,4-Dichlorobenzyl)piperidin-1-ylmethyl]-2-methylpropyl}-3-(3-dimethylaminomethylphenyl)urea.

1-{1-(R)-[4-(3,4-Dichlorobenzyl)piperidin-1-ylmethyl]-2-methylpropyl}-3-(3-carboxymethylphenyl)urea.

1-{1-(R)-[4-(3,4-Dichlorobenzyl)piperidin-1-ylmethyl]-2-methylpropyl}-3-(3-methoxycarbonylmethylphenyl)urea.

1-{1-(R)-[4-(3,4-Dichlorobenzyl)piperidin-1-ylmethyl]-2-methylpropyl}-3-(3-aminocarbonylmethylphenyl)urea.

1-{1-(R)-[4-(3,4-Dichlorobenzyl)piperidin-1-ylmethyl]-2-methylpropyl}-3-(3-dimethylaminocarbonylmethylphenyl)urea.

GENERAL SYNTHETIC SCHEME

The compounds of the present invention can be prepared in a number of ways known to one skilled in the art. Preferred methods include, but are not limited to, the general synthetic procedures described below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as *Fieser and Fieser's Reagents for Organic Synthesis*, Volumes 1–17 (John Wiley and Sons, 1991); *Rodd's Chemistry of Carbon Compounds*, Volumes 1–5 and Supplementals (Elsevier Science Publishers, 1989), *Organic Reactions*, Volumes 1–40 (John Wiley and Sons, 1991), *March's* Advanced Organic Chemistry, (John Wiley and Sons, 1992), and *Larock's* Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Synthesis of Compounds of Formula (I)

In general, compounds of Formula (I) where n, m, R, $R^1$, $R^2$, $R^3$, $R^4$, $R^5$, Q and $Ar^1$ are as defined in the Summary of the Invention are prepared from aminoalkyl derivatives of Formulae II(a–c) and carboxyalkyl derivatives of Formulae II(d–f) as shown in FIG. 1 below.

Figure 1

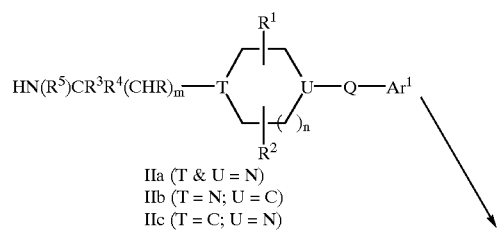

IIa (T & U = N)
IIb (T = N; U = C)
IIc (T = C; U = N)

-continued

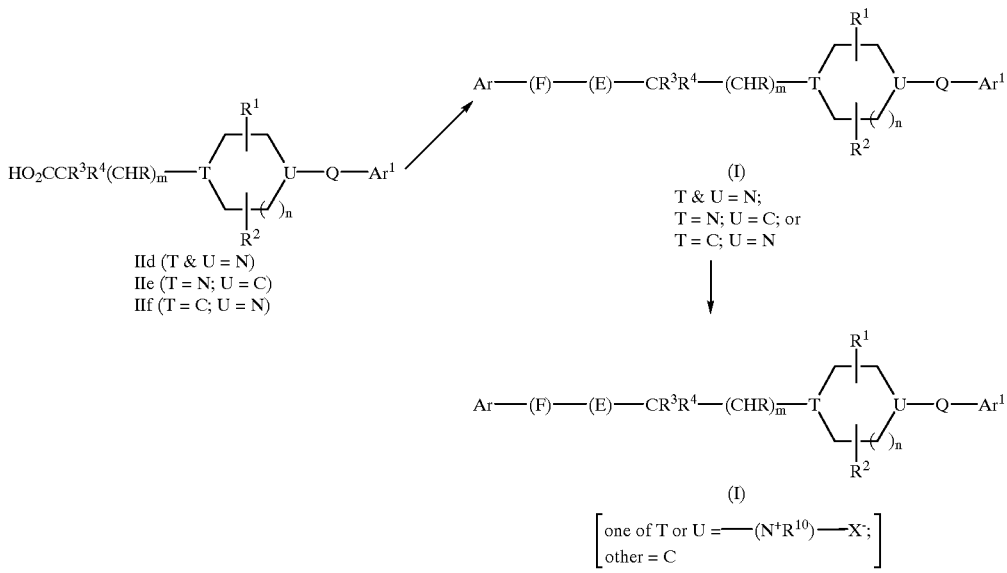

Synthesis of compounds of Formulae II(a–f) and their conversion to compounds of Formula (I) are described in detail in Schemes A–E and F–H, respectively.

Synthesis of Compounds of Formulae II(a–f)

Preparation of Compounds of Formula IIa

A compound of Formula IIa where n is 1 or 2, m is at least 1 and R, $R^1$, $R^2$, $R^3$, $R^4$, $R^5$, Q and $Ar^1$ are as defined in the Summary of the invention is prepared as shown in Scheme A below.

In method (a), an N-protected aminoalkyl derivative of formula 3 where PG is an amino protecting group (e.g., tert-butoxycarbonyl (BOC), benzyloxycarbonyl (CBZ), benzyl, and the like) is prepared by reacting a compound of formula 1 with a compound of formula 4

$$PG\text{—}N(R^5)CR^3R^4(CHR)_{m-1}X \qquad 4$$

where X is an aldehyde (—CHO), ketone (—C(O)R where R is alkyl), carboxy (—COOH) or a reactive carboxy derivative e.g., acid halide. The reaction conditions employed depend on the nature of the X group. If X is an

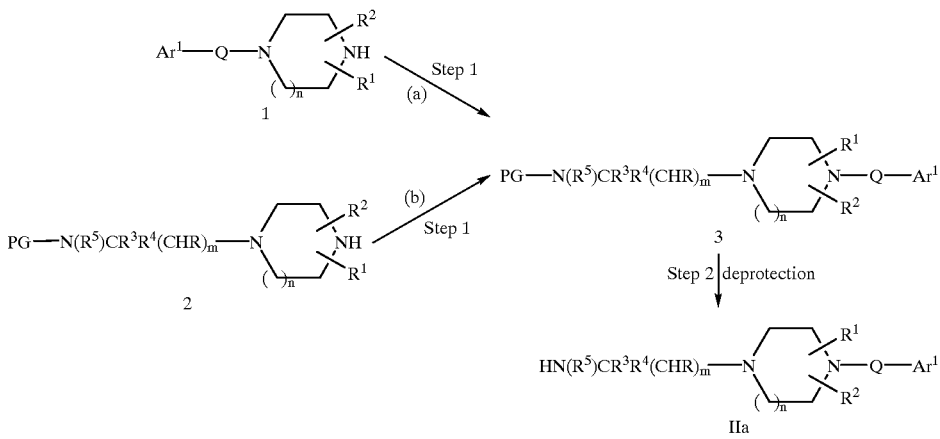

In general, compounds of Formula IIa are prepared in two steps by first converting a compound of formula 1 or 2 to an N-protected aminoalkyl derivative of formula 3 via methods (a) or (b) respectively, followed by removal of the amino protecting group in 3, as described in detail below.

Preparation of Compounds of Formula 3
Method (a)

aldehyde or a ketone group, the reaction is carried out under reductive amination reaction conditions i.e., in the presence of a suitable reducing agent (e.g., sodium cyanoborohydride, sodium triacetoxyborohydride, and the like) and an organic acid (e.g., glacial acetic acid, trifluoroacetic acid, and the like) at ambient temperature to give 3 directly. Suitable solvents for the reaction are halogenated hydrocarbons (e.g., 1,2-dichloroethane, chloroform, and the like). If X is a carboxy group, the reaction is carried out in the presence of a suitable coupling agent (e.g., N,N-dicyclohexylcarbodiimide, 1-(3-dimethylaminopropyl)-3-ethylcarbodiimide, and the like) in a suitable organic solvent (e.g., methylene chloride, tetrahydrofuran, and the like) to give an amide intermediate. Reduction of the amide intermediate with a suitable reducing agent (e.g., diborane, lithium aluminum hydride, and the like) in an ethereal organic solvent such as ether or tetrahydrofuran then provides a compound of formula 3. If X is an acid derivative such as an acid chloride, the reaction is carried out in the presence of a suitable base such as triethylamine, pyridine in an organic solvent (e.g., methylene chloride, dichloroethane, N,N-dimethylformamide, and the like) to give an amide intermediate which is reduced to the corresponding compound of formula 3 as described above.

In general, compounds of formula 4 are either commercially available or they can be prepared by methods well known in the field of organic chemistry. Some examples of such procedures are illustrated and described in detail below.

2-bromopropionate respectively, followed by sequential reduction of the double bond and the ester group in the resulting α,β-unsaturated ester intermediate. The double bond is reduced under hydrogenation reaction conditions and the ester group is reduced to the aldehyde group with reducing agent such as DIBAL-H®. The ketone of formula 4 where m−1=0 can be prepared from the α-amino acids of formula 4 by converting the α-amino acids 4 to a Weinreb amide, followed by treatment with an organometallic reagent such as a Grignard reagent or an organolithium reagent of formula RMgBr or RLi (where R is an alkyl group) respectively.

Generally, both natural and unnatural amino acids and esters are commercially available from vendors such as Aldrich and Bachem. Examples of unnatural amino acids include, homoserine, homocysteine, N-α-methylarginine, norleucine, N-methylisoleucine, phenylglycine, hydroxyproline, pyroglutamine, ornithine, 2-aminoisobutyric acid, 2-aminobutyric acid,

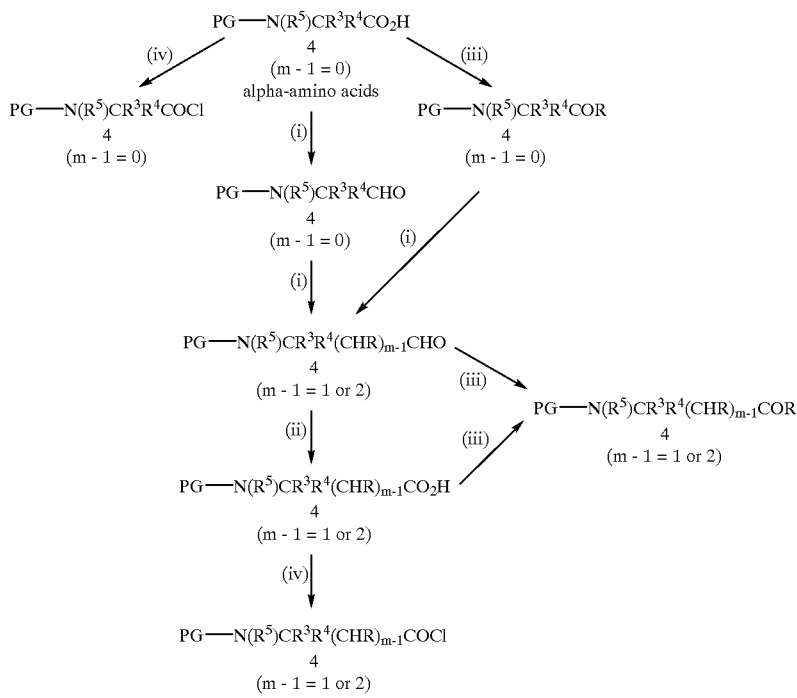

(i) An aldehyde of 4 (X is a —CHO) where m−1=0 is conveniently prepared from the corresponding natural or unnatural α-amino acid of formula 4 where m−1=0 and X is a carboxy group by converting the carboxy group to an ester group followed by reduction of the ester group to an aldehyde group with a suitable reducing agent such as DIBAL-H®. An aldehyde of formula 4 where m−1=1 or 2 can be prepared, if desired, from an aldehyde or ketone (X=—COR where R is alkyl) of formula 4 where m−1=0 under Wittig reaction conditions. For example, an aldehyde 4 where m−1=1 and R is hydrogen or alkyl is prepared by condensing the corresponding aldehyde or ketone of formula 4 where m−1=0 with a Wittig reagent derived from chloromethyl methyl ether, followed by acidic hydrolysis of the resulting enol ether intermediate. An aldehyde 4 where m−1=2 and R are hydrogen or alkyl can be prepared by condensing the corresponding aldehyde or ketone 4 where m−1=0 with a Wittig reagent derived from bromoacetate or β-cyclohexylalanine, 3-(1-naphthyl)alanine, 3-(2-naphthyl)alanine, citrulline, pipecolinic acid, piperazic acid, 4-chlorophenylalanine, 4-fluorophenylalanine, serine methyl ester, valine ethyl ester, and sarcosine. Synthesis of α-amino acids 4 where $R^3$ and $R^5$ together form a morpholino ring and thiomorpholino ring and $R^4$ is hydrogen is described in Kogami, Y., Okawa, K., *Bull. Chem. Soc. Jpn.*, 60, 2963, (1987).

(ii) Compounds of formula 4 where X is a carboxy group and m−1>0 can be prepared from the corresponding aldehydes of formula 4 (X is —CHO), prepared as described in (i) above, by oxidation of the aldehyde group with a suitable oxidizing agent (e.g., potassium permanganate and the like). Alternatively, they can be prepared from the α,β-unsaturated esters formed in the Wittig reaction, see (i) above, by reduction of the double bond followed by the hydrolysis of the ester group by methods well known in the art.

(iii) Compounds of formula 4 where X is —C(O)R (where R is alkyl) and m−1=0, 1 or 2 can be prepared by alkylating the corresponding aldehyde of formula 4 (X is —CHO) with a Grignard reagent followed by oxidation of the resulting alcohol with a suitable oxidizing agent such as pyridinium dichromate and the like. Alternatively, they can be prepared from the corresponding acid of formula 4 as described in (i) above.

(iv) Compounds of formula 4 where X is an acid derivative e.g., an acid chloride, can be prepared from the corresponding acids of formula 4 (X is —COOH), prepared as described in (iii) above, by chlorinating the carboxy group with a suitable chlorinating agent (e.g., oxalyl chloride, thionyl chloride and the like) in a suitable organic solvent such as methylene chloride and the like.

Alternatively, a compound of formula 3 can be prepared directly by reacting a compound of formula 1 with an alkylating agent of formula 5

$$PG—N(R^5)CR^3R^4(CHR)_mY \qquad 5$$

where Y is a leaving group under alkylating conditions such as halo (e.g., chloro, bromo or iodo) or sulfonyloxy group (e.g., methylsulfonyloxy or 4-methylphenylsulfonyloxy or trifluoromethylsulfonyloxy). The reaction is carried out in the presence of a base such as sodium carbonate, sodium hydride, triethylamine and the like. Suitable solvents are aprotic organic solvents such as tetrahydrofuran, N,N-dimethylformamide, and the like.

In general, compounds of formula 5 where Y is a halo or a sulfonyloxy group can be prepared from compounds of formula 4 by reducing the aldehyde, ketone or carboxy group to an alcohol, followed by treatment with a suitable halogenating agent (e.g., thionyl chloride, thionyl bromide, carbon tetrabromide in the presence of triphenylphosphine, and the like) or sulfonylating agent (e.g., methylsulfonyl chloride, para-toluenesulfonyl chloride and triflic anhydride) respectively. Suitable aldehyde, ketone or carboxy reducing agents include lithium aluminum hydride, borane and the like.

In some instances, a compound of Formula IIa can be prepared by reacting a compound of formula 1 with a conjugated nitro-olefin under Michael addition reaction conditions, followed by reduction of the nitro group under standard hydrogenation reaction conditions. Conjugated nitro-olefins are commercially available or can be prepared by known literature procedures e.g., see Corey, E. J. et al., *J. Am. Chem. Soc*, 100(19), 8294–5, (1978). A detailed description of the synthesis of an N-alkylaminopiperazine of Formula IIa by this method is given in Example 2.

Method (b)

In method (b), an N-protected aminoalkyl derivative of formula 3 is prepared by reacting a compound of formula 2 with a compound of formula 6

$$Ar^1—Q—J \qquad 6$$

(where J is an X or Y group as defined above) utilizing the reaction conditions described in method (a) above. Method (b) is particularly suitable for preparing compounds of Formula IIa where Q contains an amido or a carbonyl group.

In general, compounds of formula 6 are commercially available or can be prepared by methods well known in the art. For example, aralkyl halides and aralkyl acids such as benzyl bromide, 3,4-dichlorobenzyl bromide, phenylacetic acids and 2-phenylpropionic acids are commercially available. Others can be prepared from suitable starting materials such as phenylacetic acid, phenylpropanol, 2-pyridineethanol, nicotinic acid etc., by following procedures described for the synthesis of compounds of formula 4 and 5 in method (a) above. Compounds of formula 6 where Q is an alkylene chain interrupted by an amido group and J is a halo or sufonyloxy group can be prepared by following the procedures described in U.S. Pat. No. 4,880,808.

Conversion of Compounds of Formula 3 to Compounds of Formula IIa

In Step 2, the N-protected aminoalkyl derivatives 3, formed in Step 1 via method (a) or (b), are converted to a compound of Formula IIa by removal of the amino protecting group. The conditions utilized depend on the nature of the protecting group. For example, if the protecting group is the tert-butoxycarbonyl group it is removed under acidic hydrolysis reaction condition whereas if it is the benzyl group it is removed under catalytic hydrogenation reaction conditions.

A compound of Formula IIa where $R^5$ is other than hydrogen can be prepared, if desired, by alkylating the corresponding compound of Formula IIa where $R^5$ is hydrogen with an alkylating agent $R^5Y$ where Y is a leaving group under alkylating conditions, utilizing the reaction conditions described in method (a) of Scheme A.

Compounds of formula 1 and 2 are prepared as shown below by reacting a piperazine or homopiperazine of formula 7 with a compound of formula 6, or 4 or 5 respectively, followed by the removal of the amino protecting group, utilizing the reaction conditions described in method (a) above.

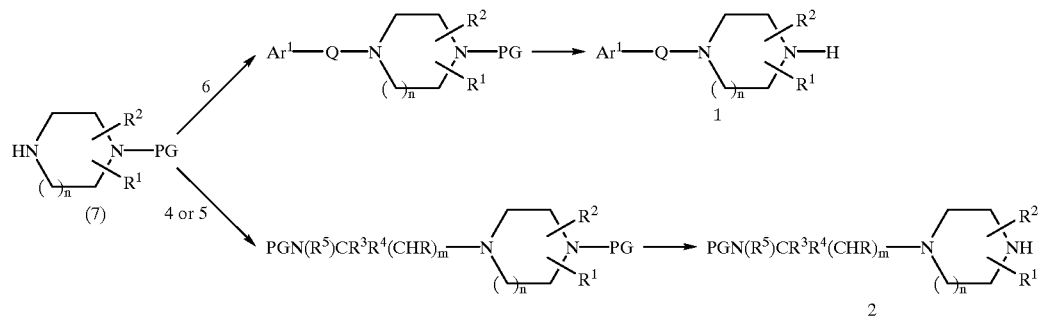

Piperazines and homopiperazines of formula 7 such as piperazine, 2 or 3-methylpiperazines, homopiperazine are commercially available. Piperazines 7 can also be prepared by following the procedures described in the European Pat. Pub. No. 0,068,544 and U.S. Pat. No. 3,267,104. Detailed descriptions of the synthesis of a compound of formula 1 where n=1 by this method is given in Examples 1, 5 and 7.

Preparation of Compounds of Formula IIb

A compound of Formula IIb where m is at least 1 and n, R, $R^1$, $R^2$, $R^3$, $R^4$, $R^5$, Q and $Ar^1$ are as defined in the Summary of the invention can be prepared from a compound of formula 8, where n is 0, 1 or 2 respectively, as illustrated in Scheme B below.

respectively, with a Wittig reagent $Br^-(Ph)_3P^+$-alkylene-$Ar^1$ to give an alkene intermediate. Reduction of the olefinic bond, followed by removal of the N-protecting group then provides compounds of formula 8.

4-Hydroxypiperidines, 3-pyrrolidinols, 3-pyrrolidinones and 4-piperidinones are commercially available. 4-keto-octahydroazepine can be prepared from 2,4-diketo-N-benzylhexahydroazepine ((see Hong Hu G. and Erik Jagdmann Jr., *Tet. Lett.*, 36(21), 3659–62 (1995)) by known procedures.

Scheme B

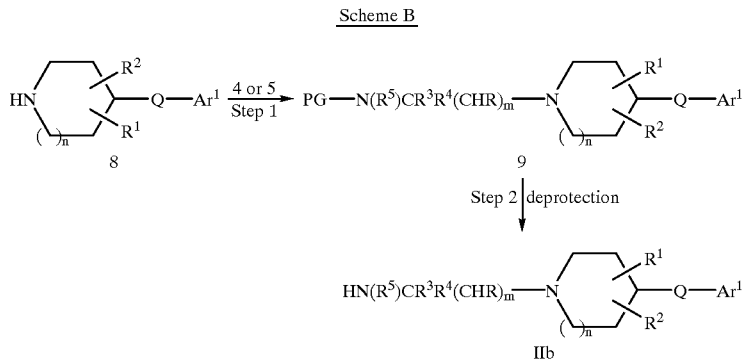

In general, an aminoalkyl derivative of Formula IIb is prepared by reacting a compound of formula 8 with a compound of formula 4 or 5 (see Scheme A) to give an N-protected aminoalkyl derivative of formula 9, followed by removal of the amino protecting group. The conversion of a compound of formula 8 to a compound of Formula IIb is carried out under the reaction conditions described in method (a) of Scheme A above.

Compounds of formula 8 where n is 0, 1 or 2 can be prepared from suitably N-protected pyrrolidinones, piperidinones or 4-keto-octahydroazepines respectively, by known procedures. Some examples of such procedures are described below:

(i) Compounds of formula 8 where n is 0 or 1 and Q is an alkylene chain are prepared by reacting a suitably N-protected-3-pyrrolidinone or N-protected-4-piperidinone Detailed descriptions of the synthesis of compounds of Formula IIb by this method are given in Examples 3 and 4.

Preparation of Compounds of Formula IIc

A compound of Formula IIc where m is 0 or 1, $R^3$ is hydrogen and n, R, $R^1$, $R^2$, $R^4$, $R^5$, Q and $Ar^1$ are as defined in the Summary of the invention can be prepared from a compound of formula 14 or 10 respectively, as illustrated in Scheme C below.

Scheme C

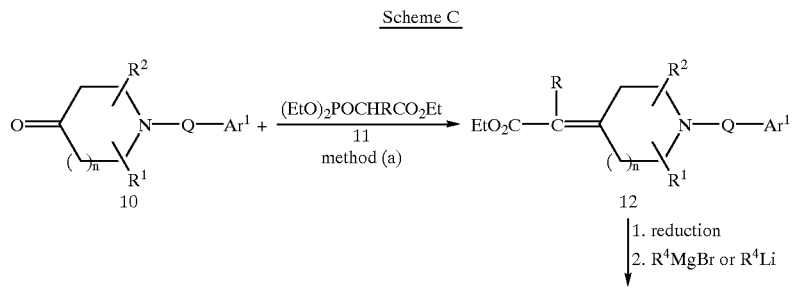

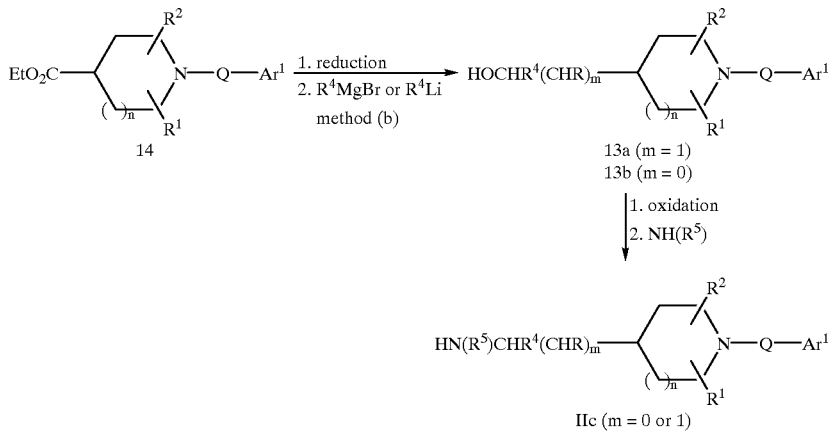

A compound of Formula IIc where m is 1 can be prepared, as shown in method (a), by reacting a compound of formula 10 with a phosphonate ylide of formula 11 under Wittig reaction conditions, i.e., in the presence of a strong non-nucleophilic base (e.g., sodium hydride, sodium amide, and the like) and in a suitable aprotic organic solvent (e.g., tetrahydrofuran and the like) to give an α,β-unsaturated ester of formula 12. The α,β-unsaturated ester 12 is converted to the corresponding alcohol derivative 13a (m=1) by first converting 12 to an aldehyde, followed by treatment with an organometallic reagent such as a Grignard reagent or an organolithium reagent of formula $R^4MgBr$ or $R^4Li$, respectively. The double bond is reduced under hydrogenation reaction conditions and the ester group is reduced to the aldehyde group with a suitable reducing agent such as DIBAL-H®. The alcohol 13a is then converted to a compound of Formula IIc by oxidation of the alcohol group to the ketone group, followed by treatment with an amine of formula $NH(R^5)$ under reductive amination reaction conditions. The oxidation reaction is carried in with a suitable oxidizing reagents such as pyridinium dichromate in an aprotic solvent such as dimethylformamide and the like.

A compound of Formula IIc where m is 0 can be prepared, as shown in method (b) from a compound of formula 14 by converting 14 to the corresponding alcohol derivative 13b (m=0) by reduction of the ester group to the aldehyde followed by treatment with a suitable organometallic reagent. Compound 13b is then converted to a compound of IIc where m is 0 by carrying out the oxidation and reductive amination steps, utilizing the reaction conditions described above. Compounds of Formula IIc where m is 0 can also be prepared by the procedures described in PCT application Publication No. WO 92/12128.

Compounds of formula 10 where n is 0, 1 or 2 are be prepared by N-alkylating a 3-pyrrolidone, a 4-piperidone or a 4-keto-octahydroazepine respectively, with a compound of formula $Ar^1$—Q—Y where Y is a leaving group under alkylating conditions as described in method (a) (2) of Scheme A.

Compounds of formula 14 (n=1) are prepared by N-alkylating an ethyl isonipecotate with a compound of formula $Ar^1$—Q—Y where Y is a leaving group under alkylating conditions as described in method (a) of Scheme A.

Detailed descriptions of the synthesis of a compound of Formula IIc where m is 0 or 1 is given in Examples 9 and 10 respectively.

Preparation of Compounds of Formula IId and IIe

A carboxyalkyl derivative of Formula IId (U=N) and IIe (U=C) where m, n, $R^1$, $R^2$, $R^3$, $R^4$, Q and $Ar^1$ are as defined in the Summary of the invention can be prepared from a compound of formula 1 or 8 respectively, as illustrated in Scheme D below.

Scheme D

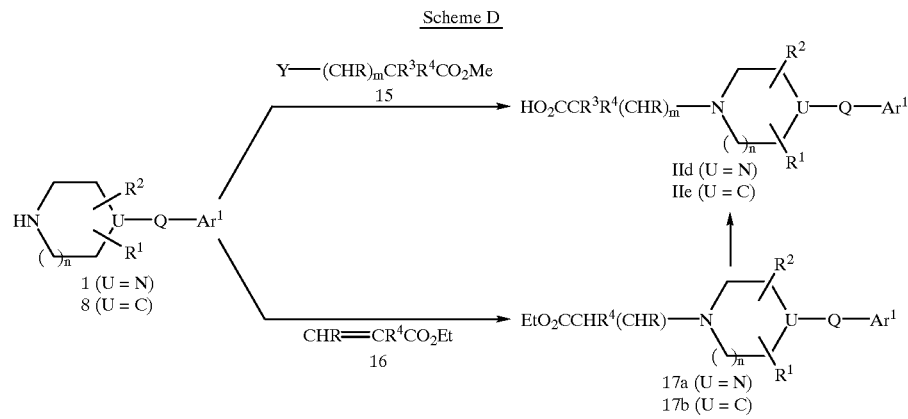

A carboxy derivative of Formula IId or IIe is prepared, as shown above, by reacting a compound of formula 1 or 8 with an alkylating agent of formula 15 where Y is halo or sulfonyloxy group, followed by hydrolysis of the ester group. The alkylation reaction is carried under the reaction conditions described previously ((see scheme A method (a)). The hydrolysis of the ester group is carried out in the presence of an aqueous base (e.g., sodium hydroxide, lithium hydroxide, and the like) in an alcoholic organic solvent such as methanol, ethanol, and the like. The reaction proceeds either at ambient temperature or upon heating. Alternatively, a carboxyethyl derivative of Formula IId or IIe where $R^3$ is hydrogen is prepared by reacting a compound of formula 1 or 8 with an α,β-unsaturated ester of formula 16 under Michael addition reaction conditions i.e., in the presence of a suitable base such as methoxide and in a protic organic solvent (e.g., methanol, ethanol and the like) to give a 3-propionate derivative of formula 17a or 17b, respectively. Hydrolysis of the ester group in 17a or 17b then provides the corresponding carboxyethyl derivative of Formula IId or IIe respectively, where $R^3$ is hydrogen.

Compounds of formula 1 or 8 are prepared as described previously in Schemes A and B respectively. Compounds of formula 15 and 16 are either commercially available or can be prepared by methods known in the art. For example, halo acids and α,β-unsaturated ester such as methyl 2-bromo-2-methylpropionate, methyl 2-bromopropionate, methyl 3-bromo-2-methylpropionate, methyl α-bromophenylacetate, methyl methacrylate are commercially available. A detailed description of the synthesis of a carboxyethylpiperazine of Formula IId by this method is given in Example 6.

Preparation of Compounds of Formula IIf

A carboxyalkyl derivative of Formula IIf where n, m, $R^1$, $R^2$, $R^3$, $R^4$, Q and $Ar^1$ are as defined in the Summary of the invention can be prepared from a compound of formula 17 or 18 respectively, as illustrated in Scheme E below.

Scheme E

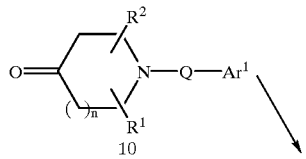

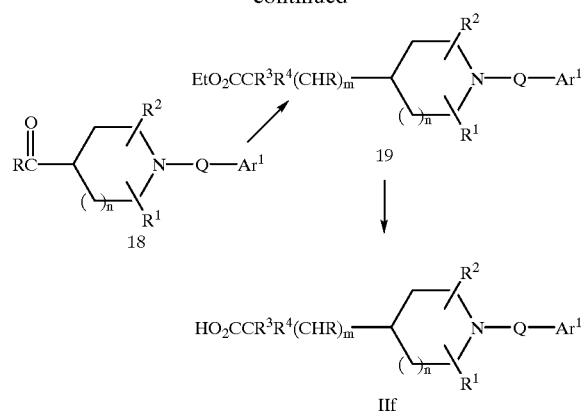

A carboxyalkyl derivative of Formula IIf can be prepared by reacting a compound of formula 10 or 18 with a Wittig reagent of formula Br—$(Ph_3P)(CHR)_m CR^3R^4CO_2Et$, followed by reduction of the double bond and hydrolysis of the ester group to the acid in the resulting unsaturated ester 19, as described previously. Alternatively, compounds of Formula IIf can be prepared from 18 (where R is hydrogen or alkyl) by following the reaction procedures described for the synthesis of compound 4 where X is carboxy in Scheme A, method (a).

Compounds of formula 18 can be prepared from compounds of formula 14 by methods well known in the art.

Compounds of Formula II(d–f) are used for the synthesis of compound of Formula (I) where E is an inverse amide i.e., —$N(R^6)CO$—.

Synthesis of Compounds of Formula (I) where T and U are Nitrogen or One of T and U is Nitrogen and Other Carbon from Compounds of Formulae II (a–f)

Compounds of Formula (I) where T and U are nitrogen or one of T and U is nitrogen and other carbon are prepared from compounds of Formulae II(a–f) as described in Schemes F–J below.

Compounds of Formula (I) where E is —$C(O)N(R^5)$— are prepared as described in Scheme F below:

Scheme F

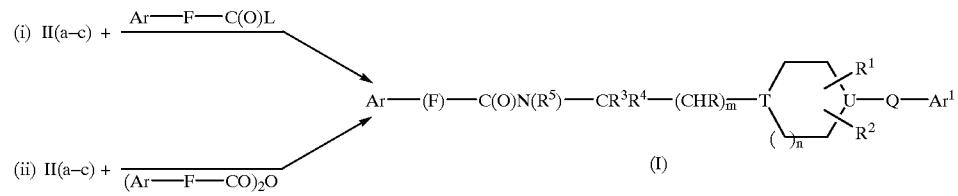

A compound of Formula (I) where E is an amide group can be prepared, either:
(i) by reacting a compound of Formula II(a–c) with an acylating reagent Ar—F—C(O)L, where L is a leaving group under acylating conditions, such as a halo (particularly Cl or Br) or imidazolide. Suitable solvents for the reaction include aprotic polar solvents (e.g., dichloromethane, THF, dioxane and the like). When an acyl halide is used as the acylating agent the reaction is carried out in the presence of a non-nucleophilic organic base (e.g., triethylamine or pyridine, preferably pyridine); or (ii) by heating a compound of Formula II(a–c) with an acid anhydride. Suitable solvents for the reaction are tetrahydrofuran, dioxane and the like. Detailed descriptions of the conversion of a compound of Formula IIa and IIb to compounds of Formula (I) where n is 1 and E is —C(O)NH— is given in Examples 1, 3, 4, 5 and 10.

Compounds of Formula (I) where E is —N(R$^6$)C(O)N(R$^5$)— or —N(R$^6$)C(S)N(R$^5$)— are prepared as described in Scheme G below:

Scheme H

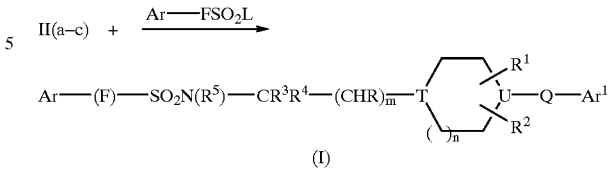

A compound of Formula (I) where E is a sulfonamido group can be prepared by reacting a compound of Formula II(a–c) with a sulfonyl halide, utilizing the reaction conditions described in method (i) of Scheme F. Sulfonyl halides are commercially available or may be prepared by methods such as those described in (1) Langer, R. F.; *Can. J. Chem.* 61, 1583–1592, (1983); (2) Aveta, R.; et. al.; *Gazetta Chimica Italiana*, 116, 649–652, (1986); (3) King, J. F. and Scheme G

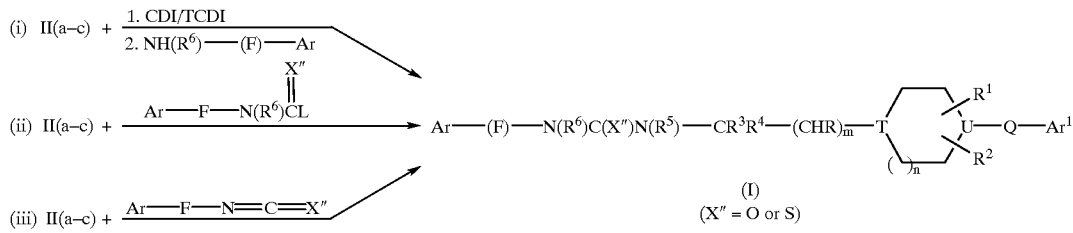

A compound of Formula (I) where E is a urea/thiourea group can be prepared, either:

(i) by reacting a compound of Formula II(a–c) with an activating agent such as carbonyl diimidazole/thiocarbonyl diimidazole, followed by nucleophilic displacement of the imidazole group with a primary or secondary amine. The reaction occurs at ambient temperature. Suitable solvents include polar organic solvents (e.g., tetrahydrofuran, dioxane and the like);

(ii) by reacting a compound of Formula II(a–c) with a carbamoyl/thiocarbamoyl halide. The reaction is carried out in the presence of a non-nucleophilic organic base. Suitable solvents for the reaction are dichloromethane, 1,2-dichloroethane, tetrahydrofuran or pyridine; or (iii) by reacting a compound of formula II(a–c) with an isocyanate/isothiocyanate in an aprotic organic solvent (e.g., benzene, tetrahydrofuran, dimethylformamide and the like).

Detailed descriptions of the conversion of a compound of Formula IIa to a compound of Formula (I) where n is 1 and E is —NHC(O)NH— or —N(R$^6$)C(S)N(R$^5$)— is given in Examples 2 and 8. A detailed description of the conversion of a compound of Formula IIc where m is 0 to a compound of Formula (I) where E is —NHC(O)NH— is given in Example 9.

Compounds of Formula (I) where E is —SO$_2$N(R$^5$)— are prepared as described in Scheme H below:

Hillhouse, J. H.; *Can. J. Chem.*; 54, 498, (1976); and (4) Szymonifka, M. J. and Heck, J. V.; *Tet. Lett.*; 30, 2869–2872, (1989).

A detailed description of the conversion of a compound of Formula IIa to a compound of Formula (I) where n is 1 and E is —N(R$^6$)SO$_2$— is given in Example 7.

Compounds of Formula (I) where E is —N(R$^6$)SO$_2$N(R$^5$)— are prepared as described in Scheme I below:

Scheme I

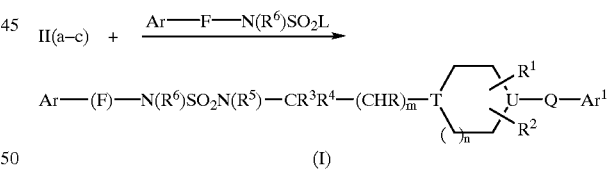

A compound of Formula (I) where E is a sulfamide group can be prepared by reacting a compound of Formula II(a–c) with a sulfamoyl halide, utilizing the reaction conditions described in method (i) of Scheme E. Sulfamoyl halides are commercially available or may be prepared by methods such as those described in Graf, R; *German Patent*, 931225 (1952) and Catt, J. D. and Matler, W. L.; *J. Org. Chem.*, 39, 566–568, (1974).

Compounds of Formula (I) where E is —N(R$^6$)C(O)— are prepared as described in Scheme J below:

Scheme J

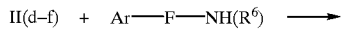

-continued

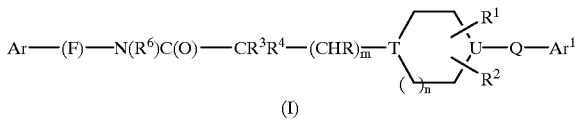

(I)

A compound of Formula (I) where E is an inverse amide can be prepared by reacting a compound of Formula II(d–f) with an amine in the presence of a suitable coupling agent (e.g., N,N-dicyclohexylcarbodiimide, 1-(3-dimethylaminopropyl)-3-ethylcarbodiimide, and the like) in a suitable organic solvent such as methylene chloride, tetrahydrofuran, dimethylformamide and the like. A detailed description of a compound of Formula IId to a compound of Formula I where n is 1 and E is —NHC(O)— is given in Example 6.

Synthesis of a Compounds of Formula (I) where T or U is —(N$^+$R$^{10}$)— X$^-$ from a Corresponding Compound of Formula (I) where One of T and U is Nitrogen and Other is Carbon A compound of Formula (I) where T or U is —N$^+$R$^{10}$— can be prepared from a corresponding compound of Formula (I) as shown in Scheme K below.

Scheme K

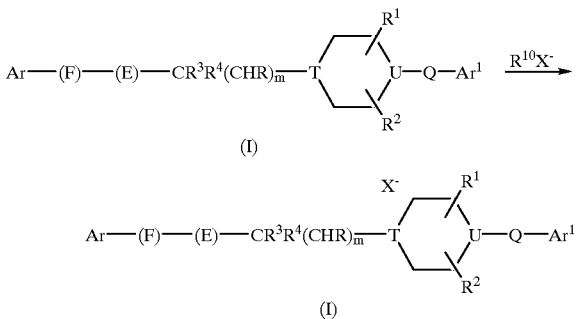

A compound of Formula (I) where T or U is nitrogen is converted to a corresponding compound of Formula (I) where T or U is —N$^+$R$^{10}$— by reacting it with an alkylating agent of formula R$^{10}$X where R$^{10}$ is as defined in the Summary of the Invention and X is a leaving group such as halo (bromide or iodide, preferably iodide), tosylate, mesylate, and the like. Alkylating agents such as methyl iodide, ethyl iodide, ethyl toluenesulfonate, 2-hydroxyethyl iodide, and the like are commercially available.

A compound of Formula (I) where X$^-$ is iodide can be converted to a corresponding compound of Formula (I) where X$^-$ is chloride by utilizing a suitable ion exchange resin such as Dowex 1x8-50.

Utility, Testing and Administration

General Utility

The compounds of the invention are CCR-3 receptor antagonists and inhibit eosinophil recruitment by CCR-3 chemokines such as RANTES, eotaxin, MCP-2, MCP-3 and MCP-4. Compounds of this invention and compositions containing them are useful in the treatment of eosiniphil-induced diseases such as inflammatory or allergic diseases and including respiratory allergic diseases such as asthma, allergic rhinitis, hypersensitivity lung diseases, hypersensitivity pneumonitis, eosinophilic pneumonias (e.g., chronic eosinophilic pneumonia); inflammatory bowel diseases (e.g., Crohn's disease and ulcerative colitis); and psoriasis and inflammatory dermatoses such as dermatitis and eczema.

Testing

The CCR-3 antagonistic activity of the compounds of this invention was measured by in vitro assays such as ligand binding and chemotaxis assays as described in more detail in Examples 18, 19, and 20. In vivo activity was assayed in the Ovalbumin induced Asthma in Balb/c Mice Model as described in more detail in Example 21.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.005–20 mg per kilogram body weight of the recipient per day; preferably about 0.01–10 mg/kg/day. Thus, for administration to a 70 kg person, the dosage range would most preferably be about 0.7 mg to 0.7 g per day.

In general, compounds of this invention will be administered as pharmaceutical compositions by any one of the following routes: oral, inhalation (e.g., intranasal or oral inhalation) or parenteral (e.g., intramuscular, intravenous or subcutaneous) administration. A preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, or any other appropriate compositions. Another preferred manner for administering compounds of this invention is inhalation. This is an effective means for delivering a therapeutic agent directly to the respiratory tract for the treatment of diseases such as asthma and other similar or related respiratory tract disorders (see U.S. Pat. No. 5,607,915).

The choice of formulation depends on various factors such as the mode of drug administration and the bioavailability of the drug substance. For delivery via inhalation the compound can be formulated as liquid solutions or suspensions, aerosol propellants or dry powder and loaded into a suitable dispenser for administration. There are three types of pharmaceutical inhalation devices- nebulizer inhalers, metered-dose inhalers (MDI) and dry powder inhalers (DPI). Nebulizer devices produce a stream of high velocity air that causes the therapeutic agents (which has been formulated in a liquid form) to spray as a mist which is carried into the patient's respiratory tract. MDI's typically have the formulation packaged with a compressed gas. Upon actuation, the device discharges a measured amount of therapeutic agent by compressed gas, thus affording a reliable method of administering a set amount of agent. DPI's administer therapeutic agents in the form of a free flowing powder that can be dispersed in the patient's inspiratory air-stream during breathing by the device. In order to achieve a free flowing powder, the therapeutic agent is formulated with an excipient, such as lactose. A measured amount of the therapeutic is stored in a capsule form and is dispensed to the patient with each actuation.

For liposomal formulations of the drug for parenteral or oral delivery the drug and the lipids are dissolved in a suitable organic solvent e.g. tert-butanol, cyclohexane (1% ethanol). The solution is lypholized and the lipid mixture is suspended in an aqueous buffer an allowed to form a liposome. If necessary, the liposome size can be reduced by sonification. (see., Frank Szoka, Jr. and Demetrios Papahadjopoulos, "Comparative Properties and Methods of Preparation of Lipid Vesicles (Liposomes)", *Ann. Rev. Biophys. Bioeng.*, 9:467–508 (1980), and D. D. Lasic, "Novel Applications of Liposomes", *Trends in Biotech.*, 16:467–608, (1998))

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences* edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described in Example 17.

EXAMPLES

The following preparations and examples are given to enable those skilled in the art to more clearly understand and to practice the present invention. They should not be considered as limiting the scope of the invention, but merely as being illustrative and representative thereof.

Synthetic Examples

Example 1

Synthesis of N-{1(S)-[4-(3,4-Dichlorobenzyl) piperazin-1-ylmethyl]-2-methylpropyl}-4-methylbenzamide dihydrochloride salt

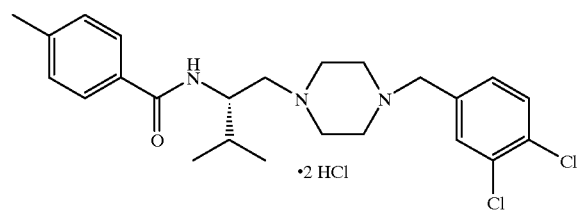

Step 1

3,4-Dichlorobenzyl bromide (35.20 g, 150 mmol) was added to a solution of N-(tertbutoxycarbonyl)piperazine (24.84 g, 130 mmol) and triethylamine (20.91 ml, 150 mmol) in chloroform (100 ml) over 30 min. After 1 h, the reaction mixture was diluted with ethyl acetate and the product was precipitated out as the hydrochloride salt by adding 1N aqueous hydrogen chloride solution. The solid product was filtered, washed with water and then resuspended in ethyl acetate. Two equivalents of 1N aqueous sodium hydroxide solution was added and the free amine was extracted into ethyl acetate. The organic layer was separated, dried over magnesium sulfate, filtered and concentrated to provide 1-(tert-butoxycarbonyl)-4-(3,4-dichlorobenzyl)piperazine (45 g).

Step 2

Trifluoroacetic acid (75 ml, 974 mmol) was added to a solution 1-(tert-butoxycarbonyl)-4-(3,4-dichlorobenzyl) piperazine (45 g, 130 mmol) in chloroform (75 ml). The reaction mixture was stirred for 1 h at room temperature and then made basic with a sodium hydroxide solution. The product was extracted into ethyl acetate and the organic layer was washed with sodium bicarbonate solution, dried over magnesium sulfate and concentrated in vacuo to give 1-(3,4-dichlorobenzyl)piperazine (35.8 g) as a solid.

Step 3

1-(3-Dimethylaminopropyl)-3-ethylcarbodiimide hydrochloride (5.08 g, 26.5 mmol) was added to a solution of 1-(3,4-dichlorobenzyl)piperazine (5 g, 20.4 mmol) and L-Boc-valine (5.76 g, 26.5 mmol) in methylene chloride. After 2 h, the product was extracted into ethyl acetate. The organic layer was washed with sodium bicarbonate solution, dried over magnesium sulfate, filtered and concentrated in vacuo. Column chromatography with hexanes/ethyl acetate (1:1) as the eluant gave 1-(S)-[4-(3,4-dichlorobenzyl) piperazin-1-ylcarbonyl]-N-(tert-butoxycarbonyl)-2-methylpropylamine (5.46 g) as a foam.

Step 4

1 N ethereal hydrogen chloride solution (80 ml, 80 mmol) was added to a solution of 1(S)-[4-(3,4-dichlorobenzyl) piperazin-1-ylcarbonyl]-N-(tert-butoxycarbonyl)-2-methylpropylamine (4.28 g, 9.64 mmol) in methanol (50 ml) and the reaction mixture was heated at 70° C. After 2.5 h, the reaction mixture was concentrated and the solid was suspended in ether and filtered to give 1-(S)-[4-(3,4-dichlorobenzyl)piperazin-1-yl carbonyl]-2-methylpropylamine as the bis hydrochloride salt. The product was dissolved in water, treated with triethylamine (4.0 ml, 28.9 mmol) and the free amine was extracted into ethyl acetate. The ethyl acetate layer was dried over magnesium sulfate, filtered and concentrated to give 1-(S)-[4-(3,4-dichlorobenzyl)piperazin-1-ylcarbonyl]-2-methylpropylamine (3.2 g) as the free amine.

Step 5

A 1.0 M diborane solution in tetrahydrofuran (65.2 ml, 65.2 mmol) was added to a solution of 1-(S)-[4-(3,4-dichlorobenzyl)piperazin-1-ylcarbonyl]-2-methylpropylamine (3.2 g, 9.3 mmol) in tetrahydrofuran (15 ml). The mixture was heated at reflux under nitrogen atmosphere for 2 h and then concentrated in vacuo. The residue was dissolved in methanol, acidified with 6 N hydrogen chloride solution (50 ml) and then reheated to 70° C. After heating for 1 h, the reaction mixture was cooled and basified with a sodium hydroxide solution and the product was extracted into ethyl acetate. The ethyl acetate layer was washed with sodium bicarbonate solution, dried over magnesium sulfate, filtered and concentrated to provide 1-(S)-[4-(3,4-dichlorobenzyl)piperazin-1-ylmethyl]-2-methylpropylamine (3.53 g) as an oil.

Step 6 p-Toluoyl chloride (0.48 ml, 3.63 mmol) was added to a solution of 1(S)-[4-(3,4-dichlorobenzyl)piperazin-1-ylmethyl]-2-methylpropylamine (1 g, 3.0 mmol) and triethylamine (0.633 ml, 4.54 mmol) in methylene chloride under nitrogen atmosphere. After 1h, the product was extracted into ethyl acetate and the organic layer was washed with sodium bicarbonate solution, dried over magnesium sulfate, filtered and concentrated in vacuo. Column chromatography with hexanes/ethyl acetate (1:2) gave N-{1(S)-[4-(3,4-dichlorobenzyl)-piperazin-1-ylmethyl]-2-methylpropyl}-4-methylbenzamide (1.2 g) as an oil. The free amine was dissolved in ether and 3.5 equivalents of 1N ethereal HCl solution (10.7 ml) was added. Filtration of the resulting solid provided N-{1(S)-[4-(3,4-dichlorobenzyl)piperazin-1-ylmethyl]-2-methylpropyl}-4-methylbenzamide (1.2 g) as the bis hydrochloride salt, mp 227.8–228.9° C.

1. Proceeding as described in Example 1, Steps 1–4 above but substituting L-Boc-valine in Step 3 with DL-Boc-valine gave 1-(RS)-[4-(3,4-dichlorobenzyl)piperazin-1-ylcarbonyl]-2-methylpropylamine which upon reduction (step 5) and reaction with 3,4-methylenedioxybenzoyl chloride (step 6) gave N-{1(RS)-[4-(3,4-dichlorobenzyl)-piperazin-1-ylmethyl]-2-methylpropyl}-3,4-methylenedioxybenzamide.

2. Proceeding as described in Example 1, Steps 1–4 above but substituting L-Boc-valine in Step 3 with L-Boc-tert-leucine (commercially available from Fluka) gave 1-(S)-[4-(3,4-dichlorobenzyl)piperazin-1-ylcarbonyl]-2,2-dimethylpropylamine which was reduced to 1-(S)-[4-(3,4-dichloro-benzyl)piperazin-1-ylmethyl]-2,2-methylpropylamine (Step 5) and then reacted with:

4-Methylsulfonylbenzoyl chloride;
4-Acetoxybenzoyl chloride;
4-N,N-Dimethylaminobenzoyl chloride;
5-Methyl-2-thenoyl chloride; and
4-Methylbenzoyl chloride, to give N-{1(S)-[4-(3,4-Dichlorobenzyl)piperazin-1-ylmethyl]-2,2-dimethylpropyl}-4-methylsulfonylbenzamide dihydrochloride salt, mp 190–191° C.;

N-{1(S)-[4-(3,4-Dichlorobenzyl)piperazin-1-ylmethyl]-2,2-dimethylpropyl}-4-acetoxybenzamide dihydrochloride salt, mp 241–242° C.;

N-{1(S)-[4-(3,4-Dichlorobenzyl)piperazin-1-ylmethyl]-2,2-dimethylpropyl}-4-N,N-dimethylaminobenzamide dihydrochloride salt, mp 101.5–105° C.;

N-{1(S)-[4-(3,4-Dichlorobenzyl)piperazin-1-ylmethyl]-2,2-dimethylpropyl}-5-methyl-2-thiophenecarboxamide dihydrochloride salt, mp 249–253° C.; and N-{1(S)-[4-(3,4-Dichlorobenzyl)piperazin-1-ylmethyl]-2,2-dimethylpropyl}-4-methylbenzamide dihydrochloride salt by following the procedure described in Steps 5 and 6 above.

3. Proceeding as described in Example 1, Steps 1–4 above but substituting L-Boc-valine in Step 3 with DL-Boc-tert-leucine gave 1-(RS)-[4-(3,4-dichlorobenzyl)-piperazin-1-ylcarbonyl]-2,2-methylpropylamine which was reduced to 1-(RS)-[4-(3,4-dichloro-benzyl)piperazin-1-ylmethyl]-2,2-methylpropylamine (Step 5) and reacted with:

3-Cyanobenzoyl chloride; and
3,4-Difluorobenzoyl chloride, to give
N-{1(RS)-[4-(3,4-Dichlorobenzyl)piperazin-1-ylmethyl]-2,2-dimethylpropyl}-3-cyanobenzamide; and
N-{1(RS)-[4-(3,4-Dichlorobenzyl)piperazin-1-ylmethyl]-2,2-dimethylpropyl}-3,4-difluorobenzamide, respectively.

4. Proceeding as described in Example 1, but substituting N-(tert-butoxycarbonyl)-piperazine in Step 1 with 3-methyl-N-(tert-butoxycarbonyl)piperazine and L-Boc-valine in Step 3 with DL-Boc-valine gave N-{1(RS)-[3-methyl-4-(3,4-dichlorobenzyl)piperazin-1-ylmethyl]-2-methylpropyl}-4-methylbenzamide dihydrochloride salt.

Example 2

Synthesis of 1-{2-[4-(3,4-Dichlorobenzyl)-piperazin-1-yl]cyclohexyl}-3-(3-methoxyphenyl) urea

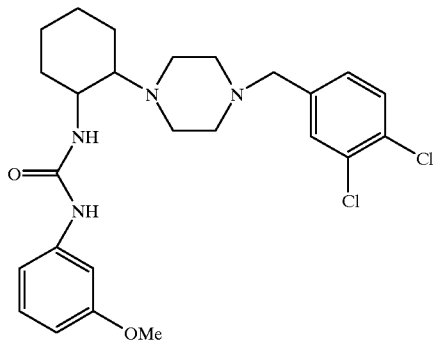

Step 1

A mixture of 1-nitrocyclohexene (311 mg, 2.45 mmol), dichlorobenzylpiperazine [prepared as described in Example 1](600 mg, 2.45 mmol), and triethylamine (512 µl, 3.68 mmol) in methylene chloride (10 ml) was stirred at room temperature under nitrogen atmosphere for 17 h. The reaction mixture was diluted with ethyl acetate, washed with an aqueous sodium bicarbonate solution, dried over magnesium sulfate and concentrated in vacuo. The residue was chromatographed with hexanes/ethyl acetate (2:1) as the eluant to provide 1-(3,4-dichlorobenzyl)-4-(2-nitrocyclohexyl) piperazine (461 mg) as an oil.

Step 2

Platinum (IV) oxide (15 mg, 0.07 mmol) was added to a solution of 1-(3,4-dichlorobenzyl)-4-(2-nitrocyclohexyl) piperazine (187 mg, 0.50 mmol) in glacial acetic acid (5 ml). The reaction mixture was stirred under hydrogen atmosphere at room temperature for 16 h. The reaction mixture was then filtered through a pad of celite. The filtrate was made basic with a 15% sodium hydroxide solution and the product was extracted into ethyl acetate. The organic layer was dried over magnesium sulfate, filtered and concentrated in vacuo to provide 1-(3,4-dichlorobenzyl)-4-(2-aminocyclohexyl)-piperazine (119 mg) as an oil.

Step 3

A solution of 1-(3,4-dichlorobenzyl)-4-(2-aminocyclohexyl)piperazine (100 mg, 0.29 mmol) and 3-methoxyphenyl isocyanate (38 µl, 0.29 mmol) in methylene chloride (5 ml) was stirred at room temperature. After 17 h, the product was extracted into ethyl acetate, washed with a bicarbonate solution, dried over magnesium sulfate and concentrated in vacuo. Column chromatography with methylene chloride/methanol (97:3) as the eluant gave 1-{2-[4-(3,4-dichlorobenzyl)piperazin-1-yl]cyclohexyl}-3-(3-methoxyphenyl)urea(64 mg) as an oil consisting of the trans diastereomer.

Example 3

Synthesis of N-{1-(S)-[4-(3,4-Dichlorobenzyl) piperidin-1-ylmethyl]-2-methylpropyl}-4-methylbenzamide

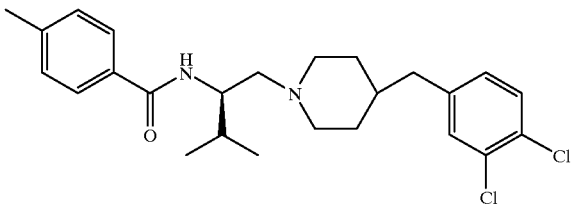

Step 1 n-Butyllithium (43.2 ml, 2M in pentane, 108 mmol) was slowly added to an ice-cooled suspension of 3,4-dichlorobenzyl triphenylphosphonium bromide (54 g, 108 mmol) (prepared by stirring equimolar amounts of 3,4 dichlorobenzyl bromide and triphenylphosphine in THF at 65° overnight) in dry THF (500 ml) under an argon atmosphere. After 15 min., the reaction mixture was allowed to warm to room temperature, and was stirred for an additional 2 h. 1-tert-butoxycarbonyl-4-piperidone (21.42 g, 108 mmol) was added and the stirring was continued overnight. Hexane (2 l) was added and the reaction was stirred and then filtered. The filtrate was concentrated in vacuo to give 41.8 g of an orange gum. Column chromatography on 0.5 kg flash grade silica, eluting with a gradient of 70% methylene chloride/hexane through 100% methylene chloride, followed by a gradient of 1% methanol/methylene chloride through 5% methanol/methylene chloride gave 1-(tert-butoxycarbonyl)-4-(3,4-dichlorobenzylidene)piperidine (29 g) as a light tan oil.

Step 2

Platinum oxide (0.3 g) was added to a solution of 1-(tert-butoxycarbonyl)-4-(3,4-dichlorobenzylidene)piperidine (29 g, 84.7 mmol) in ethyl acetate (500 ml) and the mixture was stirred under a hydrogen atmosphere overnight. The reaction mixture was filtered through celite and the filtrate was concentrated to give 1-(tert-butoxycarbonyl)-4-(3,4-dichlorobenzyl)piperidine (30 g) as a tan oil.

Step 3

Trifluoroacetic acid (50 ml) was added to a solution of 1-(tert-butoxycarbonyl)-4-(3,4-dichlorobenzyl)piperidine (24 g, 69.7 mmol) in methylene chloride (150 ml) and the reaction mixture was stirred for 1 h. The solvent was removed under reduced pressure, followed by addition of ethyl acetate (200 ml), and the resulting mixture was made basic with 1N aqueous sodium hydroxide. The organic layer was separated, dried over magnesium sulfate and the solvent was removed under reduced pressure to give 4-(3,4-dichlorobenzyl)piperidine (17.1 g) as light brown solid.

Step 4

L-BOC-Valine (1.3 g, 5.98 mmol) and 1-(3-dimethylaminopropyl)-3-ethylcarbodiimide (1.15 g, 5.98 mmol) were added to a solution of 4-(3,4-dichloro-benzyl) piperidine (1.12 g, 4.57 mmol) in methylene chloride (15 ml) and the reaction mixture was stirred at room temperature under an argon atmosphere. After 3 h the solvents were removed under vacuo and water (10 ml) and ethyl acetate (25 ml) were added. The organic layer was separated, dried over magnesium sulfate and concentrated under reduced pressure. Column chromatography with 15–20% ethyl acetate/hexane as the eluant gave 1-(S)-[4-(3,4-dichlorobenzyl)-piperidin-1-ylcarbonyl]-N-(tert-butoxycarbonyl)-2-methylpropylamine (1.89 g) as a gummy foam.

Step 5

To a solution of 1-(S)-[4-(3,4-dichlorobenzyl)piperidin-1-ylcarbonyl]-N-(tert-butoxycarbonyl)-2-methylpropylamine (5.9 g, 13.2 mmol) in methylene chloride (100 ml) was added trifluoroacetic acid (30 ml) at room temperature. After 4 h, the reaction mixture was concentrated and the residue was stirred with ethyl acetate (200 ml) and water (100 ml) while adjusting the pH to 8 with 15% aqueous sodium hydroxide solution. The organic layer was separated and the aqueous layer was extracted twice with ethyl acetate. The combined organic portions were dried over magnesium sulfate, filtered and concentrated in vacuo to give 1-(S)-[4-(3,4-dichlorobenzyl)piperidin-1-ylcarbonyl-2-methylpropylamine (4.53 g) as a colorless gum.

Step 6

To a solution of 1-(S)-[4-(3,4-dichlorobenzyl)piperidin-1-ylcarbonyl-2-methylpropylamine (4.53 g, 13.3 mmol) in dry tetrahydrofuran (100 ml) was added diborane (92.4 ml, 92.4 mmol, 1 M in THF) and the reaction mixture was stirred under argon at 65° C. After 3 h, the reaction mixture was cooled in an ice bath and aqueous hydrochloric acid (60 ml, 6 N) was slowly added with stirring. The reaction mixture was concentrated on a rotovap and the aqueous solution was stirred at 100° C. After 1 h, the reaction mixture was cooled to 0° C. and potassium hydroxide pellets were slowly added until pH 8 was obtained. The solution was extracted twice with ethyl acetate (100 ml), dried over magnesium sulfate and concentrated in vacuo. The colorless liquid (3.84 g) was flash chromatographed, eluting with 2.5–10% MeOH/CH$_2$Cl$_2$ containing 1% NH$_4$OH. The free amine was dissolved in anhydrous ether and ethereal HCl was added to afford 1-(S)-[4-(3,4-dichlorobenzyl)piperidin-1-ylmethyl]-2-methylpropylamine as the HCl salt.

Step 7 p-Toluoyl chloride (0.14 ml, 1 mmol) was added to a solution of 1-(S)-[4-(3,4-dichlorobenzyl)piperidin-1-ylmethyl]-2-methylpropylamine (0.33 g, 1 mmol) in dry pyridine (7 ml) at 0° C. under argon atmosphere. The solution was stirred for 30 min., at 0° C. and then allowed to warm to room temperature. After 3 h, the reaction mixture was concentrated under reduced pressure and water (10 ml) was added. The product was extracted with ethyl acetate and the organic layer was dried with magnesium sulfate and then concentrated in vacuo. The crude product (0.5 g) was chromatographed by eluting with a gradient of from 1% to 4% methanol/methylene chloride to give N-{1-(S)-[4-(3,4-dichlorobenzyl)piperidin-1-ylmethyl]-2-methylpropyl}-4-methylbenzamide (0.25 g) as partially solidified gum.

Example 4

N-{1-(RS)-[4-(4-Amino-5-chloro-2-methoxyphenylcarbonylaminomethyl)piperidin-1-ylmethyl]-2-methylpropyl}-4-methylbenzamide

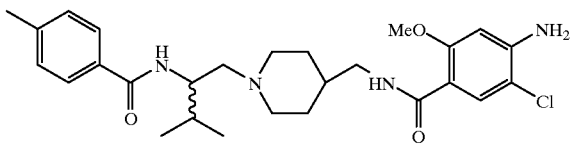

Step 1

Diisopropylethyl amine (17.4 ml, 134 mmol) was added a solution of (DL)-valinol (9.85 g, 95 mmol) in methylene chloride (100 ml). The reaction mixture was cooled to 0° C., treated with a solution of p-toluoyl chloride (12.8 ml, 91 mmol ) in methylene chloride (50 ml) and then allowed to warm to room temperature. After stirring for 3 hours, excess aqueous sodium hydroxide solution was added and the reaction was transferred to a separatory funnel. The organic layer was separated and the aqueous layer washed with one portion of methylene chloride. The combined organic layers were washed with water and brine, dried over magnesium sulfate and concentrated in vacuo. Chromatography eluting with 25% ethyl acetate in hexanes, followed by 50% ethyl acetate in hexanes gave N-p-toluoyl valinol (18.04 g).

Step 2

Dimethylsulfoxide (2.2 ml, 31 mmol) was slowly added via syringe to a stirred –78° C. solution of oxalyl chloride (15 ml, 171 mmol) in methylene chloride (35 ml) under inert atmosphere. After 10 min., a solution of N-p-toluoyl valinol (6.0 g, 29 mmol) in methylene chloride (50 ml) was added and the stirring was continued for additional 15 min. Triethylamine was added (6 ml, 389 mmol) and the reaction was allowed to warm to ambient temperature. After 1.5 h, the reaction was diluted with 50% ethyl acetate in hexanes and washed with water and brine. Filtration through a pad of silica gel and subsequent solvent removal left a solid residue. Chromatography eluting with 20% ethyl acetate in hexanes, then 33% ethyl acetate in hexanes gave N-p-toluoyl valinaldehyde (3.6 g) as a solid, which was utilized in Step 6.

Step 3 tert-Butyloxycarbonyl anhydride (6.69 g, 30.6 mmol) was added to a solution of 4-(aminomethyl)piperidine (7 g, 61.3 mmol) in chloroform (40 ml) at 0° C. The reaction mixture was allowed to warm to room temperature over 3 h and then stirred an additional 15 h. The reaction mixture was washed with water, the organic layer was separated and dried over magnesium sulfate, filtered and concentrated to provide N-tert-butyloxy-carbonyl-4-(aminomethyl)piperidine (6.55 g) as a pale yellow oil.

Step 4

1,1'-Carbonyldiimidazole (1.61 g, 9.91 mmol) was added to a solution of 4-amino-5-chloro-2-methoxybenzoic acid (2.0 g, 9.91 mmol) in dimethylformamide (5 ml). After stirring for 5 min. at room temperature, solution of N-tert-butyloxycarbonyl-4-(aminomethyl)piperidine (1.77 g, 8.26 mmol) in dimethylformamide (5 ml) was added and the reaction mixture was heated at 55° C. After 23 h, the product was extracted into ethyl acetate and the organic layer was washed with aqueous sodium bicarbonate, dried over magnesium sulfate, filtered and concentrated. Flash chromatography of the crude product with 2:1, ethyl acetate/hexanes as the eluant gave N-tert-butyloxycarbonyl-4-(4-amino-5-chloro-2-methoxyphenylcarbonylaminomethyl)piperidine (2.63 g) as a foam.

Step 5

To a solution of N-tert-butyloxycarbonyl-4-(4-amino-5-chloro-2-methoxyphenylcarbonylaminomethyl)piperidine (500 mg, 1.26 mmol) in methanol solution (30 ml) was added an ethereal 1N hydrogen chloride solution (12.6 ml, 12.6 mmol). The solution was heated at 50° C. The reaction mixture became heterogeneous within 5 min. After 1.5 h, the reaction mixture was concentrated to give a white solid which was suspended in diethylether and filtered to give 4-(4-amino-5-chloro-2-methoxyphenylcarbonylaminomethyl)piperidine as a bis-hydrochloride salt (433 mg).

Step 6

To a heterogeneous mixture of 4-(4-amino-5-chloro-2-methoxyphenylcarbonylaminomethyl)piperidine (304 mg, 0.82 mmol) and triethylamine (309 µl, 2.21 mmol) in methylene chloride (20 ml) was added aldehyde N-p-toluoyl valinaldehyde (150 mg, 0.68 mmol) and sodium triacetoxyborohydride (216 mg, 1.02 mmol) at room temperature. After 1 h the reaction mixture was diluted with ethyl acetate and washed with sodium bicarbonate solution. The organic layer was separated, dried over magnesium sulfate and concentrated in vacuo. Flash chromatography of the crude product with 97:3, methylene chloride/methanol as the eluant gave N-{1(RS)-[4-(4-amino-5-chloro-2-methoxyphenylcarbonyl-aminomethyl)piperidin-1-ylmethyl]-2-methylpropyl}-4-methylbenzamide(139 mg) as a foam.

Example 5

{1-(4-Methylbenzoyl)-2(R)-[4-(3,4-dichlorobenzyl) piperazin-1-ylmethyl]}-pyrrolidine dihydrochloride salt

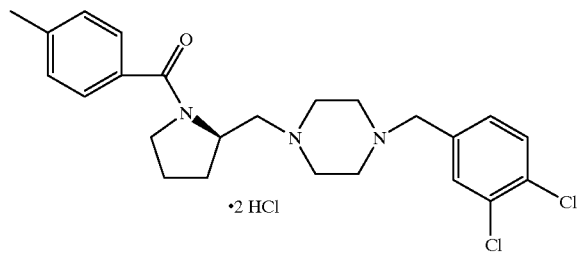

Step 1

1-Ethyl-3-(3'-dimethylaminopropyl)carbodiimide hydrochloride (1.03 g, 7 mmol) was added to a solution of N-BOC-D-Proline (1.51 g, 7 mmol) in methylene chloride (12 ml) and the reaction mixture was stirred at room temperature. After 0.5 h, 3,4-dichlorobenzylpiperazine (1.32 g, 5.4 mmol) [prepared as described in Example 1] was added and the stirring was continued for 16 h. The reaction mixture was then quenched with water, basified with saturated sodium bicarbonate solution and extracted with ethyl acetate. The ethyl acetate layer was separated and washed with brine, dried over magnesium sulfate and concentrated. Flash chromatography with 30% acetone in dichloromethane as the eluant gave 2(R)-[4-(3,4-dichlorobenzyl) piperazin-1-ylcarbonyl]}-N-(tert-butoxycarbonyl) pyrrolidine (1.2 g) as an oil.

Step 2

Borane (15.8 ml, 1.0 M solution in THF) was added dropwise to a solution of 2(R)-[4-(3,4-dichlorobenzyl) piperazin-1-ylcarbonyl]}-N-(tert-butoxycarbonyl) pyrrolidine (1.0 g, 2.26 mmol) in tetrahydrofuran (5 ml) was under nitrogen atmosphere and the reaction mixture was heated at reflux. After 2 h, the reaction mixture was cooled to room temperature and quenched with 6 N hydrochloric acid. The reaction mixture was re-heated at reflux for another 2 h, cooled to room temperature and then basified with 10% aqueous sodium hydroxide solution. The product was extracted into ethyl acetate and the organic layer was separated and washed with brine, dried over magnesium sulfate, and concentrated. Purification with column chromatography with methylene chloride containing 10% ammonium hydroxide in methanol as the eluant gave 2(R)-[4-(3, 4-dichlorobenzyl)piperazin-1-ylmethyl]}pyrrolidine (0.62 g) as an oil.

Step 3

Triethylamine (0.19 ml, 1.5 mmol) and p-toluoyl chloride (0.11 ml, 0.84 mmol) were added to a solution of 2(R)-[4-(3,4-dichlorobenzyl)piperazin-1-ylmethyl]-pyrrolidine (0.25 g, 0.76 mmol) in methylene chloride (5 ml). After 1 h, the reaction mixture was quenched with water and the product was extracted into ethyl acetate. The ethyl acetate layer was washed with brine, dried over magnesium sulfate and concentrated. Preparative TLC with 5% methanol in methylene chloride afforded {1-(4-methylbenzoyl)-2(R)-[4-(3,4-dichlorobenzyl)piperazin-1-ylmethyl]}pyrrolidine 0.245 g of an oil which was converted to its dihydrochloride salt and recrystallized from a methanol-ethyl acetate mixture to give {1-(4-methylbenzoyl)-2(R)-[4-(3,4-dichlorobenzyl)-piperazin-1-ylmethyl]}pyrrolidine dihydrochloride (0.18 g) as a white solid; m.p. 249.6–250.1° C.

Example 6

Synthesis of 2-(RS)-[4-(3,4-Dichlorobenzyl) piperazin-1-ylmethyl]-N-(4-methylphenyl) propionamide

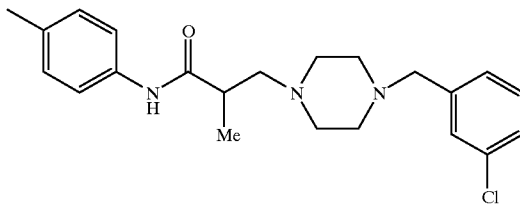

Step 1

A mixture of 3,4-dichlorobenzylpiperazine (2.47 g, 10.1 mmol), methyl methacrylate (2.2 ml, 21 mmol), and sodium methoxide (49 mg, 0.91 mmol) in methanol (20 ml) was heated to reflux. After 72 h, the reaction mixture was concentrated under reduced pressure to yield pale-yellow oil (3.02 g). Column chromatography on silica gel with ethyl acetate as eluant afforded methyl 2-(RS)-[4-(3,4-dichlorobenzyl)piperazin-1-ylmethyl]propionate (1.52 g) as a pale-yellow oil.

Step 2

Methyl 2-[4-(3,4-dichlorobenzyl)piperazin-1-ylmethyl] propionate (470 mg, 1.36 mmol) and lithium hydroxide monohydrate (185 mg, 4.41 mmol) were dissolved in water (5 ml) and methanol (15 ml) and stirred at room temperature. After 21 h, the solvents were removed under reduced pressure. The resulting residue was taken up in a mixture of methylene chloride and water, and the aqueous layer was made acidic (~pH 4) with 1M HCl. The layers were separated and the aqueous phase was extracted with several portions of methylene chloride. The combined organic layers were dried over sodium sulfate and concentrated under reduced pressure to afford 2-(RS)-[4-(3,4-dichloro-benzyl) piperazin-1-ylmethyl]propionic acid (444 mg) as a pale-yellow foam.

Step 3

1-Ethyl-3-(3'-dimethylaminopropyl)carbodiimide hydrochloride (388 mg, 2.02 mmol) was added to a solution of 2-[4-(3,4-dichlorobenzyl)piperazin-1-ylmethyl]-propionic acid (609 mg, 1.84 mmol) p-toluidine (219 mg, 2.04 mmol) and dimethylaminopyridine (22 mg, 0.18 mmol) in methylene chloride (20 ml). After 4 h, the mixture was diluted with methylene chloride and washed with water. The organic layer was separated, dried with sodium sulfate and the solvent removed under reduced pressure to give an orange foam (839 mg). Column chromatography on silica gel with ethyl acetate as eluant yielded 2-[4-(3,4-dichlorobenzyl) piperazin-1-ylmethyl]-N-(4-methyl-phenyl)propionamide (636 g, 82%) as a white foam. A 1M solution of hydrochloric acid in ether (4.2 ml) was added to a solution of this product (593 mg, 1.41 mmol) in methanol and the solvent was removed under reduced pressure. The resulting viscous oil was triturated with ether/hexanes to yield 2-(RS)-[4-(3,4-dichlorobenzyl)piperazin-1-yl-methyl]-N-(4-methylphenyl) propionamide(245 mg) as the hydrochloride salt, m.p. 256.2–256.7° C.

Example 7

N-{1-(R)-[4-(3,4-Dichlorobenzyl)piperazin-1-ylmethyl]-2-methylpropyl}-4-fluorobenzenesulfonamide dihydrochloride salt

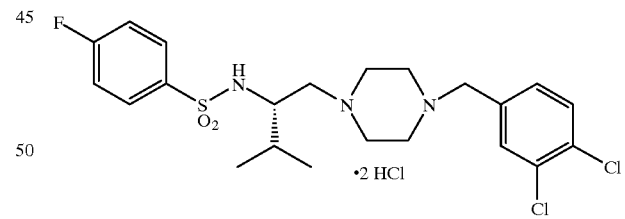

Triethylamine (21 ml, 0.15 mmol) and 4-fluorobenzenesulfonyl chloride (29 mg, 0.15 mmol) were added to a solution of 1-(R)-[4-(3,4-dichlorobenzyl) piperazin-1-ylmethyl]-2-methylpropylamine (50 mg, 0.15 mmol) [prepared as described in Example 1 above] in methylene chloride (1.5 ml). The reaction mixture was stirred for 2 h, then concentrated. Purification by flash chromatography with 20:1 methylene:methanol as the eluant gave N-{1-(R)-[4-(3,4-dichlorobenzyl)piperazin-1-ylmethyl]-2-methylpropyl}-4-fluorobenzenesulfonamide (49 mg) as a solid.

Example 8

1-{1-(RS)-[4-(3,4-Dichlorobenzyl)piperazin-1-ylmethyl]-2-methylpropyl}-3-methoxybenzyl-2-thiourea

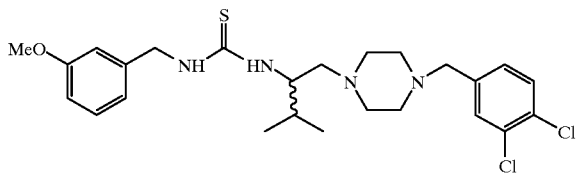

3-Methoxybenzyl isothiocyanate (22 mg, 0.12 mmol) was added to a solution of 1-(RS)-[4-(3,4-dichlorobenzyl)piperazin-1-ylmethyl]-2-methylpropylamine (40 mg, 0.12 mmol) [prepared as described in Example 1 by substituting L-N-BOC-valine with DL-N-BOC-valine] in methylene chloride (1.5 ml). The reaction mixture was stirred for 2 h and then concentrated. Purification by flash chromatography with 20:1 methylene chloride:methanol as the eluant gave 1-{1-(RS)-[4-(3,4-dichlorobenzyl)piperazin-1-ylmethyl]-2-methylpropyl}-3-methoxybenzyl-2-thiourea (18 mg) as a solid.

Example 9

1-{1(RS)-[1-(3,4-Dichlorobenzyl)piperidin-4-yl]-2-methylpropyl}-3-(3-methoxyphenyl)urea

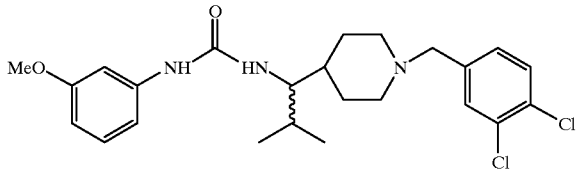

Step 1

3,4-Dichlorobenzyl bromide (1.83 g, 7.63 mmol) was added to a solution of ethyl isonipecotate (1 g, 6.36 mmol) and triethylamine (1.33 ml, 9.54 mmol) in methylene chloride solution (10 ml) at room temperature. After 17 h, the reaction mixture was diluted with ethyl acetate and washed with aqueous sodium bicarbonate solution (10 ml). The organic layer was dried over magnesium sulfate, filtered, and concentrated. Flash chromatography with 9:1, hexanes/ethyl acetate followed by 6:1 hexanes/ethyl acetate gave ethyl 1-(3,4-dichlorobenzyl)isonipecotate (1.78 g) as a pale yellow oil.

Step 2

A 1.5 M solution of DIBAL-H™ in toluene (1.27 ml, 1.90 mmol) was added dropwise over 10 min. to a solution of ethyl 1-(3,4-dichlorobenzyl)isonipecotate (500 mg, 1.58 mmol) in toluene solution (5 ml) at −78° C. After 40 min., aqueous sodium bicarbonate solution was added and the reaction mixture was warmed to room temperature. The product was extracted into diethyl ether. The organic layer was dried over magnesium sulfate, filtered and concentrated to provide 1-(3,4-dichlorobenzyl)-4-formylpyridine (430 mg) as an oil.

Step 3

Isopropylmagnesium chloride in tetrahydrofuran (3.7 ml, 7.35 mmol, 2.0 M) was added to a solution of 1-(3,4-dichlorobenzyl)-4-formylpyridine (1 g, 3.67 mmol) in tetrahydrofuran (10 ml) at 0° C. After 30 min., the reaction mixture was warmed to room temperature and stirred an additional 30 min. The reaction mixture was then diluted with diethyl ether and washed with sodium bicarbonate solution (10 ml). The organic layer was separated and dried over magnesium sulfate, filtered and concentrated. The residue was subjected to flash chromatography (1:1, hexanes/ethyl acetate) to provide alcohol 1(RS)-[(3,4-dichlorobenzyl)pyridin-4-yl]-2-methylpropanol (617 mg) as an oil.

Step 4

Pyridinium dichromate (6 g, 15.9 mmol) was added to a solution of 1(RS)-[(3,4-dichlorobenzyl)pyridin-4-yl]-2-methylpropanol (617 mg, 1.95 mmol) in N,N-dimethylformamide (35 ml) at 0° C. After 4.5 h, the reaction mixture was diluted with ethyl acetate and washed with sodium bicarbonate solution (30 ml). The organic layer was separated and dried over magnesium sulfate, filtered and concentrated. The residue was subjected to flash chromatography (1.5:1, hexanes/ethyl acetate) to provide 1-[(3,4-dichlorobenzyl)pyridin-4-yl]-2-methylpropanone (432 mg) as an oil.

Step 5

Ammonium acetate (1.43 g, 18.33 mmol) followed by sodium cyanoborohydride (130 mg, 1.86 mmol) were added to a solution of 1-[(3,4-dichlorobenzyl)pyridin-4-yl]-2-methylpropanone (583 mg, 1.86 mmol) in methanol 10 ml) at room temperature. After 50 h, additional amounts of ammonium acetate (1.43 g, 18.33 mmol) and sodium cyanoborohydride (130 mg, 1.86 mmol) were added. After 17 h, the reaction mixture was diluted with ethyl acetate and washed with sodium bicarbonate solution (10 ml). The organic layer was separated and dried over magnesium sulfate, filtered and concentrated. The residue was dissolved in ethyl acetate and the product extracted into 1N HCl solution. The acidic aqueous layer was made basic with sodium hydroxide solution and the product was extracted into ethyl acetate. The organic layer was dried over magnesium sulfate, filtered and concentrated. The residue was subjected to flash chromatography (90:10, methylene chloride/methanol followed by 80:20) to provide 1(RS)-[(3, 4-dichlorobenzyl)pyridin-4-yl]-2-methylpropylamine(390 mg) as an oil.

Step 6

3-methoxyphenyl isocyanate (37 μl, 0.28 mmol) was added to a solution of provide 1(RS)-[(3,4-dichlorobenzyl)pyridin-4-yl]-2-methylpropylamine(88 mg, 0.28 mmol) in methylene chloride solution (2 ml) at room temperature. After 1 h, the reaction mixture was diluted with ethyl acetate and washed with sodium bicarbonate solution (5 ml). The organic layer was separated and dried over magnesium sulfate, filtered and concentrated to provide 1-{1(RS)-[1-(3, 4-dichlorobenzyl)piperidin-4-yl]-2-methylpropyl}-3-(3-methoxyphenyl)urea. (104 mg) as a white solid. mp 161.4–161.8° C.

Proceeding as described in Example 9, Step 6 above but substituting 1(RS)-[(3,4-dichlorobenzyl)pyridin-4-yl]-2-methylpropylamine with 1-(R)-[4-(3,4-dichlorobenzyl)-piperazin-1-ylmethyl]-2-methylpropylamine (prepared as described in Example 1) gave 1-{1(R)-[1-(3,4-dichlorobenzyl)piperazin-1-yl]-2-methylpropyl}-3-(3-methoxyphenyl)urea.

Example 10

N-{1-[1(RS)-[1-(3,4-Dichlorobenzyl)piperidin-4-ylmethyl]-2-methylpropyl}-4-methylbenzamide dihydrochloride salt

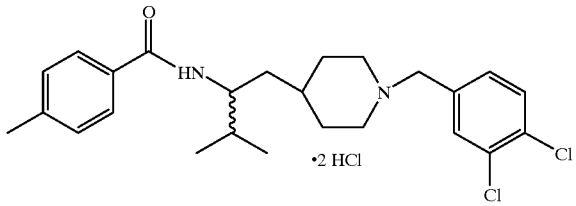

Step 1

To a suspension of 4-piperidone hydrochloride (3.52 g, 22.9 mmol) in ethanol (40 ml) was added triethylamine (10.8 ml, 91.6 mmol), followed by the addition of 3,4-dichlorobenzyl bromide (5.0 g, 20.8 mmol) and the reaction mixture was stirred overnight at room temperature. The reaction mixture was concentrated in vacuo and the residue was partitioned between water and ethyl acetate. The ethyl acetate layer was separated, washed with brine, dried over magnesium sulfate and concentrated in vacuo. Column chromatography with 25% ethyl acetate and 25% dichloromethane in hexanes gave 1-(3,4-dichlorobenzyl)-4-piperidone (4.4 g) as a colorless oil.

Step 2

To a suspension of sodium hydride (0.33 g, 13.2 mmol) in dry toluene (15 ml) was added triethyl phosphonoacetate (2.6 ml, 13.2 mmol) at a rate such that the internal reaction temperature remained below 25° C. After stirring at room temperature for 0.5 h, the reaction mixture was recooled to below 25° C. and a solution of 1-(3,4-dichlorobenzyl)-4-piperidone (3.10 g, 12 mmol) in toluene (6 ml) was added dropwise. After the addition was complete, a gummy precipitate formed The mixture was heated at 60–65° C. for 10 min. and then cooled to room temperature. The mother liquor was decanted and the residue was washed with more toluene. The combined toluene layers were filtered through a celite pad and concentrated in vacuo to give ethyl [1-(3,4-dichlorobenzyl)piperidin-4-ylidene] acetate (3.9 g) as an oil which was used in the next step without further purification.

Step 3

Ethyl [1-(3,4-dichlorobenzyl)piperidin-4-ylidene]acetate (3.9 g, 11.9 mmol) dissolved in tetrahydrofuran (25 ml) and ethanol (25 ml) was subjected to hydrogenation over platinum oxide (0.1 g) at ambient temperature and atmospheric pressure. The reaction mixture was filtered through a celite pad and concentrated in vacuo to give ethyl [1-(3,4-dichlorobenzyl)piperidin-4-yl]acetate (3.91 g) as a semisolid.

Step 4

DIBAL-H (6.9 ml, 10.35 mmol, 1.5 M in toluene) was added to a solution of ethyl [1-(3,4-dichlorobenzyl)piperidin-4-yl]acetate (1.9 g, 5.8 mmol) in dry toluene (60 ml) at −60° C. under nitrogen atmosphere. The reaction mixture was stirred at dry ice bath temperature for 0.5 h, quenched with saturated sodium bisulfite solution and then allowed to warm to room temperature. The aqueous layer was separated and basified with 2N sodium hydroxide to pH between 8–9 and the product was extracted with diethyl ether. The combined ether layers were washed with brine and dried over sodium sulfate. After concentration, the residue was dissolved in dry tetrahydrofuran (30 ml) and cooled to 0° C. Isopropyl magnesium chloride (2.0 M, 5.8 ml) was added dropwise and the resulting reaction mixture was allowed to warm to room temperature. After 0.5 h, the reaction mixture was quenched with water and extracted with diethyl ether. The ether layer was washed with brine, dried over sodium sulfate and concentrated in vacuo. The residue was purified on silica gel column with 25% acetone, 25% dichloromethane in hexanes to give 1(RS)-[1-(3,4-dichlorobenzyl)piperidin-4-ylmethyl]-2-methylpropanol (0.75 g) as an oil.

Step 5

Pyridinium dichromate (4.0 g, 10.63 mmol) was added to a solution of 1(RS)-[1-(3,4-dichlorobenzyl)piperidin-4-ylmethyl]-2-methylpropanol (0.5 g, 1.5 mmol) in dimethylformamide (25 ml) at 0° C. The resulting solution was stirred at 0° C. until the starting material was consumed and then quenched with water, basified with 2N sodium hydroxide and extracted with ethyl acetate. The organic layer was washed with water, brine, and dried over sodium sulfate. The residue was purified on silica gel with 25% acetone, 25% dichloromethane in hexanes to give 1-[1-(3,4-dichlorobenzyl)piperidin-4-yl]-3-methyl-2-butanone (0.32 g) as an oil.

Step 6

To a solution of 1-[1-(3,4-dichlorobenzyl)piperidin-4-yl]-3-methyl-2-butanone (0.16 g, 0.49 mmol) in methanol (1.5 ml) was added ammonium acetate (0.38 g, 4.93 mmol), followed by sodium cyanoborohydride (31 mg, 0.5 mmol) and the resulting solution was stirred at room temperature. After 48 h, hydrochloric acid (conc.) was added until pH was 2 and the volatiles were removed under vacuum. The residue was dissolved in water and washed with ethyl acetate. The aqueous layer was then basified to pH>10 and extracted with ethyl acetate. The ethyl acetate layer was washed with brine, dried over sodium sulfate and concentrated to give 1(RS)-[1-(3,4-dichlorobenzyl)piperidin-4-ylmethyl]-2-methylpropylamine(0.16 g) as an oil which was used in the next step without further purification.

Step 7 p-Toluoyl chloride (0.077 ml, 0.58 mmol) was added to a solution of 1(RS)-[1-(3,4-dichlorobenzyl)piperidin-4-ylmethyl]-2-methylpropylamine(0.16 g, 0.49 mmol) in dichloromethane (2 ml) and triethylamine (0.12 ml, 1.63 mmol). The reaction mixture was stirred at room temperature for 1.5 h and was quenched with water. The product was then extracted with dichloromethane and the organic layer was washed with brine and dried over sodium sulfate. The crude product was purified on preparative TLC with 25% acetone, 25% dichloromethane in hexanes to give 0.21 g of N-{1-[1(RS)-[1-(3,4-dichlorobenzyl)piperidin-4-ylmethyl]-2-methylpropyl}-4-methylbenzamide as an oil, which was then converted to its dihydrochloride salt (0.15 g); m.p. 233.9–235.5° C.

Example 11

N-{1-(R)-[4-(Dichlorobenzyl)piperidin-1-ylmethyl]-2-methylpropyl}-5-methylthiophene-2-carboxamide hydrochloride salt

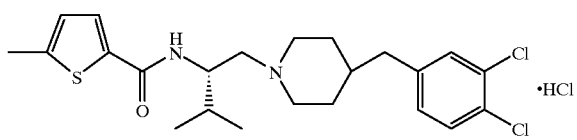

To a solution of 1-(R)-[4-(3,4-dichlorobenzyl)piperidin-1-ylmethyl]-2-methyl-propylamine (0.52 g, 1.58 mmol)

[prepared as described in Example 3, Step 5), in methylene chloride (15 ml) was added 5-methyl-2-thiophenecarboxylic acid (0.29 g, 2.05 mmol) followed by 1-(3-dimethylaminopropyl)-3-ethylcarbodiimide (0.39 g, 2.05 mmol), and the solution was stirred under argon overnight at room temperature. After concentrating the reaction mixture, water (10 ml) and ethyl acetate (25 ml) were added and the reaction mixture was stirred while adjusting to pH 8 with dilute aqueous potassium carbonate solution. The organic layer was separated and the aqueous layer was extracted with ethyl acetate (25 ml). The combined organic layers were dried over magnesium sulfate, filtered and concentrated in vacuo. The crude material (0.86g) was flash chromatographed on silica, eluting with 2% methanol/methylene chloride (containing 1% ammonium hydroxide) to give 0.64 g product as a gum. Anhydrous HCl/ether (5 ml) was added to an ether solution of the product, giving a gummy precipitate which was further dissolved in methanol (10 ml) and stripped to give N-{1-(R)-[4-(dichlorobenzyl)piperidin-1-ylmethyl]-2-methylpropyl}-5-methylthiophene-2-carboxamide hydrochloride salt (0.72 g) as a light yellow foam.

Example 12

N-{1-(R)-[4-(Dichlorobenzyl)piperidin-1-ylmethyl]-2-methylpropyl}-4-(2-aminoethyl)benzamide dihydrochloride salt

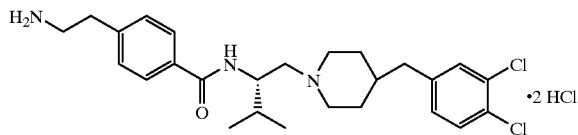

Step 1
A solution of 4-bromophenethylamine (10 g, 50 mmol), di-tert-butyldicarbonate (21.82 g, 100 mmol), triethylamine (13.9 ml, 100 mmol), and anhydrous methanol (350 ml) was refluxed for 2 h. The reaction mixture was concentrated in vacuo and the residue was stirred with water, filtered, washed with water and air dried to give N-(tert-butoxycarbonyl)-4-bromophenethylamine (15 g).

Step 2
To a 0° C. solution of N-(tert-butoxycarbonyl)-4-bromophenethylamine (12.82 g, 42.6 mmol) in anhydrous ether (200 ml) under argon was added dropwise n-butyllithium (34 ml, 85.2 mmol, 2.5 M in hexane). The slightly yellow solution turned milky white and was stirred 15 min., at 0° followed by one hour at room temperature. The resulting mixture was cooled to −78° C. in a dry ice-acetone bath. Dry carbon dioxide was bubbled through the stirring reaction mixture for 30 min., and then the reaction mixture was allow to slowly warm to room temperature over 30 min. Water (100 ml) was added, the pH adjusted to 8 with dilute aqueous potassium carbonate solution, and the aqueous layer was separated and extracted with ethyl acetate. The aqueous layer was then cooled to 0° C. and acidified to pH 3 with 3 N aqueous hydrochloric acid. The resulting white precipitate was filtered, washed with water and air dried to provide 4-[2-(N-tert-butoxycarbonylamino)ethyl]benzoic acid (7.8 g).

Step 3
To a room temperature solution of 1-(R)-[4-(3,4-dichlorobenzyl)piperidin-1-yl-methyl]-2-methylpropylamine (1 g, 3.04 mmol) (prepared as described in Example 3, Step 5) in methylene chloride (30 ml) was added 4-[2-(N-tert-butoxycarbonylamino)-ethyl]benzoic acid (1 g, 3.8 mmol) followed by 1-(3-dimethylaminopropyl)-3-ethyl-carbodiimide (0.73 g, 3.8 mmol) and the solution was stirred under argon overnight at room temperature. After concentrating the reaction mixture, water (25 ml) and ethyl acetate (60 ml) were added and the reaction mixture was stirred while adjusting the pH to 8 with dilute aqueous potassium carbonate solution. The organic layer was separated and the aqueous layer was extracted with ethyl acetate (50 ml). The combined organic layers were dried over magnesium sulfate and concentrated. The resulting crude product was flash chromatographed on silica, eluting with 2%–4% methanol/methylene chloride containing 1% ammonium hydroxide to give N-{1-[1(R)-[1-(3,4-dichlorobenzyl)-piperidin-4-ylmethyl]-2-methylpropyl}-4-[2-(N-tert-butoxycarbonylamino)ethyl]-benzamide as a white foam.

Step 4
To a room temperature solution of give N-{1-[1(R)-[1-(3,4-dichlorobenzyl)-piperidin-4-ylmethyl]-2-methylpropyl}-4-[2-(N-tert-butoxycarbonylamino)ethyl]-benzamide (1.34 g, 2.32 mmol) in methylene chloride (30 ml) was added trifluoroacetic acid (30 ml). After 3 h, the reaction mixture was concentrated in vacuo and the residue was stirred with ethyl acetate (100 ml) and water (50 ml) while adjusting the pH to 8 with 15% aqueous sodium hydroxide solution. The organic layer was separated and the aqueous layer was extracted twice with ethyl acetate. The combined organic portions were dried with magnesium sulfate and concentrated. The crude was flash chromatographed on silica, eluting with 3% methanol/methylene chloride (containing 1% ammonium hydroxide). The free base product was dissolved in anhydrous ether and 1N anhydrous HCl/ether was added to give N-{1-(R)-[4-(dichlorobenzyl)piperidin-1-yl-methyl]-2-methylpropyl}-4-(2-aminoethyl)benzamide as the hydrochloride salt, mp 190.5–261.6° C.

Example 13

1-{1-(R)-[4-(3,4-Dichlorobenzyl)piperidin-1-ylmethyl]-2-methylpropyl}-3-(3-methoxyphenyl)urea

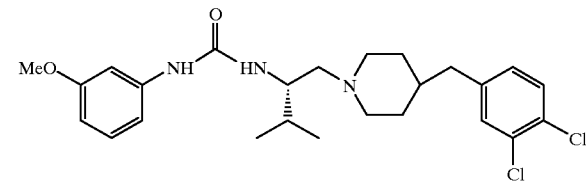

To a room temperature solution of 1-(R)-[4-(3,4-dichlorobenzyl)piperidin-1-ylmethyl]-2-methylpropylamine (0.349 g, 1.06 mmol) (prepared as in Example 3, steps 4 and 5, but using D-Boc-Valine in place of L-Boc-Valine) in methylene chloride (50 ml) was added 3-methoxyphenylisocyanate (0.17 ml, 1.27 mmol) and the reaction mixture was stirred at room temperature under argon for 2 h. The reaction mixture was concentrated in vacuo and the crude product was flash chromatographed on silica, eluting with 1–3% methanol/methylene chloride (containing 1% ammonium hydroxide). The product was dissolved in anhydrous ether and 1N anhydrous HCl/ether was added to precipitate 1-{1-(R)-[4-(3,4-dichlorobenzyl)piperidin-1-ylmethyl]-2-methylpropyl}-3-(3-methoxyphenyl)-urea as the hydrochloride salt (0.29 g), mp 107–112° C.

Proceeding as described in Example 13 above, but substituting 3-methoxyphenylisocyanate with 3,4,5-trimethoxyphenylisocyanate gave 1-{1-(R)-[4-(3,4-dichlorobenzyl)-piperidin-1-ylmethyl]-2-methylpropyl}-3-(3,4,5-trimethoxyphenyl)urea.

Proceeding as described in Example 13 above, but substituting 3-methoxyphenylisocyanate with 3,4,5-trimethoxyphenylisocyanate and 1-(R)-[4-(3,4-dichlorobenzyl)-piperidin-1-ylmethyl]-2-methylpropylamine with 1-(R)-[4-(3,4-dichlorobenzyl)-piperidin-1-ylmethyl]-2,2-dimethylpropylamine gave 1-{1-(R)-[4-(3,4-dichlorobenzyl)-piperidin-1-ylmethyl]-2,2-dimethylpropyl}-3-(3,4,5-trimethoxyphenyl)urea.

Proceeding as described in Example 13 above, but substituting 3-methoxyphenylisocyanate with 3-nitrophenylisocynate gave 1-{1-(R)-[4-(3,4-dichlorobenzyl)-piperidin-1-ylmethyl]-2-methylpropyl}-3-(3-nitrophenyl)urea which was then converted to the corresponding 1-{1-(R)-[4-(3,4-dichlorobenzyl)piperidin-1-ylmethyl]-2-methylpropyl}-3-(3-aminophenyl)urea under catalytic hydrogenation conditions using $PtO_2$ catalyst, followed by reaction with methylsulfonyl chloride to give 1-{1-(R)-[4-(3,4-dichlorobenzyl)-piperidin-1-ylmethyl]-2-methylpropyl}-3-(3-methylsulfonylaminophenyl)urea.

Example 14

4-(3,4-Dichlorobenzyl)-1-ethyl-1-{3-methyl-2-[3-(3,4,5-trimethoxyphenyl)-ureido]butyl}piperidinium iodide

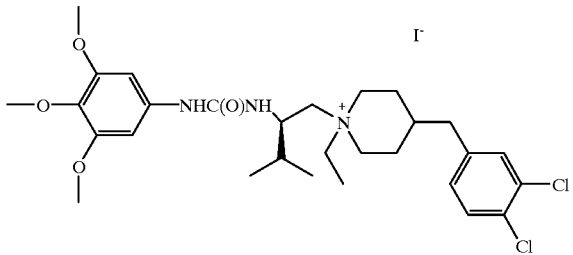

Step 1 n-Butyllithium (43.2 ml, 2 M in pentane, 108 mmol) was slowly added to an ice-cooled suspension of 3,4-dichlorobenzyl triphenylphosphonium bromide (54 g, 108 mmol) (prepared by stirring equimolar amounts of 3,4 dichlorobenzyl bromide and triphenylphosphine in THF at 65° C. overnight) in dry THF (500 ml) under an argon atmosphere. After 15 min., the reaction mixture was allowed to warm to room temperature and was stirred for an additional 2 h. 1-tert-Butoxycarbonyl-4-piperidone (21.42 g, 108 mmol) was added and the stirring was continued overnight. Hexane (2 l) was added and the reaction was stirred and then filtered. The filtrate was concentrated in vacuo to give 41.8 g of an orange gum. Column chromatography on 0.5 kg flash grade silica, eluting with a gradient of 70% methylene chloride/hexane through 100% methylene chloride, followed by a gradient of 1% methanol/methylene chloride through 5% methanol/methylene chloride gave 1-(tert-butoxycarbonyl)-4-(3,4-dichlorobenzylidene)piperidine (29 g) as a light tan oil.

Step 2

Platinum oxide (0.3 g) was added to a solution of 1-(tert-butoxycarbonyl)-4-(3,4-dichlorobenzylidene)piperidine (29 g, 84.7 mmol) in ethyl acetate (500 ml) and the reaction mixture was stirred under a hydrogen atmosphere overnight. The reaction mixture was filtered through celite and the filtrate was concentrated to give 1-(tert-butoxycarbonyl)-4-(3,4-dichlorobenzyl)piperidine (30 g) as a tan oil.

Step 3

Trifluoroacetic acid (50 ml) was added to a solution of 1-(tert-butoxycarbonyl)-4-(3,4-dichlorobenzyl)piperidine (24 g, 69.7 mmol) in methylene chloride (150 ml) and the reaction mixture was stirred for 1 h. The solvent was removed under reduced pressure, followed by addition of ethyl acetate (200 ml), and the resulting mixture was made basic with 1N aqueous sodium hydroxide. The organic layer was separated, dried over magnesium sulfate and the solvent was removed under reduced pressure to give 4-(3,4-dichlorobenzyl)piperidine (17.1 g) as light brown solid.

Step 4

D-BOC-Valine (1.3 g, 5.98 mmol) and 1-(3-dimethylaminopropyl)-3-ethyl-carbodiimide (1.15 g, 5.98 mmol) were added to a solution of 4-(3,4-dichloro-benzyl)piperidine (1.12 g, 4.57 mmol) in methylene chloride (15 ml) and the reaction mixture was stirred at room temperature under an argon atmosphere. After 3 h the solvents were removed undervacuo and water (10 ml) and ethyl acetate (25 ml) were added. The organic layer was separated, dried over magnesium sulfate and concentrated under reduced pressure. Column chromatography with 15–20% ethyl acetate/hexane as the eluant gave 1-(R)-[4-(3,4-dichlorobenzyl)piperidin-1-ylcarbonyl]-N-(tert-butoxy-carbonyl)-2-methylpropylamine (1.89 g) as a gummy foam.

Step 5

To a solution of 1-(R)-[4-(3,4-dichlorobenzyl)piperidin-1-ylcarbonyl]-N-(tert-butoxycarbonyl)-2-methylpropylamine (5.9 g, 13.2 mmol) in methylene chloride (100 ml) was added trifluoroacetic acid (30 ml) at room temperature. After 4 h, the reaction mixture was concentrated and the residue was stirred with ethyl acetate (200 ml) and water (100 ml) while adjusting the pH to 8 with 15% aqueous sodium hydroxide solution. The organic layer was separated and the aqueous layer was extracted twice with ethyl acetate. The combined organic portions were dried over magnesium sulfate, filtered and concentrated in vacuo to give 1-(R)-[4-(3,4-dichlorobenzyl)piperidin-1-ylcarbonyl-2-methylpropylamine (4.53 g) as a colorless gum.

Step 6

To a solution of 1-(R)-[4-(3,4-dichlorobenzyl)piperidin-1-ylcarbonyl-2-methyl-propylamine (4.53 g, 13.3 mmol) in dry tetrahydrofuran (100 ml) was added diborane (92.4 ml, 92.4 mmol, 1 M in THF) and the reaction mixture was stirred under argon at 65° C. After 3 h, the reaction mixture was cooled in an ice bath and aqueous hydrochloric acid (60 ml, 6 N) was slowly added with stirring. The reaction mixture was concentrated in vacuo and the aqueous solution was stirred at 100° C. After 1 h, the reaction mixture was cooled to 0° C. and potassium hydroxide pellets were slowly added until pH 8 was obtained. The solution was extracted twice with ethyl acetate (100 ml), dried over magnesium sulfate and concentrated in vacuo. The colorless liquid (3.84 g) was chromatographed, eluting with 2.5–10% MeOH/$CH_2Cl_2$ containing 1% $NH_4OH$. The free amine was dissolved in anhydrous ether and ethereal HCl was added to afford 1-(R)-[4-(3,4-dichlorobenzyl)piperidin-1-ylmethyl]-2-methylpropylamine as the HCl salt.

Step 7

3,4,5-Trimethoxy isocynate (1.9 g, 9.11 mmol) was added to a solution of 1-(R)-[4-(3,4-dichlorobenzyl)piperidin-1-ylmethyl]-2-methylpropylamine (2.5 g, 7.59 mmol) in methylene chloride (25 ml) under argon atmosphere. The solution was stirred for 45 min., at room temperature, followed by 30 min., at 38° C. The reaction mixture was concentrated in vacuo. The crude product was chromatographed on a silica gel column, eluting with 1.5–2.5% MeOH/CH$_2$Cl$_2$ containing 1% NH$_4$OH to give 1-{1-(R)-[4-(3,4-dichlorobenzyl)piperidin-1-ylmethyl]-2-methylpropyl}-3-(3,4,5-trimethoxyphenyl)urea (3.7 g).

Step8

A solution of 1-{1-(R)-[4-(3,4-dichlorobenzyl)piperidin-1-ylmethyl]-2-methylpropyl}-3-(3,4,5-trimethoxyphenyl)urea (0.19 g, 0.353 mmoles) in iodoethane (4 ml) was stirred overnight at 68° C. degrees under argon. The yellow mixture was concentrated in vacuo and the crude product was flash chromatographed, eluting with 3%–4% methanol/methylene chloride to give 4-(3,4-dichlorobenzyl)-1-ethyl-1-{3-methyl-2-[3-(3,4,5-trimethoxyphenyl)ureido]butyl}piperidinium iodide (0.18 g) as a yellow solid.

Proceeding as described in Example 1 above, but substituting ethyl iodide with a solution of methyl iodide (0.5 ml) in methylene chloride (20 ml) in Step 8 and stirring the reaction mixture at room temperature overnight gave 4-(3,4-dichlorobenzyl)-1-methyl-1-{3-methyl-2-[3-(3,4,5-trimethoxyphenyl)-ureido]butyl}piperidinium iodide.

Proceeding as described in Example 1 above, but substituting ethyl iodide with ethyl iodoacetate (5 ml) in Step 8 and stirring the reaction mixture at room temperature for 5 h gave 4-(3,4-dichlorobenzyl)-1-(ethoxycarbonylmethyl)-1-{3-methyl-2-[3-(3,4,5-trimethoxyphenyl)ureido]butyl}piperidinium iodide.

Example 15

4-(3,4-Dichlorobenzyl)-1-ethyl-1-{3-methyl-2-[3-(3,4,5-trimethoxyphenyl)-ureido]butyl}piperidinium chloride

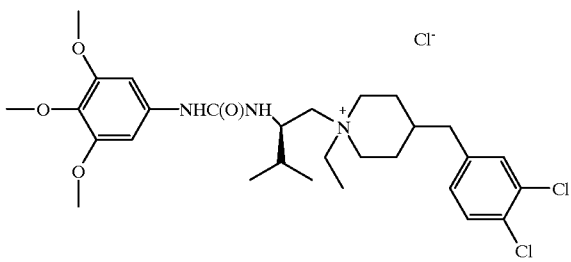

A solution of 4-(3,4-dichlorobenzyl)-1-ethyl-1-{3-methyl-2-[3-(3,4,5-trimethoxyphenyl)ureido]butyl}piperidinium iodide (0.2 g) in methanol (5 ml) was slowly passed through a column of Dowex 1x8-50 ion exchange resin (3 g). The eluted product was concentrated in vacuo to give 4-(3,4-dichlorobenzyl)-1-ethyl-1-{3-methyl-2-[3-(3,4,5-trimethoxyphenyl)ureido]butyl}piperidinium chloride.

Example 16

4-(3,4-Dichlorobenzyl)-1-(2-hydroxyethyl)-1-{3-methyl-2-[3-(3,4,5-trimethoxyphenyl)ureido]butyl}piperidinium chloride

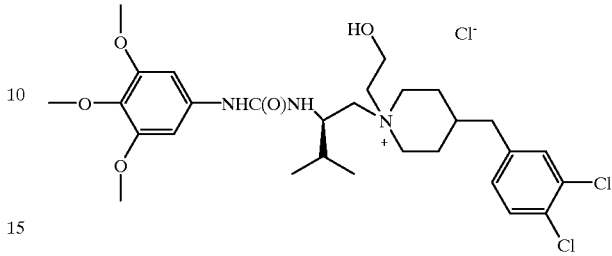

1-{1-(R)-[4-(3,4-Dichlorobenzyl)piperidin-1-ylmethyl]-2-methylpropyl}-3-(3,4,5-trimethoxyphenyl)urea (0.21 g) was dissolved in 2-chloroethanol (5 mL) and the solution heated in an oil bath at 90° C. After stirring under nitrogen for 1 day, the reaction mixture was cooled and then poured directly onto a pad of silica gel. Elution with 6% methanol in methylene chloride and then 11% methanol in methylene chloride, followed by solvent removal from the appropriate fractions gave 4-(3,4-dichlorobenzyl)-1-(2-hydroxyethyl)-1-{3-methyl-2-[3-(3,4,5-trimethoxyphenyl)ureido]butyl}piperidinium chloride (41.6 mg).

Example 17

Formulation Examples

The following are representative pharmaceutical formulations containing a compound of Formula (I).

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
|---|---|
| compound of this invention | 0.2 g |
| sodium acetate buffer solution, 0.4M | 2.0 ml |
| HCl (1N) or NaOH (1N) | q.s. to suitable pH |
| water (distilled, sterile) | q.s. to 20 ml |

Liposomal Formulation

The following ingredients are mixed to form a liposomal formulation.

| Ingredient | Amount |
|---|---|
| compound of this invention | 10 mg |
| L-α-phosphatidylcholine | 150 mg |
| tert-butanol | 4 ml |

Freeze dry the sample and lyophilize overnight. Reconstitute the sample with 1 ml 0.9% saline solution. Liposome size can be reduced by sonication Example 18

CCR-3 Receptor Binding Assay—in vitro

The CCR-3 antagonistic activity of the compounds of the invention was determined by their ability to inhibit the binding of $^{125}$I eotaxin to CCR-3 L1.2 transfectant cells ((see Ponath, P. D. et al., *J. Exp. Med.*, Vol. 183, 2437–2448, (1996)).

The assay was performed in Costar 96-well polypropylene round bottom plates. Test compounds were dissolved in DMSO and then diluted with binding buffer (50 mM HEPES, 1 mM $CaCl_2$, 5 mM $MgCl_2$, 0.5% bovine serum albumin (BSA), 0.02% sodium azide, pH 7.24) such that the final DMSO concentration was 2%. 25 μl of the test solution or only buffer with DMSO (control samples) was added to each well, followed by the addition of 25 μl of $^{125}$I-eotaxin (100 pmol) (NEX314, New England Nuclear, Boston, Mass.) and $1.5 \times 10^5$ of the CCR-3 L1.2 transfected cells in 25 μl binding buffer. The final reaction volume was 75 μl.

After incubating the reaction mixture for 1 h at room temperature, the reaction was terminated by filtering the reaction mixture through polyethylenimine treated Packard Unifilter GF/C filter plate (Packard, Chicago, Ill.). The filters were washed four times with ice cold wash buffer containing 10 mm HEPES and 0.5M sodium chloride (pH 7.2) and dried at 65° C. for approximately 10 min. 25 μl/well of Microscint-20™ scintillation fluid (Packard) was added and the radioactivity retained on the filters was determined by using the Packard TopCount™.

Compounds of this invention were active in this assay.

The $IC_{50}$ value (concentration of test compound required to reduce $^{125}$I-eotaxin binding to the CCR-3 L 1.2 transfected cells by 50%) for some of the compounds of the invention was:

| Cpd # | $IC_{50}$, μM | Cpd # | $IC_{50}$, μM |
|---|---|---|---|
| 7 | 0.415 | 88 | 1.47 |
| 8 | 0.24 | 89 | 1.68 |
| 19 | 0.945 | 91 | 1.89 |
| 20 | 0.952 | 93 | 3.37 |
| 23 | 1.33 | 99 | 2.36 |
| 24 | 1.37 | 100 | 2.47 |
| 25 | 1.46 | 107 | 1.14 |
| 59 | 0.95 | 109 | 2.84 |
| 61 | 1.76 | 110 | 3.05 |
| 78 | 5.03 | 117 | 1.33 |
| 84 | 0.69 | 118 | 1.5 |
| 86 | 1.16 | 121 | 3.52 |

Example 19

Inhibition of Eotaxin Mediated Chemotaxis of CCR-3 L1.2 Transfectant Cells—In vitro Assay The CCR-3 antagonistic activity of the compounds of this invention was determined by measuring the inhibition of eotaxin mediated chemotaxis of the CCR-3 L1.2 transfectant cells, using the slight modification of the method described in Ponath, P. D. et al., *J. Clin. Invest.* 97: 604–612 (1996). The assay was performed in a 24-well chemotaxis plate (Costar Corp., Cambridge Mass.). CCR-3 L1.2 transfectant cells were grown in culture medium containing RPMI 1640, 10% Hyclone™ fetal calf serum, 55 mM 2-mercaptoethanol and Geneticin 418 (0.8 mg/ml). 18–24 hours before the assay, the transfected cells were treated with n-butyric acid at a final concentration of 5 mM/$1 \times 10^6$ cells/ml, isolated and resuspended at $1 \times 10^7$ cells/ml in assay medium containing equal parts of RPMI 1640 and Medium 199 (M 199) with 0.5% bovine serum albumin.

Human eotaxin suspended in phosphate buffered saline at 1 mg/ml was added to bottom chamber in a final concentration of 100 nm. Transwell culture inserts (Costar Corp., Cambridge Mass.) having 3 micron pore size were inserted into each well and L1.2 cells ($1 \times 10^6$) were added to the top chamber in a final volume of 100 μl. Test compounds in DMSO were added both to the top and bottom chambers such that the final DMSO volume was 0.5%. The assay was performed against two sets of controls. The positive control contained cells with no test compound in the top chamber and only eotaxin in the lower chamber. The negative control contained cells with no test compound in the top chamber and neither eotaxin nor test compound in lower chamber. The plate was incubated at 37° C. After 4 h, the inserts were removed from the chambers and the cells that had migrated to the bottom chamber were counted by pipetting out 500 μl of the cell suspension from the lower chamber to 1.2 ml Cluster tubes (Costar) and counting them on a FACS for 30 sec.

Compounds of this invention were active in this assay.

The $IC_{50}$ value (concentration of test compound required to reduce eotaxin mediated chemotaxis of CCR-3 L 1.2 transfected cells by 50%) for some of the compounds of the invention was:

| CPD # | $IC_{50}$ μM | CPD # | $IC_{50}$ μM |
|---|---|---|---|
| 57 | 0.24 | 84 | 0.46 |
| 59 | 0.21 | 93 | 0.06 |

Example 20

Inhibition of Eotaxin Mediated Chemotaxis of Human Eosinophils—In vitro Assay

The ability of compounds of the invention to inhibit eotaxin mediated chemotaxis of human eosinophils was assessed using a slight modification of procedure described in Carr, M. W. et al., *Proc. Natl. Acad. Sci. USA*, 91: 3652–3656 (1994). Experiments were performed using 24 well chemotaxis plates (Costar Corp., Cambridge Mass.). Eosinophils were isolated from blood using the procedure described in PCT Application, Publication No. WO 96/22371. The endothelial cells used were the endothelial cell line ECV 304 obtained from European Collection of Animal Cell Cultures (Porton Down, Salisbury, U.K.). Endothelial cells were cultured on 6.5 mm diameter Biocoatg Transwell tissue culture inserts (Costar Corp., Cambridge Mass.) with a 3.0 μM pore size. Culture media for ECV 304 cells consisted of M199, 10% Fetal Calf Serum, L-glutamine and antibiotics. Assay media consisted of equal parts RPMI 1640 and M199, with 0.5% BSA. 24 h before the assay $2\times10^5$ ECV 304 cells were plated on each insert of the 24-well chemotaxis plate and incubated at 37° C. 20 nM of eotaxin diluted in assay medium was added to the bottom chamber. The final volume in bottom chamber was 600 μl. The endothelial coated tissue culture inserts were inserted into each well. $10^6$ eosinophil cells suspended in 100 μl assay buffer were added to the top chamber. Test compounds dissolved in DMSO were added to both top and bottom chambers such that the final DMSO volume in each well was 0.5%. The assay was performed against two sets of controls. The positive control contained cells in the top chamber and eotaxin in the lower chamber. The negative control contained cells in the top chamber and only assay buffer in the lower chamber. The plates were incubated at 37° C. in 5% $CO_2/95\%$ air for 1–1.5 h.

The cells that had migrated to the bottom chamber were counted using flow cytometry. 500 μl of the cell suspension from the lower chamber was placed in a tube, and relative cell counts were obtained by acquiring events for a set time period of 30 seconds.

Compounds of this invention were active in this assay.

Example 21

Inhibition of Eosinophil Influx into the Lungs of Ovalbumin Sensitized Balb/c Mice by CCR-3 Antagonist—In vivo Assay The ability of the compounds of the invention to inhibit leukocyte infiltration into the lungs was determined by measuring the inhibition of eosinophil accumulation into the bronchioalveolar lavage (BAL) fluid of Ovalbumin (OA)-sensitized balb/c mice after antigen challenge by aerosol. Briefly, male balb/c mice weighing 20–25 g were sensitized with OA (10 μg in 0.2 ml aluminum hydroxide solution) intraperitoneally on days 1 and 14. After a week, the mice were divided into ten groups. Test compound or only vehicle (control group) or anti-eotaxin antibody (positive control group) was administered. After 1 h, the mice were placed in a Plexiglass box and exposed to OA aerosol generated by a PARISTAR™ nebulizer (PARI, Richmond, Va.) for 20 min. Mice which had not been sensitized or challenged were included as negative control. After 24 or 72 h, the mice were anesthetized (urethane, approx. 1 g/kg, i.p.), a tracheal cannula (PE 60 tubing) was inserted and the lungs were lavaged four times with 0.3 ml PBS. The BAL fluid was transferred into plastic tubes and kept on ice. Total leukocytes in a 20 μl aliquot of the BAL fluid was determined by Coulter Counterm (Coulter, Miami, Fla.). Differential leukocyte counts were made on Cytospin™ preparations which had been stained with a modified Wright's stain (Diff-Quick™) by light microscopy using standard morphological criteria.

Compounds of this invention were active in this assay.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound selected from compounds of Formula (I):

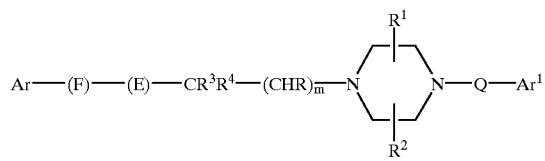

wherein:

$R^1$ and $R^2$ are, independently of each other, hydrogen or alkyl;

m is an integer from 0 to 3;

F is alkylene, alkenylene or a bond;

each R is independently hydrogen or alkyl, or R together with $R^4$ and the atoms to which they are attached form a carbocycle;

$R^3$ is H;

$R^4$ is alkyl, ($C_3$–$C_6$)cycloalkyl or hydroxyalkyl;

E is —$SO_2N(R^5)$—, —$N(R^6)SO_2N(R^5)$—, —$N(R^6)C(O)O$—, —$OC(O)N(R^5)$— or —$N(R^6)SO_2$, wherein $R^5$ and $R^6$ are individually H or alkyl or $N(R^5)$ or $N(R^6)$ together with $C(R^4)$ form a heterocycloamino moiety; provided that when E is —$SO_2N(R^5)$— or —$N(R^6)SO_2N(R^5)$—, then m>0;

Ar is ($C_6$–$C_{10}$)aryl, optionally substituted with one, two or three alkyl, alkenyl, halo, alkoxy, haloalkoxy, ($C_6$–$C_{10}$) aryl, phenoxy, ($C_5$–$C_{10}$)heteroaryl, —C(O)(alkyl), —C(O) (optionally substituted phenyl), —$SO_2$(alkyl), —$SO_2$NR'R", wherein R' and R" are hydrogen or alkyl; acylamino, acylaminoalkyl, (alkylene)NR'R", methylenedioxy, hydroxy, hydroxyalkyl, NR'R", —CONR'R", -(alkylene)-CONR'R", COOR', (alkylene)$CO_2$R', CN, alkylthio, $NO_2$, haloalkyl, (alkylene)NR'$SO_2$R'", —NR'$SO_2$R'" wherein R'" is alkyl or NR'R"; or a combination thereof;

$Ar^1$ is ($C_6$–$C_{10}$)aryl, optionally substituted with one, two or three alkyl, ($C_6$–$C_{10}$)heteroalkyl, alkoxy, halo, haloalkyl, haloalkoxy, alkylthio, methylene dioxy, nitro; NR'R" or a combination thereof;

Q is $C_1$–$C_6$ alkylene;

or a pharmaceutically acceptable salt thereof.

2. The compound of claim 1 wherein Ar is phenyl, optionally substituted with one, two or three methyl, methoxy, fluoro, chloro, dimethylamino, acetyl, hydroxy, amino, methylenedioxy, —$SO_2$Me, 2-acetylaminoethyl, 2-aminoethyl, aminomethyl, hydroxymethyl, aminocarbonyl, —COOH, carboxymethyl, methoxycarbonylmethyl, aminocarbonylmethyl, dimethylaminocarbonylmethyl, acetylaminomethyl, methylsulfonylamino, methylsulfonylaminomethyl, dimethylaminosulfonylaminomethyl, dimethylamino, or a combination thereof.

3. The compound of claim 2 wherein Ar is phenyl, 4-chlorophenyl, 3,4-difluorophenyl, 4-methylphenyl, 3-methoxyphenyl, 4-methoxyphenyl, 4-hydroxyphenyl, 3-methylenedioxyphenyl, 4-methylsulfonylphenyl, 4-(2-aminoethyl)phenyl, 4-(aminomethyl)phenyl, (hydroxymethyl)phenyl, 3-aminocarbonylphenyl, 3-carboxyphenyl, 2,5-dimethoxyphenyl, 3,5-dimethoxyphenyl, 3,4-dimethoxyphenyl, 3,4,5-trimethoxyphenyl, 3-aminocarbonylmethylphenyl, 3-acetylaminomethyphenyl, 3-carboxymethylphenyl, 3-methylsulfonylaminophenyl, 3-methylsulfonylaminomethylphenyl or 4-aminophenyl.

4. The compound of claim 1 wherein $Ar^1$ is phenyl substituted with one or two substituents selected from methyl, methoxy, chloro, fluoro, trifluoromethyl, nitro or a combination thereof.

5. The compound of claim 4 wherein $Ar^1$ is 4-nitrophenyl, 4-trifluoromethylphenyl, 4-chlorophenyl, 3,4-difluorophenyl, 2,3-dichlorophenyl, 3-methyl-4-nitrophenyl, 3-chloro-4-fluorophenyl, or 3,4-dichlorophenyl.

6. The compound of claim 1, wherein:

mis 1;

F is a bond;

Q is methylene; and

E is —$SO_2$N($R^5$)—.

7. The compound of claim 6, wherein $R^4$ is alkyl and $R^5$ is hydrogen.

8. The compound of claim 7, wherein $R^4$ is 1-methylethyl, 1,1-dimethylethyl, 2-methylpropyl, 3-hydroxypropyl, 1-hydroxyethyl or 2-hydroxyethyl.

9. A compound selected from compounds of formula (II):

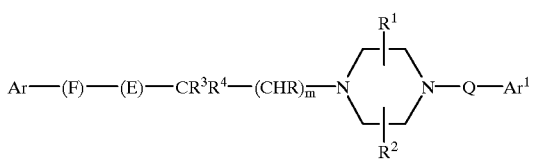

II wherein:

$R^1$ and $R^2$ are, independently of each other, hydrogen or alkyl;

m is an integer from 0 to 3;

F is alkylene, alkenylene or a bond;

each R is independently hydrogen or alkyl, or R together with $R^4$ and the atoms to which they are attached form a carbocycle;

$R^3$ is H;

$R^4$ is alkyl, haloalkyl, heteroaralkyl, alkoxyalkyl, cycloalkyl, (alkyl)S(O)$_{0-2}$(alkyl)-, (alkylene)C(O)Z wherein Z is OH, alkoxy or hydroxyalkyl;

E is —N($R^6$)C(O)N($R^5$)—, —N($R^6$)C(S)N($R^5$)—, —C(O)N($R^5$)—, or —N($R^6$)C(O)— wherein:

$R^5$ and $R^6$ are individually H or alkyl or N($R^5$) together with C($R^4$) form a heterocycloamino moiety;

provided that when E is —C(O)N($R^5$)—, —N($R^6$)C(O)N($R^5$)—, or —N($R^6$)C(S)N($R^5$), then m>0.

Ar is ($C_6$–$C_{10}$)aryl, optionally substituted with one, two or three alkyl, alkenyl, alkoxy, haloalkoxy, halo, $C_6$–$C_{10}$ aryl, ($C_5$–$C_{10}$)heteroaryl, —C(O)(alkyl), —C(O)(aryl), —C(O)(heteroaryl), —$SO_2$(alkyl), —$SO_2$NR'R, wherein R' and R" are hydrogen or alkyl; acylamino, acylaminoalkyl, (amino) acylaminoalkyl; (alkylene)NR'R", methylenedioxy, hydroxy, hydroxyalkyl, NR'R", —CONR'R", -(alkylene)-CONR'R", COOR', -(alkylene)-COOR', CN, alkythio, $NO_2$, haloalkyl, (alkylene)NR'$SO_2$R'", NR'$SO_2$R'", wherein R'" is alkyl or NR'R"; or a combination thereof;

$Ar^1$ is ($C_6$–$C_{10}$)aryl or ($C_6$–$C_{10}$)aralkyl, optionally substituted with one, two or three alkyl, ($C_6$–$C_{10}$)aryl, phenoxy, ($C_6$–$C_{10}$)heteroaryl, ($C_6$–$C_{10}$ aryl)$CO_2$, alkoxy, halo, haloalkyl, haloalkoxy, alkylthio, methylene dioxy, nitro, NR'R", or a combination thereof;

Q is $C_1$–$C_6$ alkylene(W)- wherein W is a bond, —O—, —S—, —$O_2$C—, C(O), or —C(O)N($R^5$)—;

or a pharmaceutically acceptable salt thereof.

10. The compound of claim 9, wherein:

Ar is phenyl, 4-chlorophenyl, 3,4-difluorophenyl, 4-methylphenyl, 3-methoxyphenyl, 4-methoxyphenyl, 4-hydroxyphenyl, 3,4-methylenedioxyphenyl, 4-methylsulfonylphenyl, 4-[(2-acetylamino)ethyl] phenyl, 4-{2-[(R)-amino-3-methyl-butyrylamino] ethyl}phenyl, 4-(2-aminoethyl)phenyl, 4-(aminomethyl)phenyl, 4-(hydroxymethyl)phenyl, 3-aminocarbonylphenyl, 3-carboxyphenyl, 2,5-dimethoxyphenyl, 3,5-dimethoxyphenyl, 3,4-dimethoxyphenyl, 3,4,5-trimethoxyphenyl, 3-aminocarbonylmethylphenyl, 3-acetylaminomethylphenyl, 3-carboxymethylphenyl, 3-methylsulfonylaminophenyl, 3-methylsulfonylaminomethylphenyl, or 4-aminophenyl; and $Ar^1$ is 4-nitrophenyl, 4-trifluoromethylphenyl, 4-chlorophenyl, 3,4-difluorophenyl, 2,3- dichlorophenyl, 3-methyl-4-nitrophenyl, 3-chloro-4-fluorophenyl or 3,4-dichlorophenyl.

11. The compound of claim 9, wherein:
m is 1;
F is a bond; and
Q is methylene.

12. The compound of claim 11, wherein:
R, $R^1$, $R^2$ and $R^3$ are hydrogen; and
E is —C(O)N($R^5$)— or —N($R^6$)C(O)N($R^5$)—.

13. The compound of claim 12, wherein $R^4$ is alkyl and $R^5$ and $R^6$ are hydrogen.

14. The compound of claim 9, wherein $R^4$ is 1-methylethyl, 1,1-dimethylethyl, 2-methylpropyl, 3-hydroxypropyl, 2-hydroxyethyl or 2-hydroxyethyl.

15. N-{1-(S)-[4-(3,4-dichlorobenzyl)piperazine-1-ylmethyl]-2-methyl-propyl}-4-methylbenzamide.

16. N-{1-(R)-[4-(3,4-dichlorobenzyl)piperazin-1-ylmethyl]-2-methyl-propyl}-4-(2-aminoethyl)benzamide.

17. A pharmaceutical composition comprising a therapeutically effective amount of a compound of claim 1 and a pharmaceutically acceptable excipient.

18. A pharmaceutical composition comprising a therapeutically effective amount of a compound of claim 9 and a pharmaceutically acceptable excipient.

19. A method for treating inflammatory or allergic diseases in a mammal which method comprises administering to said mammal a therapeutically effective amount of a compound of Formula (I):

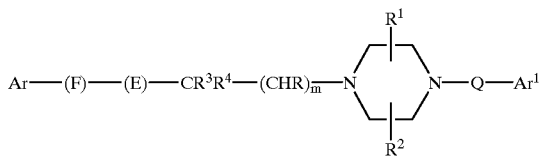

I wherein:
$R^1$ and $R^2$ are, independently of each other, hydrogen or alkyl;
m is an integer from 0 to 3;
F is alkylene, alkenylene or a bond;
each R is independently hydrogen or alkyl, or R together with $R^4$ and the atoms to which they are attached form a carbocycle;
$R^3$ is H;
$R^4$ is alkyl or hydroxyalkyl;
E is —$SO_2$N($R^5$)—, —N($R^6$)$SO_2$N($R^5$)—, —N($R^6$)C(O)O—, —OC(O)N($R^6$)— or —N($R^6$)$SO_2$—, wherein $R^5$ and $R^6$ are individually H or alkyl or N($R^5$) or N($R^6$) together with C($R^4$) form a heterocycloamino; provided that when E is —$SO_2$N($R^5$)— or —N($R^6$)$SO_2$N($R^5$)—, then m>0;
Ar is ($C_6$–$C_{10}$)aryl, optionally substituted with one, two or three halo, alkyl, alkenyl, alkoxy, haloalkoxy, $C_6$–$C_{10}$ aryl, phenoxy, ($C_5$–$C_{10}$)heteroaryl, —C(O)(alkyl), —C(O)(optionally substituted phenyl), —C(O)heteroaryl, —$SO_2$(alkyl), —$SO_2$NR'R", wherein R' and R" are hydrogen or alkyl; acylamino, acylaminoacyl, (amino)acylaminoacyl, NR'R", (alkylene)NR'R", methylenedioxy, hydroxy, hydroxyalkyl, —CONR'R", -(alkylene)-CONR'R", —COOR', -(alkylene)-COOR', CN, alkylthio, $NO_2$, haloalkyl, (alkylene)NR'$SO_2$R'", —NR'$SO_2$R'", wherein R'" is alkyl or NR'R"; or a combination thereof;

$Ar^1$ is ($C_6$–$C_{10}$)aryl, optionally substituted with one, two or three alkyl, ($C_6$–$C_{10}$)heteroalkyl, alkoxy, halo, haloalkyl, haloalkoxy, alkylthio, methylenedioxy, nitro, NR'R", or a combination thereof,
Q is a $C_1$–$C_6$ alkylene chain;
or a pharmaceutically acceptable salt thereof.

20. The method of claim 19, wherein said inflammatory or allergic diseases are selected from the group consisting of asthma, allergic rhinitis, hypersensitivity lung diseases, hypersensitivity pneumonitis, eosinophilic pneumonias, inflammatory bowel diseases, psoriasis, dermatitis and eczema.

21. A method for treating inflammatory or allergic diseases in a mammal which method comprises administering to said mammal a therapeutically effective amount of a compound of Formula (II):

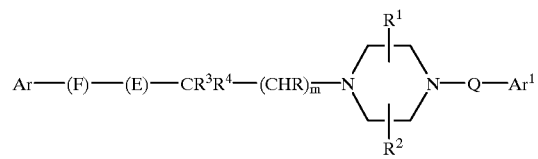

II wherein:
$R^1$ and $R^2$ are, independently of each other, hydrogen or alkyl;
m is an integer from 0 to 3;
F is alkylene, alkenylene or a bond;
each R is independently hydrogen or alkyl, or R together with $R^4$ and the atoms to which they are attached form a carbocycle;
$R^3$ is H;
$R^4$ is alkyl, haloalkyl, heteroaralkyl, alkoxyalkyl, cycloalkyl, (alkyl)S(O)$_{0-2}$(alkyl)-, (alkylene)C(O)Z wherein Z is OH, alkoxy or hydroxyalkyl;
E is —N($R^6$)C(O)N($R^5$)—, —N($R^6$)C(S)N($R^5$)—, —C(O)N($R^5$)—, or —N($R^6$)C(O)—
wherein:
$R^5$ and $R^6$ are individually H or alkyl or N($R^5$) together with C($R^4$) form a heterocycloamino moiety;
provided that when E is —C(O)N($R^5$)—, —N($R^6$)C(O)N($R^5$)—, or —N($R^6$)C(S)N($R^5$), then m>0.
Ar is ($C_6$–$C_{10}$)aryl, optionally substituted with one, two or three alkyl, alkenyl, alkoxy, haloalkoxy, halo, $C_6$–$C_{10}$ aryl, ($C_5$–$C_{10}$)heteroaryl, —C(O)(alkyl), —C(O)aryl, C(O)heteroaryl, —$SO_2$(alkyl), —$SO_2$NR'R, wherein R' and R" are hydrogen or alkyl; acylamino, acylaminoalkyl, (amino)acylaminoalkyl; (alkyl)NR'R", methylenedioxy, hydroxy, hydroxyalkyl, NR'R", —CONR'R", -(alkylene)-CONR'R", COOR', -(alkylene)-COOR', CN, alkythio, $NO_2$, haloalkyl, (alkylene)NR'$SO_2$R'", NR'$SO_2$R'", wherein R'" is alkyl, or NR'R"; or a combination thereof;
$Ar^1$ is ($C_6$–$C_{10}$)aryl or ($C_6$–$C_{10}$)aralkyl, optionally substituted with one, two or three alkyl, $C_6$–$C_{10}$(aryl), phenoxy, $C_6$–$C_{10}$(heteroaryl), ($C_6$–$C_{10}$ aryl)$CO_2$, alkoxy, halo, haloalkyl, haloalkoxy, alkylthio, methylene dioxy, nitro, NR'R", or a combination thereof;
Q is $C_1$–$C_6$ alkylene(W)-, wherein W is a bond, —O—, —S—, —$O_2$C—, C(O)N($R^5$), or C(O);
or a pharmaceutically acceptable salt thereof.

22. The method of claim 21, wherein said inflammatory or allergic diseases are selected from the group consisting of asthma, allergic rhinitis, hypersensitivity lung diseases, hypersensitivity pneumonitis, eosinophilic pneumonias, inflammatory bowel diseases, psoriasis, dermatitis and eczema.

23. The method of claim 22, wherein said inflammatory or allergic disease is asthma.

* * * * *